US010526582B2

(12) United States Patent
Kim et al.

(10) Patent No.: US 10,526,582 B2
(45) Date of Patent: Jan. 7, 2020

(54) MULTI-LAYERED CELL CONSTRUCTS AND METHODS OF USE AND PRODUCTION USING ENZYMATICALLY DEGRADABLE NATURAL POLYMERS

(71) Applicant: TRUSTEES OF BOSTON UNIVERSITY, Boston, MA (US)

(72) Inventors: Joshua Jaeyun Kim, Allston, MA (US); Joyce Yun-Wei Wong, Chestnut Hill, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 375 days.

(21) Appl. No.: 14/891,173

(22) PCT Filed: May 14, 2014

(86) PCT No.: PCT/US2014/037946
§ 371 (c)(1),
(2) Date: Nov. 13, 2015

(87) PCT Pub. No.: WO2014/186430
PCT Pub. Date: Nov. 20, 2014

(65) Prior Publication Data
US 2016/0115457 A1   Apr. 28, 2016

Related U.S. Application Data

(60) Provisional application No. 61/824,197, filed on May 16, 2013.

(51) Int. Cl.
| C12N 5/071 | (2010.01) |
| C12N 5/00 | (2006.01) |
| A61L 27/60 | (2006.01) |
| A61L 27/38 | (2006.01) |
| A61L 27/50 | (2006.01) |

(52) U.S. Cl.
CPC ........ *C12N 5/0698* (2013.01); *A61L 27/3804* (2013.01); *A61L 27/3808* (2013.01); *A61L 27/3813* (2013.01); *A61L 27/3826* (2013.01); *A61L 27/3834* (2013.01); *A61L 27/3891* (2013.01); *A61L 27/507* (2013.01); *A61L 27/60* (2013.01); *C12N 5/0062* (2013.01); *C12N 5/0068* (2013.01); *C12N 2533/74* (2013.01); *C12N 2533/78* (2013.01); *C12N 2535/00* (2013.01); *C12N 2539/00* (2013.01)

(58) Field of Classification Search
None
See application file for complete search history.

(56) References Cited

U.S. PATENT DOCUMENTS 7,405,078 B2   7/2008   Okano et al.
2006/0281173 A1   12/2006   Fukuda et al.
2007/0059763 A1*   3/2007   Okano ................. G01N 33/566
435/7.1
2011/0151565 A1   1/2011   Hase et al.
2012/0141547 A1   6/2012   Zhao et al.

FOREIGN PATENT DOCUMENTS

JP   2003/038170 A   2/2003
WO   01/68799 A1   9/2001

OTHER PUBLICATIONS

Nichol et al., "Modular Tissue Engineering: Engineering Biological Tissues from the Bottom Up", Soft Matter, 2009, vol. 5, No. 7, pp. 1312-1319, pp. 1-17.*
Brandl et al., "Enzymatically degradable poly(ethylene glycol) based hydrogels for adipose tissue engineering", Biomaterials, 31:3957-3966 (2010).
Burdick et al., "Moving from static to dynamic complexity in hydrogel design", Nature Communications, 3:1269 (2012).
Canavan et al., "Cell sheet detachment affects the extracellar matrix: A surface science study comparing thermal liftoff, enzymatic, and mechanical methods", J Biomed Mater Res, 75A:1-13 (2005).
Haraguchi et al., "Regenerative Therapies Using Cell Sheet-Based Tissue Engineering for Cardiac Disease", Cardiology Research and Practice, Article ID 845170, pp. 1-8 (2011).
Kim et al., "A novel enzyme degradable hydrogel based cell sheet harvest and transfer system with high cell viability" Jun. 14, 2013. Article retrieved from the internet:<https://ww2.eventrebels.com/ERImages/9188/2320152/26323-2-10311.pdf>.
Sakai et al., "Control of cellular adhesiveness in an alginate-based hydrogel by varying peroxidase and H2O2 concentrations during gelation", Acta Biomaterialia 6:1446-1452 (2010).
Sannino et al., "Biodegradable cellulose-based hydrogels: design and applications", Materials 2:353-373 (2009).
Shimizu et al., "Long-Term Survival and Growth of Pulsatile Myocardial Tissue Grafts Engineered by the Layering of the Cardiomyocyte Sheets", Tissue Engineering, 12(3):499-507 (2006).

(Continued)

*Primary Examiner* — Laura Schuberg
(74) *Attorney, Agent, or Firm* — Nixon Peabody, LLP; Ronald I. Eisenstein; Susanna C. Benn

(57) ABSTRACT

The present disclosure relates generally to the fields of tissue engineering and regenerative medicine. More particularly, the present disclosure generally relates to systems, methods, compositions and kits to rapidly fabricate functionalized three-dimensional tissues from multiple stacks of cell sheets using enzyme-digestible hydrogel substrates as supports for the cell sheets. Methods to generate the multi-layered cell constructs comprise contacting a cell-sheet on one digestible substrate with another cell-sheet on a different digestible substrate, enzymatically digesting with a first enzyme to remove the first substrate and subsequently adding repeating the steps to add another cell-sheet on same digestible substrate to form a multi-layered cell construct as disclosed herein. Additional aspects relate to using the multi-layered cell constructs for therapeutic use, research and in screening assays.

16 Claims, 14 Drawing Sheets

(56) References Cited

OTHER PUBLICATIONS

Yang et al., "Synthesis and Characterization of Enzymatically Degradable PEG-Based Peptide-Containing Hydrogels", Macromol. Biosci. 10:445-454 (2010).
Athanasiou et al., "Interspecies Comparisons of In Situ Intrinsic Mechanical Properties of Distal Femoral Cartilage", Journal of Orthopaedic Research 9(3):330-340 (1991).
Burdick et al., "Moving from static to dynamic complexity in hydrogel design", Nature Communications 3:1269 (23012).
Chaudhuri et al., "Preparation of Collagen-Coated Gels that Maximize In Vitro Myogenesis of Stem Cells by Matching the Lateral Elasticity of In Vivo Muscle", Protocols for Adult Stem Cells, 621:185-202 (2010).
Collinsworth et al., "Apparent elastic modulus and hysteresis of skeletal muscle cells throughout differentiation", Am J Physiol Cell Physiol. 283(4):C1219-C1227 (2002).
Dahl et al., "An Ultrastructural Analysis of Collagen in Tissue Engineered Arteries", Ann Biomed Eng., 35(10):1749-1755 (2007).
Elloumi-Hannachi et al., "Cell sheet engineering: a unique nanotechnology for scaffold-free tissue reconstruction with clinical applications in regenerative medicine", Journal of Internal Medicine 267(1):54-70 (2010).
Engler et al., "Matrix Elasticity Directs Stem Cell Lineage Specification", Cell 126(4):677-689 (2006).
Engler et al., "Myotubes differentiate optimally on substrates with tissue-like stiffness: pathological implications for soft or stiff microenvironments", The Journal of Cell Biology 166(6):877-887(2004).
Even-Ram et al., "Matrix Control of Stem Cell Fate", Cell 126(4):645-617 (2006).
Isenberg et al., "Micropatterned cell sheets with defined cell and extracellular matrix orientation exhibit anisotropic mechanical properties", Journal of Biomechanics 45(5):756-761 (2012).
Kloxin et al., "Photodegradable hydrogels for dynamic tuning of physical and chemical properties", Science 324(5923)59-63 (2009).
Kot et al., "Elastic Modulus of Muscle and Tendon with Shear Wave Ultrasound Elastography: Variations with Different Technical Settings", PloS One 7(8):e44348 (2012).
Leipzig et al., "The effect of substrate stiffness on adult neural stem cell behavior", Biomaterials 30(36):6867-6878(2009).
Levental et al., "Soft biological materials and their impact on cell function", Soft Matter 3:299-306 (2006).
Liu et al., "Impact of the composition of alginate and gelatin derivatives in bio-conjugated hydrogels on the fabrication of cell sheets and spherical tissues with living cell sheaths", Acta Biomaterialia 9(5):6616-6623 (2013).
Martina et al., "Biodegradable polymers applied in tissue engineering research: A review", Polymer International 56(2):145-157 (2007).
Murugan et al., "Design Strategies of Tissue Engineering Scaffolds with Controlled Fiber Orientation", Tissue Engineering 13(8):1845-1866 (2007).
Ogushi et al., "Synthesis of Enzymatically-Gellable Carboxymethylcellulose for Biomedical Applications", Journal of Bioscience and Bioengineering, 104(1):30-33 (2007).
Patel-Hett et al., "Signal transduction in vasculogenesis and developmental angiogenesis", Int. J. Dev. Biol. 55:353-363 (2011).
Sacharidou et al., "Molecular Mechanisms Controlling Vascular Lumen Formation in Three-Dimensional Extracellular Matrices", Cells Tissues Organs 2, 195(1-2):122-143 (2012).
Saha et al., "Substrate Modulus Directs Neural Stem Cell Behavior", Biophysical Journal 95(9):4426-4438 (2008).
Sakai et al., "Enzymatically crosslinked carboxymethylcellulose-tyramine conjugate hydrogel: Cellular adhesiveness and feasibility for cell sheet technology", Acta Biomaterialia 5(2):554-559 (2009).
Sakai et al., "Peroxidase-Catalyzed Cell Encapsulation in Subsieve-Size Capsules of Alginate with Phenol Moieties in Water-Immiscible Fluid Dissolving H2O2", Biomacromolecules 8(8):2622-2626 (2007).
Sakai et al., "Synthesis and characterization of both ionically and enzymatically cross-linkable alginate", Acta Biomaterialia 3(4):495-501 (2007).
Sasagawa et al., "Design of prevascularized three-dimensional cell-dense tissues using a cell sheet stacking manipulation technology" Biomaterials 31(7):1646-1654 (2010).
Sekine et al., "Endothelial Cell Coculture Within Tissue-Engineered Cardiomyocyte Sheets Enhances Neovascularization and Improves Cardiac Function of Ischemic Hearts", Circulation 118(Suppl 1):S145-S152 (2008).
Shimizu et al., "Fabrication of Pulsatile Cardiac Tissue Grafts Using a Novel 3-Dimensional Cell Sheet Manipulation Technique and Temperature-Responsive Cell Culture Surface", Circulation Research 90:e40-e48 (2002).
Taylor et al., "Reassessment of brain elasticity for analysis of biomechanisms of hydrocephalus", Journal of Biomechanics 37(8):1263-1269 (2004).
Voytik-Harbin et al., "Small Intestinal Submucosa: A Tissue-Derived Extracellular Matrix That Promotes Tissue-Specific Growth and Differentiation of Cells in Vitro", Tissue Engineering 4(2):157-174 (1998).
Wagenseil et al., "Vascular Extracellular Matrix and Arterial Mechanics", Physiol Rev. 89:957-989 (2009).
Yang et al., "Reconstruction of functional tissues with cell sheet engineering", Biomaterials 28(34)5033-5043 (2007).
Yeung et al., "Effects of Substrate Stiffness on Cell Morphology, Cytoskeletal Structure, and Adhesion", Cell Motility and Cytoskeleton 60(1):24-34 (2005).
Yu et al., "Neutral axis location in bending and Young's modulus of different layers of arterial wall", Am J Physiol Heart Circ Physiol. 265(1):H52-H60 (1993).

* cited by examiner

PATTERNED PDMS:
20μm GROOVES, 50μm RIDGES

GELATIN MOLD PREPARATION

PATTERNED SUBSTRATE PREPARATION

PATTERNED CMC-ty

MULTI-LAYERED CELL CONSTRUCTS AND METHODS OF USE AND PRODUCTION USING ENZYMATICALLY DEGRADABLE NATURAL POLYMERS

CROSS REFERENCE TO RELATED APPLICATIONS

This application is a 371 National Phase Entry of International Patent Application No. PCT/US2014/037946 filed on May 14, 2014 which claims benefit under 35 U.S.C. § 119(e) of the U.S. provisional application No. 61/824,197 filed May 16, 2013, the contents of which are incorporated herein by reference in their entirety.

FIELD OF THE DISCLOSURE

The present disclosure relates generally to the fields of tissue engineering and regenerative medicine. More particularly, the present disclosure generally relates to systems, methods and compositions to fabricate rapidly functionalized three-dimensional thick tissues from multiple stacks of cell sheets using enzyme-digestible hydrogel substrates as supports for the cell sheets.

BACKGROUND OF THE DISCLOSURE

Tissue engineering holds the prospect of producing tissues in vitro to fill the need for tissue regeneration and provide faster and more complete healing for subjects. The clinical efficacy of synthetic-, allogeneic or xenogeneic-engineered tissues has been limited by various problems including thrombosis, immunorejection, chronic inflammation and poor mechanical properties of the tissues after implantation. In particular, cardiovascular tissue engineering and production of small blood vessels is needed.

The structural organization of cells and associated extracellular matrix (ECM) is critical to overall tissue function. Recapitulating the complex, highly organized structure of a target tissue is a key to achieve the unique functional characteristics of native tissue. However, this requires a system enables modulation of substrate physiochemical properties such as modulus, topology and surface chemistry. Currently available systems to grow engineered tissue do not offer the simultaneous control over all of these physiochemical properties. To recreate unique properties of a tissue, engineered tissue must mimic the complex structural characteristics of the tissue. Conventional tissue engineering approaches, i.e. seeding cells in pre-made artificial scaffolds, has limitations in reconstructing target tissue with specific structural characteristics. For example, in a vessel-like tissue, the structure defines its function: in the inner media layer, smooth muscle cell alignment in a herringbone pattern perpendicular to the flow direction allows for vessel tone control. Therefore, accurate mimicry of a tissue structure is key for generating functional and implantable engineered tissue.

Cell sheet technology has been suggested as an alternative to scaffold tissue engineering approaches because cell sheets preserve the integrated structure of cell and cell-secreted extracellular matrix (ECM) that accurately mimics 2D native tissue structure. Stacking patterned cell sheets according to the anatomy of the target tissue could not only produce biochemically and biomechanically equivalent three dimensional structure of the native tissue, but also restore the function of the tissue. Furthermore, because cell sheets could take a form of patches, tubes or folded structures depending on the tissue type, application potential of cell sheet technology is unlimited.

In the treatment of a severely damaged heart, cell transplantation utilizing a variety of stem cells has been attempted as an alternative therapy to heart transplantation which has been suffering from shortage of donors. Recently, based on such cell transplantation techniques, tissue transplantation techniques have been increasingly developed in which myocardial tissues are constructed three-dimensionally in vitro and then transplanted into a body. For example, various types of cell sheets have been successfully manufactured by using temperature-responsive culture dishes which are prepared by coating poly(N-isopropylacrylamide) (abbreviated to "PIAAm") on the surfaces of commercial polystyrene culture dishes with electron beams. In particular, as for myocardial cells, it has already been reported that myocardial tissue masses available as transplants can be developed by overlaying the thus prepared multiple myocardial cell sheets (Japanese Patent Application Laid-open No. 2003-38170, WO 01/068799, Simizu et al.: Fabrication of pulsatile cardiac tissue grafts using a novel 3-dimensional cell sheet manipulation technique and temperature-responsive cell culture surface: Circ Res. 2002; 90:e40-e48). The thus prepared myocardial tissue mass is found to exhibit electrical activities similar to those of normal myocardial tissues in vitro and in vivo. However, the heat-sensitive substrate is expensive and the temperature used to displace the cells from the substrate can damage the cells.

Accordingly, there is an urgent need for cost-effective, simple and reliable cell sheet harvest and transfer system that can be used without damaging cell layer integrity or viability on removal of the substrate or scaffold.

SUMMARY OF THE DISCLOSURE

The present disclosure generally relates to compositions comprising multi-layered cell sheet stacks, and methods to make such multi-layered cell sheet stacks that closely mimic three dimensional (3D) native tissue structures and compositions. In some embodiments, such multi-layered cell sheet stacks (herein also referred to as "multi-layered cell constructs") have numerous uses in medicine and in research. The method of making such a multi-layered cell sheet stacks comprises stacking individual layers of cell sheets, one on top of another.

The method comprises first culturing individual layers of cell sheets on scaffold/support materials or substrates that can be digested by specific enzymes, e.g., carboxymethyl cellulose (CMC) conjugated with tyramin (ty): CMC-ty; and alginate (Al) conjugated with tyramin (ty): Al-ty that can be degraded by cellulose and alginate lyase respectively. These specific enzymes do not digest the extracellular matrices of cells. A first cell sheet layer is flipped on to a receiving cell sheet layer to form a sandwich with the first cell sheet layer being on top of the sandwich and the receiving cell sheet layer being the bottom of the sandwich. Pressure is applied to the sandwich to encourage adhesion of the layers. This is then followed by digestion of the scaffold material in the first (top) cell sheet layer. It is important that both cell sheet layers have different digestible scaffold materials so that only the scaffold material of the first cell sheet layer, i.e., the top cell sheet layer with respect to the receiving cell sheet layer, is digested away. When digestion is completed, the receiving cell sheet layer now comprises cells from the two cell sheet layers. A second cell sheet layer is flipped on to this resultant receiving cell sheet layer to form a sandwich and the process in repeated again to attain the desired layers of cell sheets in 3D. In some embodiments, the scaffold material is also referred to as cell sheet substrate.

As disclosed herein, the inventors developed a cell sheet harvest and transfer system that can rapidly produce a multi-layer cell construct which can be formed into any 3D shape or confirmation. Any number of cell-sheets can be stacked on a receiving substrate to form a multi-layered cell construct as thick as desired and conforming to any 3-dimensional shape. In some embodiments, the second cell layers can be different 2D shapes, such that when they are stacked on other second cell layers and/or receiving layers with a different 2D shape, they from a 3D multi-layered cell construct of a specific 3D conformation much in the same way that 3-dimensional printing works. Here, a 3D multi-layered cell construct can be configured from virtually any shape from a digital model. Here, a three-dimensional multi-layered cell construct is achieved using an additive process, where successive layers of cell layers seeding on secondary substrates are laid down in different shapes onto the cells on the receiving substrate. In addition, each of the cell sheet can be patterned or micropatterned as desired to achieve the final multi-layered cell construct.

In one embodiment, this cell sheet harvest and transfer system facilitates the construction of vascular three-dimensional tissue constructs for a various medical, clinical and research purposes. In one embodiment, endothelial cells and/or smooth muscle cells and/or endothelial progenitor or precursor cells and/or mesenchymal stem cells are incorporated into individual cell sheets to facilitate the formation of blood vessels.

As disclosed herein, the inventors developed a cell sheet harvest and transfer system that can rapidly produce patterned 2D cell sheets in any shape for various cell types and stack cell sheets with high cell viability while preserving the patterns. Furthermore, the system, method and composition as disclosed herein allow control of substrate modulus or stiffness which can mimic cell type specific natural biomechanical environments. Accordingly, the systems, methods and compositions as disclosed herein can be used to rapidly fabricate functionalized three-dimensional thick tissues from multiple stacks of cell sheets that allow fabrication of tissue models, tissue engineered constructs and regenerative medicine. Each of the cell sheet can be non-patterned or patterned as desired to achieve the final multi-layered cell construct.

Accordingly, one aspect of the present disclosure relates to a method of making a multi-layered cell construct comprising: (a) contacting a second cell layer with a receiving cell layer, wherein the second cell layer is present on a second substrate, and the receiving cell layer comprises at least one cell layer and is present on a receiving substrate, and wherein the receiving substrate can be digested by a first enzyme, and the second substrate can be digested by a second enzyme, (b) applying pressure to the second substrate and the receiving substrate, and (c) applying a second enzyme to digest the second substrate, wherein after digestion of the second substrate, the receiving substrate comprises multiple cell layers comprising the at least one receiving cell layer and the second cell layer, and (d) repeating steps (a)-(c) for a desired number of times, wherein the second cell layer of the multiple cell layers present on the receiving substrate in step (c) is used as the receiving cell layer for step (a), and (e) applying a first enzyme to digest the receiving substrate to form a multi-layered cell construct.

In some embodiments, step (d) to step (e) are repeated a plurality of times for the desired number of cell-layers of the multi-layered cell construct or the desired thickness of the multi-layered cell construct. For example, at least about 2 times, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 80, 81, 82, 83, 84, 85, 85, 86, 87, 88, 89, 90, 91, 92, 93, 94, 95, 96, 97, 98, 99 and 100 times. For example, at least about 2-10 times, or about 10-50 times or about 50-100 times including any integer between 2 and 100.

In some embodiments, prior to the contacting steps of contacting the cell surface of the second substrate with the cells cultured on the receiving substrate, the method comprises culturing the cells on a receiving substrate for an appropriate period of time for the cells to form a confluent receiving cell layer, wherein the receiving substrate can be digested by a first enzyme, and culturing cells on a second substrate for an appropriate period of time for the cells to form a confluent second cell layer, wherein the second substrate can be digested by a second enzyme.

In some embodiments, the cells cultured on the receiving cell layer and the second cell layer are the same type, and in alternative embodiments, they are different cell types, such that the multi-layered cell substrate comprises cell layers of a variety (e.g., at least 2 or more than 2) cell types.

In some embodiments, the cell sheet can be patterned or micropatterned. In some embodiments, the patterning facilitates localization of specific cell types in the multi-layered cell construct.

In all aspects of the present disclosure, the receiving substrate and the second substrate comprise enzyme digestible polymers, e.g., enzyme digestible polymers, for example, an enzyme digestible hydrogel, where the receiving substrate and the second substrate are digested or degraded by different enzymes.

In some embodiments, the receiving substrate and/or second substrate comprises carboxylmethyl cellulose (CMC) which is digested by the enzyme cellulose. In some embodiments, the second substrate and/or receiving substrate is a hydrogel which comprises alginate (Al), and is digested by the enzyme alginate lyase. It is important that, if the receiving substrate comprises carboxylmethyl cellulose (CMC) and is digested by cellulose, the second substrate does not comprise CMC and/or is not digested by cellulose. Similarly, if the receiving substrate comprises alginate (Al) and is digested by alginate lyase, the second substrate does not comprise Al and/or is not digested by alginate lyase. In other words, the receiving substrate or scaffold material should ideally be different from that of one or more second substrate/scaffold material that would be placed on top of the receiving substrate.

In some embodiments, substrates comprising carboxylmethyl cellulose (CMC) and/or alginate (Al) are conjugated with tyramin (Ty), for example, substrates can comprise at least 1% carboxylmethyl cellulose-tyramin (CMC-Ty) and/or at least 1% alginate-tyramin (Al-ty).

In some embodiments, the enzymes used to digest and degrade the receiving and/or second substrates do not digest the extracellular matrices of cells (EMC).

In some embodiments, the second substrate and/or the receiving substrates are patterned substrates. In some embodiments, the second substrate and/or the receiving substrates have a predetermined substrate stiffness (or "modulus") to maintain the cell-specific characteristics of the cells in the cell layer on the substrate.

In some embodiments, the second cell layer and/or the receiving cell layer comprises cells selected from the group consisting of: mesenchymal stem cells (MSCs), myocyte precursor cells, myocytes, fibroblasts, chondrocytes, endothelial cells, epithelial cells, embryonic stem cells (ESCs), hematopoietic stem cells, anchorage-dependent cell precursors, induced pluripotent stem cells (iPSCs), cardiomyocytes, and combinations thereof. In some embodiments, the second and/or receiving layer comprises fibroblasts, keratinocytes, and mesemchymal stem cells. In some embodiments, iPSCs are derived from fibroblasts, keratinocytes, or mesemchymal stem cells. In some embodiments, the multi-layered cell substrate comprises fibroblasts, keratinocytes, and mesemchymal stem cells. In some embodiments, the second cell layer and/or the receiving cell layer comprises human cells.

Another aspect of the present disclosure relates to a composition comprising a multi-layered cell construct produced by the methods as disclosed herein.

In one embodiment, the present disclosure provides a composition comprising a multi-layered cell construct produced by two individual cell sheets according the described cell sheet harvest and transfer system, that is, a multi-layered cell construct produced with a single second sheet and a receiving sheet, wherein the second sheet is laid on top of and in contact with the receiving sheet, prior to digestion.

In one embodiment, the present disclosure provides a composition comprising a multi-layered cell construct produced by two individual cell sheets according the described cell sheet harvest and transfer system, that is, a multi-layered cell construct produced with a single second sheet and a receiving sheet, wherein the second sheet is laid on top of and in contact with the receiving sheet, and wherein the second sheet has been digested.

In some embodiments, a multi-layered cell construct as disclosed herein comprises at least one of fibroblasts, smooth muscle cells and endothelial cells. In some embodiments, a multi-layered cell construct as disclosed herein comprises at least one of cardiomyocytes, endothelial cells, vascular cells, or cardiac cells. In some embodiments, a multi-layered cell construct as disclosed herein comprises at least one of fibroblasts, endothelial cells and keratinocytes.

In some embodiments, a multi-layered cell construct as disclosed herein is configured into a specific three-dimensional shape, for example, to resemble a specific tissue shape. The shape can be determined by one of ordinary skill in the art and can be configured by altering the shape of the 2D dimensions of the second substrate layers before they are added to the cells on the receiving substrate of the multi-layered cell substrate (much like the method of 3D printing as discussed previously), and/or sculpting a multi-layered cell construct into a desired 3D conformation using traditional machining techniques, which mostly rely on the removal of material by methods such as cutting or drilling (e.g., subtractive processes) using a scalpel, blade, knife or other shaping technique.

In some embodiments, a multi-layered cell construct as disclosed herein is useful in an assay, for example, to identify an agent which increases or decreases the viability of the cells within multi-layered cell construct. An assay can be any type of assay known to persons of ordinary skill in the art, for example, but not limited to, an assay to identify an agent which increases or decreases the function of the cells within multi-layered cell construct.

In some embodiments, a multi-layered cell construct as disclosed herein is a tissue-engineered blood vessel (TEBV) construct. In some embodiments, the methods as disclosed herein can be used to make a tissue-engineered blood vessel (TEBV) construct, for example, where the receiving substrate is in a cylindrical geometry, and wherein the receiving cell layer is on the outer surface of the cylinder. In some embodiments, a tissue-engineered blood vessel (TEBV) construct comprises a variety of different cell types, for example, a second cell layer and/or the receiving layer comprises at least one of fibroblasts, smooth muscle cells and endothelial cells.

Another aspect of the present disclosure relates to a method of treating a vascular disease in a subject, comprising transplanting into the subject a tissue-engineered blood vessel as disclosed herein. Another aspect of the present disclosure relates to a method of treating a subject in need thereof a skin graft, comprising transplanting into the subject a multi-layered construct produced by the methods as disclosed herein, wherein at least the second cell layer and/or the receiving layer comprises at least one of fibroblasts, endothelial cells and keratinocytes. In some embodiments, a subject in need of a skin graft is in need of wound healing, for example, where the wound is selected from the group consisting of: severe burns, field wound care, emergency wound care.

Another aspect of the present disclosure relates to a kit comprising at least the materials for generating a second substrate and a receiving substrate (e.g. either the materials to formulate the enzymatically degradable hydrogels, or the enzymatically degradable hydrogels themselves), and a first digestive enzyme for digesting the receiving substrate, and a second digestive enzyme for digesting the second substrate. In some embodiments, the kit further comprising at least one pressure plate.

Another aspect of the present disclosure relates to methods of making multi-layered cell constructs and tissue engineered blood vessels (TEBV). The tissue-engineered constructs are made by having a receiving substrate which is cylindrical in shape and wherein the receiving cell layer is on the outside of the cylindrical substrate, and wherein stacks of secondary cell layers are stacked upon the outside of the cylindrical receiving substrate on the receiving cell layer.

The multi-layered cell constructs as disclosed herein can be applied to any type of soft tissue engineering for drug testing or as replacement tissue.

In some embodiments, the methods and multi-layered cell constructs as disclosed herein can be used to generate vascular grafts, for example, intima, media, adventitia can be mimicked using three different cell types patterned cell sheet stacks (fibroblast, smooth muscle cells, and endothelial cells) that are assembled in an appropriate manner. In some embodiments, a multi-layered cell construct as a vascular graft can be referred to herein a "tissue engineered blood vessels (TEBV)" can be either a patch or tube.

In some embodiments, the methods and multi-layered cell constructs as disclosed herein can be used to generate a cardiovascular patch, comprising a highly vascularized cardiac tissue patch using repeated stacking of cardiomyocyte sheets and endothelial cell sheets, for example, for the treatment of a subject with an infracted tissue region to restore heart function.

In some embodiments, the methods and multi-layered cell constructs as disclosed herein can be used to generate a skin graft, e.g., the cell layers can be stacked to form an accurate structural and biological resemblance to skin, where the multi-layered cell construct comprises a combination of fibroblast cell sheets, and/or endothelial cell sheets, and/or keratinocyte cell sheets. Use of such a multi-layered cell substrate provides a subject in need of a skin graft significantly better options than limited auto-graft tissue or small intestine submucosa product. In some embodiments, a health care or cosmetics company may be interested in such a multi-layered skin cell construct.

In some embodiments, the methods and multi-layered cell constructs as disclosed herein can be used for emergency wound healing, for example, confluent individual cell layers/sheets (on second substrates and receiving substrates) can be achieved in a few days and multi-cell layer stacking can be achieved in a few hours. In some embodiments, a multi-layered cell construct can be used for emergency would healing applications such as severe burn treatment, field wound care, and possibly emergency wound care for astronauts.

In some embodiments, the methods and multi-layered cell constructs as disclosed herein can be mass produced. For example, large multi-layer cell constructs can be of large sizes and conformations, can be folded into or cut into any 3D shape to produce target tissue specific shape (tissue origami). In some embodiments, a machine or computerized robot can be used to stack the second cell layer (on the second substrate) onto a receiving cell layer (on the receiving substrate) for high-throughput generation of the multi-layered cell substrate as disclosed herein. Accordingly, such methods of generating the multi-layered cell construct as disclosed can be readily adapted to high throughput methods, e.g. using robotic or other automated procedures and computerized systems as disclosed herein to stack a second cell layer on the receiving cell layer, dissolve the second substrate and repeat the process until the desired number of second cell layers have been added, then dissolve the receiving substrate to produce the multi-layered cell substrate as disclosed herein. In some embodiments, the second cell layers are different 2D shapes, such that when they are stacked on other second cell layers and/or receiving layers of a different 2D shape, they from a 3D multi-layered cell construct of a specific 3D conformation much in the same way that 3D printing works.

In some embodiments, the methods and multi-layered cell constructs as disclosed herein can be used in drug testing, for example, a multi-layer cell construct closely mimics 3D native tissue structure and composition. The multi-layer cell construct would have a distinctively different response to the same drug when compared against 2D cultured cells. Therefore, drug testing could take advantage of this cell sheet harvest and transfer system to project realistic target tissue response to a new drug.

In yet another embodiment, methods of treating subjects in need of tissue or blood vessels are provided. The methods of transplanting and/or implanting the tissue sheets and blood vessels in a subject are provided.

BRIEF DESCRIPTION OF THE FIGURES

FIG. 1A shows individual CMC-ty and Al-ty cell sheet construct.

FIG. 1B shows a schematic of the stacking process; dialysis membrane was inserted between pressure plate and upside down Al-ty construct to prevent penetration of pillars into the Al-ty film.

FIG. 1C shows stacked two cell sheet constructs; top layer of cell sheet construct is Al-ty construct and bottom layer of cell sheet construct is CMC-ty construct.

FIG. 1D shows the combined layers of cell sheet constructs that are stained by Cell Tracker Green and Red respectively were stacked together with about 60° between the patterns.

FIG. 2A shows 4% CMC-ty was cast in the mold to fabricate thin film shaped CMC-ty hydrogel to be used as a backing film.

FIG. 2B shows that similar to CMC-ty film, Al-ty hydrogel (1%) was casted and further crosslinked with $CaCl_2$/$HRP$/$H_2O_2$ solution to increase rigidity as a backing film.

FIG. 3A shows a patterned (50 μm×50 μm ridge and 20 μm groove) PDMS mold.

FIG. 3B shows gelatin stamp fabrication by casting 10% gelatin solution on PDMS mold.

FIG. 3C shows CMC-ty or Al-ty was cast and gelated to fabricate topographically patterned substrate surface. After complete gelation, gelatin stamp was melted away.

FIG. 3D shows distinct patterned substrate (CMC-ty or Al-ty) surface after several rinses with warmed PBS to remove gelatin completely.

FIG. 3E shows human umbilical vein endothelial cells (HUVECs) cultured on the surface of the CMC-ty or Al-Ty hydrogel.

FIG. 3F shows mouse fibroblasts (NIH 3T3) cultured on the surface of the CMC-ty or Al-Ty hydrogel.

FIG. 3G shows cultured human mesenchymal stem cells (hMSC) at day 2 after seeding on the surface of the CMC-ty or Al-Ty hydrogel.

FIG. 3H shows hMSCs at day 7 after seeding on the surface of the CMC-ty or Al-Ty hydrogel.

FIG. 4A shows surface stiffness (Pa) measurement of CMC-ty (1%, 2%, and 4%) concentration.

FIG. 4B shows surface stiffness (Pa) measurement of Al-ty (1%, 2% and 2% with additional crosslinking by $Ca^{2+}$).

FIG. 6A shows live cell image (×20 magnification). Positive signal of white or light color indicates live cells.

FIG. 6B shows dead cell image (×20 magnification). Positive signal of white or light color indicates dead cells.

FIG. 6C shows overlapped image of FIGS. 6A and 6B (×20 magnification).

FIG. 6D shows live cell image (×5 magnification).

FIG. 6E shows dead cell image (×5 magnification).

FIG. 6F shows an overlayed image of FIGS. 6D and 6E (×5 magnification).

DETAILED DESCRIPTION OF THE DISCLOSURE

Figure 1A:
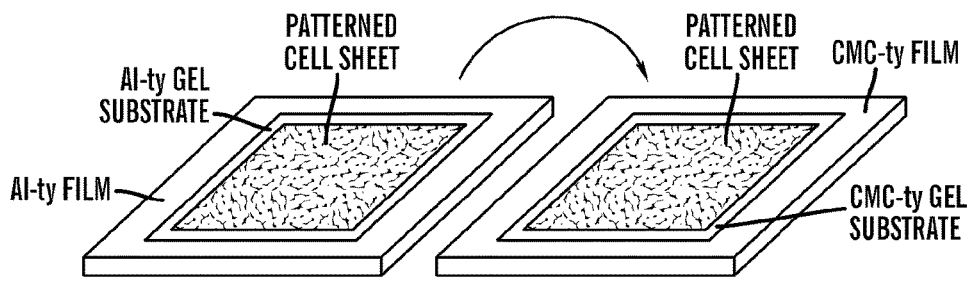
FIGS. 1A-1D show cell sheet transfer and stacking method; two patterned cell sheets grown on CMC-ty and Al-ty construct (cell sheet-substrate-backing film) respectively were used for stacking. The entire cell sheet-(Al-ty)-backing film construct was flipped over to bond two cell sheets by exerting light pressure while maintaining 60° angle between the patterns. Alginate lyase containing media used to specifically degrade top Al-ty substrate. Carboxymethyl cellulose (CMC), alginate (Al), tyramine hydrochloride (ty).
Figure 1B:
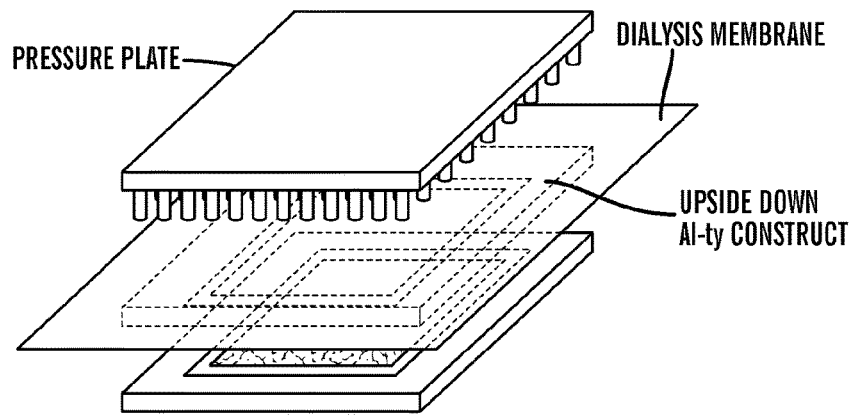
Figure 1C:
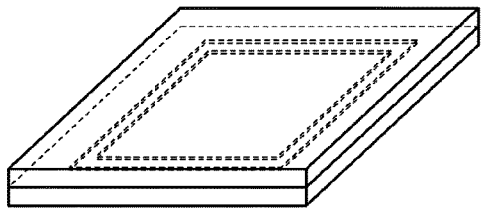
Figure 1D:
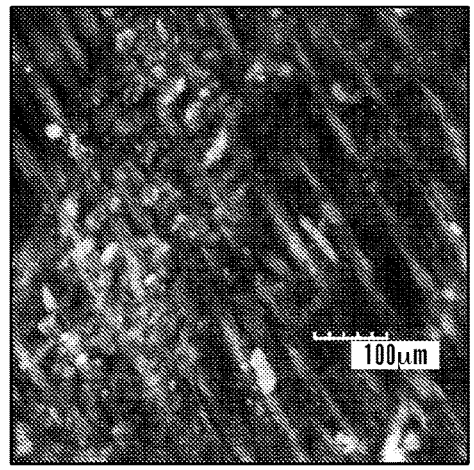

The present disclosure generally relates to compositions comprising multi-layered cell sheet stacks, and methods and systems to make such multi-layered cell sheet stacks using individual layers of cell sheets on scaffold/support materials that are digested by specific enzymes. In some embodiments, the method of making such a multi-layered cell sheet stacks comprises stacking individual layers of cell sheets, one on top of another.

The method comprises first culturing individual layers of cell sheets on scaffold/support materials that can be digested by specific enzymes, e.g., carboxymethyl cellulose (CMC) conjugated with tyramin (ty): CMC-ty; and alginate (Al) conjugated with tyramin (ty): Al-ty) that can be degraded by cellulose and alginate lyase respectively. These specific enzymes do not digest the extracellular matrices of cells. A first cell sheet layer is flipped on to a receiving cell sheet layer to form a sandwich with the first cell sheet layer being on top of the sandwich and the receiving cell sheet layer being the bottom of the sandwich. Pressure is applied to the sandwich to encourage adhesion of the layers. This is then followed by digestion of the scaffold material in the first (top) cell sheet layer. It is important that both cell sheet layers have different digestible scaffold materials so that only the scaffold material of the first cell sheet layer, i.e., the top cell sheet layer with respect to the receiving cell sheet layer, is digested away. When digestion is completed, the receiving cell sheet layer now comprises cells from the two cell sheet layers. A second cell sheet layer is flipped on to this resultant receiving cell sheet layer to form a sandwich and the process in repeated again to attain the desired layers of cell sheets in 3D.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this disclosure belongs.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "higher" are all used herein to generally mean an increase by a statically significant amount; for the avoidance of any doubt, the terms "increased", "increase" or "enhance" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

By an "increase" in the expression or activity of a gene or protein is meant a positive change in protein or polypeptide or nucleic acid level or activity in a cell, a cell extract, or a cell supernatant. For example, such a increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

As used herein, the term "gene" includes a segment of DNA that contains all the information for the regulated biosynthesis of an RNA product, including promoters, exons, introns, and other untranslated regions that control expression. Those in the art will readily recognize that nucleic acid molecules can be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference can be made to either strand and still comprise the same polymorphic site and an oligonucleotide can be designed to hybridize to either strand. Throughout this specification, in identifying a polymorphic site, reference is made to the sense strand, only for the purpose of convenience. As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyedenosine, deoxycytidine, deoxyguanosine, and deoxythymidine. For purposes of clarity, when referring herein to a nucleotide of a nucleic acid, which can be DNA or RNA, the terms "adenosine", "cytosine", "guanosine", and thymidine" are used. It is understood that if the nucleic acid is RNA, a nucleotide having a uracil base is uridine. The term "nucleotide" or nucleic acid as used herein is intended to refer to ribonucleotides, deoxyribonucleotides, acylic derivatives of nucleotides, and functional equivalents thereof, of any phosphorylation state. Functional equivalents of nucleotides are those that act as substrates for a polymerase as, for example, in an amplification method. Functional equivalents of nucleotides are also those that can be formed into a polynucleotide that retains the ability to hybridize in a sequence specific manner to a target polynucleotide. As used herein, the term "polynucleotide" includes nucleotides of any number. A polynucleotide includes a nucleic acid molecule of any number of nucleotides including single-stranded RNA, DNA or complements thereof, double-stranded DNA or RNA, and the like.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A "polymorphic gene" refers to a gene having at least one polymorphic region.

The term "genotype" refers to the specific allelic composition of an entire cell or a certain gene, whereas the term "phenotype" refers to the detectable outward manifestations of a specific genotype.

The term "variant", "variance", "mutation" or "polymorphism" are used interchangeably herein and as used herein with respect to nucleic acid sequence refers to a difference in nucleic acid sequence in the population. Polymorphisms are sometimes referred to as "single nucleotide polymorphism" or "SNP" can be synonymous or non-synonymous. Synonymous polymorphisms when present in the coding region typically do not result in an amino acid change. Non-synonymous polymorphism when present in the coding region alter one or more codons resulting in an amino acid replacement in the amino acid chain. Such mutations and polymorphisms can be either heterozygous or homozygous within an individual. Homozygous individuals have identical alleles at one or more corresponding loci on homologous chromosomes. While heterozygous individuals have two different alleles at one or more corresponding loci on homologous chromosomes. A polymorphism is thus said to be "allelic," in that, due to the existence of the polymorphism, some members of a species carry a gene with one sequence (e.g., the original or wild-type "allele"), whereas other members can have an altered sequence (e.g., the variant or, mutant "allele"). In the simplest case, only one mutated variant of the sequence can exist, and the polymorphism is said to be diallelic. For example, if the two alleles at a locus are indistinguishable in their effects on the organism, then the individual is said to be homozygous at the locus under consideration. If the two alleles at a locus are distinguishable because of their differing effects on the organism, then the individual is said to be heterozygous at the locus. In the present application, typographically, alleles are distinguished "+" or "−". Using these symbols, homozygous individuals are +/+, or −/− or two of the same symbol, for example A/A, G/G, T/T and C/C. Heterozygous individuals are +/− or two different symbols, for example A/G, A/T. A/C, G/T etc. The occurrence of alternative mutations can give rise to tri-allelic and tetra-allelic polymorphisms, etc. An allele can be referred to by the nucleotide(s) that comprise the mutation. In some instances a "silent mutation" is a synonymous codon change, or silent SNP is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers", or "di-allelic markers".

The term "expression" as used herein refers to interchangeably to the expression of a polypeptide or protein or expression of a polynucleotide or expression of a gene. Expression also refers to the expression of pre-translational modified and post-translationally modified proteins, as well as expression of pre-mRNA molecules, alternatively spliced and mature mRNA molecules. Expression of a polynucleotide can be determined, for example, by measuring the production of RNA transcript molecules, for example messenger RNA (mRNA) transcript levels. Expression of a protein or polypeptide can be determined, for example, by immunoassay using an antibody(ies) that bind with the polypeptide.

The term "encode" as it is applied to polynucleotides refers to a polynucleotide which is said to "encode" a polypeptide or protein if, in its native state or when manipulated by methods well known to those skilled in the art, it can be transcribed to produce the RNA which can be translated into an amino acid sequence to generate the polypeptide and/or a fragment thereof. The antisense strand is the complement of such a nucleic acid, and the encoding sequence can be deduced therefrom.

The term "endogenously expressed" or "endogenous expression" refers to the expression of a gene product at normal levels and under normal regulation for that cell type.

The term "interfere" or "interrupt" as disclosed herein as used in reference with a mutation or agent (e.g., test compound) which interrupts the binding of BRCA1 with phospho-ser10-topo I refers to an agent or mutation which decreases the binding affinity or binding interaction of BRCA1 with phospho-ser10-topo I by at least about 10%, or at least about 25%, or at least about 50%, or greater than 50%.

The term "entity" refers to any structural molecule or combination of molecules.

The term "drug", "agent" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "antagonist" refers to any agent or entity capable of inhibiting the expression or activity of a protein, polypeptide portion thereof, or polynucleotide. Thus, the antagonist may operate to prevent transcription, translation, post-transcriptional or post-translational processing or otherwise inhibit the activity of the protein, polypeptide or polynucleotide in any way, via either direct of indirect action. The antagonist may for example be a nucleic acid, peptide, or any other suitable chemical compound or molecule or any combination of these. Additionally, it will be understood that in indirectly impairing the activity of a protein, polypeptide of polynucleotide, the antagonist may affect the activity of the cellular molecules which may in turn act as regulators or the protein, polypeptide or polynucleotide itself. Similarly, the antagonist may affect the activity of molecules which are themselves subject to the regulation or modulation by the protein, polypeptide of polynucleotide.

The terms "patient", "subject" and "individual" are used interchangeably herein, and refer to an animal, particularly a human, to whom treatment including prophylaxic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "effective amount" includes within its meaning a sufficient amount of a pharmacological composition to provide the desired effect. For example, an effective amount using the methods as disclosed herein would be considered as the amount sufficient to reduce a symptom of a need of a tissue transplant, for example at least one symptom experienced by a subject in need of a tissue transplant by at least 10%. Further, an effective amount as used herein would also include an amount sufficient to prevent or delay the development of a symptom experienced by a subject in need of a tissue transplant, alter the course of a symptom disease (for example but not limited to, slow the progression or development of at least one symptom experienced by a subject in need of a tissue transplant), or reverse at least one symptom experienced by a subject in need of a tissue transplant.

As used herein, the term "treating" includes administering a multi-layered construct as disclosed herein to a subject to reduce at least one symptom experienced by a subject in need of a tissue transplant. In some embodiments, a reduction in at least one symptom at least one symptom experienced by a subject in need of a tissue transplant, e.g., pain due to a degenerated tissue, improved heart function in a subject in need of a cardiac patch or suffered myocardial infarction or a by at least 10% would also be considered as affective treatments by the methods as disclosed herein.

The term "polynucleotide" as used herein, refers to single- or double-stranded polymer of deoxyribonucleotide, ribonucleotide bases or known analogies of natural nucleotides, or mixtures thereof. The term includes reference to the specified sequence as well as to the sequence complementary thereto, unless otherwise indicated.

The term "polypeptide" means a polymer made up of amino acids linked together by peptide bonds. The terms "polypeptide" and "protein" are used interchangeably herein, although for the purposes for the present disclosure, a polypeptide may constitute a portion or the full length protein.

The term "expression" as used herein refers to interchangeably to the expression of a polypeptide or protein and expression of a polynucleotide or gene. Expression of a polynucleotide may be determined, for example, by measuring the production of messenger RNA (mRNA) transcript levels. Expression of a protein or polypeptide may be determined, for example, by immunoassay using an antibody(ies) that bind with the polypeptide.

The term "endogenously expressed" or "endogenous expression" as used herein, refers to the expression of a gene product at normal levels and under normal regulation for that cell type.

In the context of this specification, the term "activity" as it pertains to a protein, polypeptide or polynucleotide means any cellular function, action, effect of influence exerted by the protein, polypeptide or polynucleotide, either by nucleic acid sequence or fragment thereof, or by the protein or polypeptide itself or any fragment thereof.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

The term "RNAi" as used herein refers to RNA interference (RNAi) a RNA-based molecule that inhibits gene expression. RNAi refers to a means of selective post-transcriptional gene silencing by destruction of specific mRNA by small interfering RNA molecules (siRNA). The siRNA is typically generated by cleavage of double stranded RNA, where one strand is identical to the message to be inactivated. As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of downstream processing of the RNA (i.e. although siRNAs are believed to have a specific method of in vivo processing resulting in the cleavage of mRNA, such sequences can be incorporated into the vectors in the context of the flanking sequences described herein).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example where a target gene is for example DNA-PK. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

The term "standard deviation" is a measure of the dispersion of a set of data from its mean. The more spread apart the data, the higher the deviation. Standard deviation is calculated as the square root of variance and can be calculated by one of ordinary skill in the art.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. The appropriate cell culture media, for a particular cell type, is known to those skilled in the art.

The term "drug screening" as used herein refers to the use of multi-layered cell construct as disclosed herein in the laboratory to identify drugs with a specific function. In some embodiments, the present disclosure provides drug screening methods of to identify compounds or drugs which the function of the cells and/or reduce the viability of cells in the multi-layered cell construct. In alternative embodiments, the present disclosure provides drug screening on cells present in the multi-layered cell construct to identify compounds or drugs useful as therapies for diseases or illnesses (e.g. human diseases or illnesses).

As used herein, the terms "administering," and "introducing" are used interchangeably, and refer to the placement of the multi-layered cell construct as disclosed herein into a subject by a method or route which results in at least partial localization of the multi-layered cell construct at a desired site. The multi-layered cell construct of the present disclosure can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the central nervous system, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, or be biologically inert.

The term "agent" refers to any entity which is normally not present or not present at the levels being administered in the cell. Agent may be selected from a group comprising, for example chemicals; small molecules; nucleic acid sequences; nucleic acid analogues; proteins; peptides; peptidomimetics, aptamers; antibodies; or fragments thereof. A nucleic acid sequence may be RNA or DNA, and may be single or double stranded, and can be selected from a group comprising; nucleic acid encoding a protein of interest, oligonucleotides, antisense oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), short-temporal RNAi (stRNA), dsRNA antisense oligonucleotides etc. A chemical entity or biological product is preferably, but not necessarily a low molecular weight compound, but may also be a larger compound, or any organic or inorganic molecule, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds. Agents can be, without limitation an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. The agent may be applied to the media, where it contacts the ovarian cell and induces its effects. Alternatively, the agent may be intracellular within the cell as a result of introduction of the nucleic acid sequence into the cell and its transcription resulting in the production of the nucleic acid and/or protein agent within an ovarian cancer cell.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "enriching" is used synonymously with "isolating" cells, means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not cardiovascular stem cells or cardiovascular stem cell progeny of the disclosure.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" is used interchangeably herein with "program" and refers to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

The term "proteomics" may refer to the study of the expression, structure, and function of proteins within cells, including the way they work and interact with each other, providing different information than genomic analysis of gene expression.

As used herein the term "comprising" or "comprises" is used in reference to compositions, methods, and respective component(s) thereof, that are essential to the disclosure, yet open to the inclusion of unspecified elements, whether essential or not. Accordingly, compositions or methods "comprising" one or more recited elements may include other elements not specifically recited. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Thus, the use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean ±1%. The present disclosure is further explained in detail by the following, including the Examples, but the scope of the disclosure should not be limited thereto.

It is understood that the foregoing detailed description and the following examples are illustrative only and are not to be taken as limitations upon the scope of the disclosure. Various changes and modifications to the disclosed embodiments, which will be apparent to those of skill in the art, may be made without departing from the spirit and scope of the present disclosure. Further, all patents, patent applications, and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

Method of Constructing a Multi-Layered Substrate

As discussed herein, the present disclosure relates to compositions comprising multi-layered cell sheet stacks, and methods to make such multi-layered cell sheet stacks that closely mimic the 3D native tissue structure and composition.

In some embodiments, the method of making such a multi-layered cell sheet stacks comprises stacking individual layers of cell sheets, one on top of another.

In one embodiment, the present disclosure provides a composition comprising a multi-layered cell construct produced by two individual cell sheets according the described method, that is, a multi-layered cell construct produced with a single second cell sheet/layer and a receiving cell sheet/layer, wherein the second cell sheet/layer is laid on top of and in contact with the receiving cell sheet/layer, prior to digestion.

In one embodiment, the present disclosure provides a composition comprising a multi-layered cell construct produced by two individual cell sheets according the described cell sheet harvest and transfer method, that is, a multi-layered cell construct produced with a single second cell sheet/layer and a receiving cell sheet/layer, wherein the second cell sheet/layer is laid on top of and in contact with the receiving cell sheet/layer, and wherein the second cell sheet/layer is digested as described herein.

In some embodiments, the method comprises first culturing individual layers of cell sheets on scaffold/support materials that can be digested by specific enzymes, e.g., carboxymethyl cellulose (CMC) conjugated with tyramin (ty): CMC-ty; and alginate (Al) conjugated with tyramin (ty): Al-ty) that can be degraded by cellulose and alginate lyase respectively. These specific enzymes do not digest the extracellular matrices of cells.

A first cell sheet layer (also referred to a "second cell layer") is flipped on to a receiving cell sheet layer to form a sandwich with the first cell sheet and the receiving cell sheet layer being sandwiched between the second substrate (which has the first cell sheet attached) and the receiving substrate (which has the receiving cell layer attached). Pressure is applied to the sandwich to encourage adhesion of the layers (e.g., the first cell sheet and the receiving cell sheet). This is then followed by digestion of the scaffold material of the second substrate which has attached the first cell sheet layer. It is important that both substrates (e.g., the second substrate and the receiving substrate) have different digestible scaffold materials so that only the scaffold material of the first cell sheet layer, (i.e., the second substrate) is digested away with respect to the substrate which comprises the receiving cell sheet layer. When digestion of the second substrate is completed, the receiving cell sheet layer now comprises cells from the two cell sheet layers (e.g., it comprises both the first cell sheet layer and the receiving sheet layer). A second cell sheet layer (e.g., attached to a second substrate) is flipped on to this resultant receiving cell sheet layer to form a sandwich and the process in repeated again to attain the desired layers of cell sheets in 3D.

In some embodiments, the cell layers/sheets comprises substrate CMC-ty at varying concentration. For example, 0.5%-15% by weight/volume. In other embodiments, the cell layers/sheets comprises substrate Al-ty at varying concentration. For example, 0.5%-15% by weight/volume.

In one embodiment, the cell layers/sheets described herein are non-patterned or patterned. For example, non-patterned cell layers/sheets are uniform in thickness throughout the layer or sheet, whereas patterned or micro-patterned cell layers/sheets are not uniform throughout the layer/sheet but have contours or patterns and varying thickness throughout the layer/sheet.

In one embodiment, the multi-layered cell construct produced or made by method described herein consisting essentially of two cell layers, e.g., the second cell layer laid upon the receiving cell layer. In other embodiments, the multi-layered cell construct produced or made by method described herein consisting essentially of three cell layers, four cell layers, five cell layers, six cell layers, seven cell layers, eight cell layers, nine cell layers, ten cell layers, 11 cell layers, 12 cell layers, 13 cell layers, 14 cell layers, 15 cell layers, 16 cell layers, 17 cell layers, 18 cell layers, 19 cell layers, 20 cell layers, 21 cell layers, 22 cell layers, 23 cell layers, 24 cell layers, 25 cell layers, 26 cell layers, 27 cell layers, 28 cell layers, 29 cell layers, or 30 cell layers.

In one embodiment, the present disclosure provides a composition comprising a multi-layered cell construct produced according the described cell sheet harvest and transfer method, wherein the multi-layered cell construct produced or made by method described herein consisting essentially of three cell layers, four cell layers, five cell layers, six cell layers, seven cell layers, eight cell layers, nine cell layers, ten cell layers, 11 cell layers, 12 cell layers, 13 cell layers, 14 cell layers, 15 cell layers, 16 cell layers, 17 cell layers, 18 cell layers, 19 cell layers, 20 cell layers, 21 cell layers, 22 cell layers, 23 cell layers, 24 cell layers, 25 cell layers, 26 cell layers, 27 cell layers, 28 cell layers, 29 cell layers, or 30 cell layers.

In one embodiment, the multi-layered cell construct produced or made by method described herein consisting of two cell layers, e.g., the second cell layer laid upon the receiving cell layer. In other embodiments, the multi-layered cell construct produced or made by method described herein consisting of three cell layers, four cell layers, five cell layers, six cell layers, seven cell layers, eight cell layers, nine cell layers, ten cell layers, 11 cell layers, 12 cell layers, 13 cell layers, 14 cell layers, 15 cell layers, 16 cell layers, 17 cell layers, 18 cell layers, 19 cell layers, 20 cell layers, 21 cell layers, 22 cell layers, 23 cell layers, 24 cell layers, 25 cell layers, 26 cell layers, 27 cell layers, 28 cell layers, 29 cell layers, or 30 cell layers.

In one embodiment, the present disclosure provides a composition comprising a multi-layered cell construct produced according the described cell sheet harvest and transfer method, wherein the multi-layered cell construct produced or made by method described herein consisting of three cell layers, four cell layers, five cell layers, six cell layers, seven cell layers, eight cell layers, nine cell layers, ten cell layers, 11 cell layers, 12 cell layers, 13 cell layers, 14 cell layers, 15 cell layers, 16 cell layers, 17 cell layers, 18 cell layers, 19 cell layers, 20 cell layers, 21 cell layers, 22 cell layers, 23 cell layers, 24 cell layers, 25 cell layers, 26 cell layers, 27 cell layers, 28 cell layers, 29 cell layers, or 30 cell layers.

In one embodiment, the multi-layered cell construct produced or made by method described herein comprises at least two cell layers, e.g., the second cell layer laid upon the receiving cell layer. In other embodiments, the multi-layered cell construct produced or made by method described herein comprises three cell layers, four cell layers, five cell layers, six cell layers, seven cell layers, eight cell layers, nine cell layers, ten cell layers, 11 cell layers, 12 cell layers, 13 cell layers, 14 cell layers, 15 cell layers, 16 cell layers, 17 cell layers, 18 cell layers, 19 cell layers, 20 cell layers, 21 cell layers, 22 cell layers, 23 cell layers, 24 cell layers, 25 cell layers, 26 cell layers, 27 cell layers, 28 cell layers, 29 cell layers, or 30 cell layers.

In one embodiment, the present disclosure provides a composition comprising a multi-layered cell construct produced according the described cell sheet harvest and transfer method, wherein the multi-layered cell construct produced or made by method described herein comprises three cell layers, four cell layers, five cell layers, six cell layers, seven cell layers, eight cell layers, nine cell layers, ten cell layers, 11 cell layers, 12 cell layers, 13 cell layers, 14 cell layers, 15 cell layers, 16 cell layers, 17 cell layers, 18 cell layers, 19 cell layers, 20 cell layers, 21 cell layers, 22 cell layers, 23 cell layers, 24 cell layers, 25 cell layers, 26 cell layers, 27 cell layers, 28 cell layers, 29 cell layers, or 30 cell layers.

The cell layers/sheets may be used to make the multi-layered cell constructs by stacking a plurality of the second cell layers onto receiving cell layers. Every time a second cell layer is stacked on the receiving cell layer, the second cell layer becomes the receiving cell layer for the next second cell layer which is stacked, thus resulting in a plurality of second cell layers stacked on top of each other on top of a first receiving cell layer. Suitably the second cell layers/sheets are stacked with the cells oriented in the same direction as the receiving cell layer/sheet to form multiple layers of cell sheets. In some embodiments, at least 2, at least 3, at least 4, at least 5, at least 6, at least 7, at least 8, at least 9, at least at least 10, at least 11, or at least 12 cell sheets are stacked to form a multi-layered cell construct. In some embodiments, not more than 15, not more than 16, not more than 17, not more than 18, not more than 19, not more than 20, not more than 21, not more than 22, not more than 23, not more than 24, not more than 25, not more than 26, not more than 27, not more than 28, not more than 29 or not more than 30 second cell layers/sheets are stacked to form a multi-layered cell construct. In some embodiments, a multi-layered cell construct is typically cultured for at least 2 weeks in low oxygen to allow the cell sheets to form a tissue sheet. The resulting multi-layered cell construct may be made in any size or configuration desired. For example, a multi-layered cell construct could be 1 cm x1 cm to 20 cm×20 cm.

In order to create three dimensional tissues over the length scale of diffusion limit, vascularization is required to deliver nutrition and oxygen. Using the system, methods and compositions as disclosed herein, it is easy to replicate 2D natural vascular network pattern like embedded channels on 2D surface. Since ECs known to form tube by self-assemble in a specific length scale channel, it would be feasible to create a pre-formed endothelial tube network embedded cell sheet which could be inserted between two cell sheets to build vascularized thick tissues. Numerous fields in biology or medicine could benefits from the methods, systems, assays and compositions as disclosed herein, including but not limited to, for example; drug testing, tissue engineering, and cancer studies.

Accordingly, the multi-layered cell constructs comprises at least one of the following type of cells: endothelial cells, smooth muscle cells, endothelial progenitor cells and mesenchymal stem or progenitor cells, in order to facilitate vascularization of the construct. In one embodiment, these cells are in the cell sheet layers that are incorporated into the construct.

In one embodiment, in order to facilitate vascularization of the construct, every second or third cycle of a second cell layer to be placed on the receiving layer comprises at least endothelial cells.

In another embodiment, every second or third cycle of a second cell layer to be placed on the receiving layer comprises at least endothelial cells and smooth muscle cells.

In another embodiment, every second or third cycle of a second cell layer to be placed on the receiving layer comprises at least endothelial progenitor cells and mesenchymal stem or progenitor cells.

In another embodiment, every second or third cycle of a second cell layer to be placed on the receiving layer comprises at least one of the following type of cells: endothelial cells, smooth muscle cells, endothelial progenitor cells and mesenchymal stem or progenitor cells.

It is contemplated that the cell sheet with endothelial cells and smooth muscle cells would promote the formation of blood vessels within the multi-layer cell construct thus formed and enable vascularization of the construct when implanted into the patient in need thereof.

In one embodiment where the cell sheet comprise at least one of the following type of cells: endothelial cells, smooth muscle cells, endothelial progenitor cells and mesenchymal stem or progenitor cells, the cell sheet also comprise vascular endothelial growth factor (VEGF).

In one embodiment of any multi-layered cell constructs described herein, at least one of the cell sheet layers comprising the construct comprises growth factors that promote vascularization.

Alternatively, the cell layers/sheets may be used to form tissue-engineered blood vessels (TEBV) by wrapping a multi-layered cell construct around a mandrel to form a tube. In alternative embodiments, the receiving substrate is cylindrical and the receiving cell layer is on the outside of the cylinder and is used as the surface to which a second cell layer is attached and adhered to. Suitably at least 2, at least 3, at least 4, at least 5, at least 6, at least 7, at least 8, at least 9, at least at least 10, at least 11, or at least 12 second cell layers/sheets are wrapped around the receiving cell layer and cylindrical substrate to form a TEBV. Suitably not more than 15, not more than 16, not more than 17, not more than 18, not more than 19, not more than 20, not more than 21, not more than 22, not more than 23, not more than 24, not more than 25, not more than 26, not more than 27, not more than 28, not more than 29 or not more than 30 second cell layers/sheets are wrapped around the receiving cell layer and cylindrical substrate to form a TEBV. The cylindrical substrate of the receiving substrate may be any suitable diameter such that the inner diameter of the resulting TEBV may be between about 0.5 mm and about 6 mm. For example, TEBV with inner diameters of at least about 0.5 mm, 0.75 mm, 0.9 mm, 1 mm, 1.5 mm, 2 mm, 3 mm, 4 mm, 5 mm or 6 mm may be useful in various applications. Those of skill in the art will appreciate that the required inner diameter of the TEBV will be determined based upon the end use in a subject. In some embodiments, the receiving substrate is enzymatically digested as soon as the desired thickness of the TEBV is established (buy a plurality of secondary cell layers). In alternative embodiments, the cylindrical multi-layered cell substrate is then cultured for at least one week, suitably two weeks prior to contacting with the first enzymes to digest the receiving substrate to form the TEBV.

In some embodiments, a multi-layered cell construct and/or a TEBV is cultured and/or matured in a bioreactor for up to 2 months. A multi-layered cell construct and/or TEBV are easily handled and can be sutured into place in a subject readily. In addition, a multi-layered cell construct and/or a TEBV can be attached to a bioreactor and used in perfusion flow experiments with high pressure flow conditions.

Enzymatically Degradable Substrates

In some embodiments, the second and receiving substrates uses natural polymer hydrogels (carboxymethyl cellulose (CMC) and alginate (Al)) with matching degrading enzyme—cellulose and alginate lyase, respectively. These natural, enzymatically digestible polymer hydrogels are much cheaper than thermoresponsive polymers, (e.g., nisopropylacrylamide as used by UpCell) in respect to produce the same dimension cell sheet.

The term "substrate" should be understood in this connection to mean any suitable carrier material to which the cells are able to attach themselves or adhere in order to form the corresponding cell composite, e.g. the multi-layered cell construct as disclosed herein. For example, a substrate (also referred to as a "biocompatible substrate") is a material that is suitable onto which a cell population can be deposited. A biocompatible substrate does not cause toxic or injurious effects to a subject or once implanted in the subject. In one embodiment, the biocompatible substrate is a polymer with a surface that can be shaped into the desired structure that promotes cell-cell interaction. The polymer can also be shaped into a part of a structure that requires repairing or replacing. The biocompatible substrate provides the supportive framework that allows cells to attach to it, and grow on it. Cultured populations of cells can then be grown on the biocompatible substrate, which provides the appropriate interstitial distances required for cell-cell interaction.

In some embodiments, a second substrate and/or a receiving substrate can be an enzymatically degradable hydrogels, where the enzymatically degradable hydrogels incorporate an enzyme-susceptible peptide that holds together the hydrogel structure. Enzymatically degradable hydrogels include, but are not limited to polyethylene glycol (PEG) gels with a wide range of enzymatically degradable peptides or amino acid sequences attached that can be degraded by matrix metalloproteinases (MMPs), elastases and plasmin. In some embodiments, the hydrogel is a PEG-succinimidyl propionate hydrogel with attached amino acid sequences, e.g., but not limited to a PEG-amine functionalized with a synthetic tetrapeptide Ala-Pro-Gly-Leu (4armPEG10k-LGPA), where the collagenase sensitive peptide sequence Ala-Pro-Gly-Leu allows for enzymatic degradation (see Brandi et al., Biomaterials, 31, 2010., 3957-3966). In some embodiments, a PEG hydrogel is an amine-reactive PEG-monoacrylate with a collagenase sensitive peptide (Gly-Gly-Leu'Gly-Pro-Ala-Gly-Gly-Lys) peptide attached, or a integrin-binding domain peptide (Tyr-Ile-Shy-Ser-Arg) attached. In some embodiments, a biodegradable hydrogel can be systhesized by the click reaction of 4arm azido-terminated PEG and two alkenye-terminated peptides; [alkyne]-GFLGK-alkyne] (GFLG1) and ([alkyne-GFLG)2K (GFLG2), as disclosed in Yang et al., Synthesis and Characterization of enzymatically degradable PEG-based peptide containing hydrogels" Macromol. Biosci., 2010, 10; 445-454, which is incorporated herein in its entirety.

Hydrogels can be formed from synthetic (e.g., poly(ethylene glycol), poly (hydroxyethyl methacrylate)) and naturally occurring polymers (e.g., collagen, hyaluronan, heparin), and are useful 3D models of tissue culture due to their high water content and ability to form in the presence of cells, proteins and DNA. Depending on the reactivity of the constituent materials, gelation can be induced using pH, temperature, coulombic interactions, covalent bonding, non-covalent interactions, or polymerization.

PEG

Poly(ethylene glycol) is a hydrophilic polymer that, when cross-linked into networks, can have a high water content. PEG is a suitable material for biological applications because it does not generally elicit an immune response. Since the 1970s, PEG has been used to modify therapeutic proteins and peptides to increase their solubility, lower their toxicity and to prolong their circulation half-life. PEG hydrogels are chemically well-defined, and multiple chemistries can be used both for their formation and chemical modification.

PEG Macromers

PEG is easily synthesized by the living anionic ring-opening polymerization of ethylene oxide; well-defined (low polydispersity) PEGs with a range of molecular weights and a variety of end groups (e.g., alcohol, methyl ether, amine, N-hydroxysuccinimidyl (NHS) ester) are widely available.

In order to form a hydrogel, PEG must be cross-linked. Initially, PEG was cross-linked non-specifically using ionizing radiation. 8 PEG hydrogels are now typically synthesized via covalent cross-linking of PEG macromers with reactive chain ends.

PEG macromers with reactive chain ends such as acrylate, methacrylate, allyl ether, maleimide, vinyl sulfone, NHS ester and vinyl ether groups are easily synthesized from readily available starting materials. The alcohol chain ends of PEG can be esterified using acid chlorides (e.g., acryloyl chloride, methacryloyl chloride) in the presence of base. PEG chain ends can be etherified under basic conditions by reaction with alkyl halides such as 2-chloroethyl vinyl ether or allyl bromide. PEG divinyl sulfone is prepared by coupling PEG to a large excess of divinyl sulfone or by a multistep process to prepare chloroethyl sulfone chain ends that undergo basic elimination to form vinyl sulfone groups.

Enzymatic Degradation of PEG-Based Hydrogels

Although ester linkages are enzymatically degradable, most researchers utilize sequence-specific enzymatic degradation of peptides incorporated into hydrogels rather than non-specific enzymatic degradation of esters and amides. In some embodiments, incorporating matrix metalloproteinase (MMP) sensitive linkages into hydrogels via addition of cysteine-functionalized peptides across acrylates, maleimides and vinyl sulfones. MMP-degradable linkages have also been used to tether therapeutic agents into hydrogels. For example, growth factors such as vascular endothelial growth factor (VEG-F) can be released via enzymatic degradation of an MMP-sensitive tether to induce angiogenesis In both hydrolysis and enzymolysis, the rate of degradation is predetermined by the chemistry of the macromer. In hydrolysis, the degradation rate of the material is pre-engineered through the identity (e.g., hydrophobicity or hydrophilicity) and number of the hydrolysable groups, and cannot be changed once the material is fabricated. In enzymolysis, the degradation typically occurs in an area local to the cells producing the enzyme. While hydrolysis and enzymolysis are both effective methods for sustained hydrogel degradation and sustained release of therapeutic agents, the rate of release cannot be adjusted or arrested after the hydrogel is fabricated, and release is not spatially controlled.

Hydrogels can be designed to be susceptible to degradation by the proteases used by cells to remodel their surroundings; specifically, peptides that may be cleaved by cell-produced proteases are incorporated into the hydrogel crosslinks. A wide range of sequences can be used that are degraded by matrix metalloproteinases (MMPs), elastases and plasmin. The general susceptibility to proteases is controlled by the specific peptide sequence and there are a plethora of sequences that could be used to tailor the specific cell-mediated degradation of hydrogels (see Budick et al., Moving from static to dynamic complexity in hydrogel design. Nat. Commun 2012, 3:1269 (2012).) Generally, the hydrogels are formed by reacting a multifunctional polymer (for example, PEG macromers with vinyl sulphones or acrylates) with end groups of proteasesensitive peptides (for example, thiols from cysteine moieties), where cells and molecules can be encapsulated during gelation. The degradation rates of hydrogels where both sequences for adhesion and degradation are present is controlled by crosslink density and peptide specificity. Hybrid systems of synthetic and biological polymers including PEG fibrinogen and hyaluronic acid can be used as enzymatically degradable hydrogels for use in the substrates as disclosed herein.

To render a hybrid polymer/hydrogel degradable, the structure of the degradable sequences should match the active site of respective enzyme(s); oligopeptide sequences have been frequently used as degradable crosslinks in hydrogels. Hydrogels, containing oligopeptide crosslinks susceptible to chymotrypsin-catalyzed hydrolysis were synthesized by crosslinking N-(2-hydroxypropyl)methacrylamide (HPMA) copolymers containing reactive side-chains (terminated np-nitrophenoxy groups) with oligopeptide-containing diamines The degradability of hydrogels was dependent on the length and detailed structure of the oligopeptide sequence and on the equilibrium degree of swelling (network density); the higher the degree of swelling, the faster the rate of degradation. The degree of swelling also has an impact on surface versus bulk degradation of the hydrogel. If the enzyme cannot diffuse into the hydrogel interior, only surface degradation takes place. Similar HPMA-based hydrogels degradable by cathepsin B, a lysosomal thiol proteinase can also be used In further experiments, HPMA-based hydrogels with degradable crosslinks were shown to release FITC-dextran and daunomycin (covalently bound via oligopeptide spacer) during incubation with a mixture of lysosomal enzymes (Tritosomes) or chymotrypsin.

In some embodiments, acrylamide-based hydrogels containing oligopeptides degradable by chymotrypsin are encompassed for use in the methods, systems and compositions as disclosed herein.

In some embodiments, these hydrogel polymers can be either in linear form or branched form, and include in their structure, but are not limited to, other poly(alkylene glycol), such as poly(propylene glycol), copolymers of ethylene glycol and propylene glycol and the like, poly(oxyethylated polyol), poly(olefinic alcohol), poly(vinylpyrrolidone), poly (hydroxypropylmethacrylamide), poly($\alpha$-hydroxy acid), poly(vinyl alcohol), poly-phosphazenes, polyoxazolines; polymers and copolymers (whether random, block, segmented or grafted) of lactones such as ε-caprolactone, glycolide, L-lactide, D-lactide, meso-lactide, 1,4-dioxan-2-one, trimethylene carbonate (1,3-dioxan-2-one), χ-butyrolactone, δ-valerolactone, 1,5-dioxepan-2-one, 1,4-dioxepan-2-one, 3-methyl-1,4-dioxan-2,5-dione, 3,3 diethyl-1,4-dioxan-2,5-one, ε-decalactone, pivalolactone and 4,4-dimethyl-1,3-dioxan-2-one and the like; several embodiments of such copolymers have been described by, among others, U.S. Pat. Nos. 5,951,997, 5,854,383 and U.S. Pat. No. 5,703,200 and shall be considered as being within the scope of the present disclosure; hydroxy-terminated polyorthoesters obtainable for instance by the addition reaction of a diol (e.g. an alkylenediol such as ethylenediol, trimethyleneglycol, tetramethyleneglycol, pentamethyleneglycol, hexanediol-1,6 and the like, or a cycloalkyldiol such as 1,4-cyclohexanedimethanol or 1,4-cyclohexanediol) or polyethyleneglycol onto a diketene acetal; such a method for a hydroxy-terminated polyorthoester is well known in the art and is described, starting from 3,9-bis(ethylidene-2, 4,8,10-tetraoxaspiro[5,5]undecane, by J. Heller et al. in Macromolecular Synthesis 11: 23-25; Hydroxy-terminated polyacetals obtainable for instance by the condensation reaction of at least a diol (such as hereinabove mentioned) and a divinylether as is well known in the art; for instance, U.S. Pat. No. 4,713,441 describes unsaturated, linear, water-soluble polyacetals having molecular weights from about 5,000 to about 30,000 which may be formed by condensing a divinylether, a water-soluble polyglycol and a diol having a (preferably pendant) unsaturation, which may be further converted to hydrogels, for instance by using a free-radical initiator in order to copolymerize the double bonds in the polyacetal with a monomeric compound having a reactive double bond. Another typical procedure for this kind of polyacetals may be found in Heller et al., Journal of Polym. Science, Polym. Letters Edition (1980) 18:293-7, starting from 1,4-divinyloxybutane or diethyleneglycol divinylether. French patent No. 2,336,936 further refers to crosslinked polyacetals formed by condensing diols or polyols with 3,4-dihydro-2H-pyran-2-ylmethyl-3,4-dihydro-2H-pyran-2-ylcarboxylate which may also be used in the present disclosure.

Additionally, the enzymatically digestible polymer hydrogels as disclosed herein can be topographically patterned, thus providing a simple and high cell viability transfer process and manufacturer of multi-layered cell substrates for use in many biomedical applications such as cardiac patches, vascular grafts, and skin grafts as well as an in vitro model 3D system for drug testing. Moreover, enzymatically digestible polymer hydrogels can be scaled-up to lower the production costs of the multi-layered cell constructs and engineered tissue.

Additionally, enzymatically digestible polymer hydrogels have the capacity for tuning the substrate stiffness to match the specific cell type attached. In some embodiments, the second substrate and/or the receiving substrates have a predetermined substrate stiffness to maintain the cell-specific characteristics of the cells in the cell layer on the substrate. In some instances, the stiffness or rigidity of the second and/or receiving substrate is tunable, and can be customized or tailored to a specific cell type to provide close mimicry of the natural target cell mechanical growth environment.

In some embodiments, the stiffness, herein also referred to "modulus" of the substrate can be varied to correspond to a range of modulus specific for each tissue type such as bone, brain, cartilage, artery, and skeletal muscle. For example, but without limitation, the substrate can be configured for a modulus suitable for neurons and/or brain tissue, which is one of the softest tissues in the body (e.g., having an elastic modulus (E)=0.5-1 kPa)). In some embodiments, a substrate can be configured with a modulus suitable for muscle tissue (e.g., myocytes or cardiomyocytes) were skeletal muscle has a modulus of E~10 kPa. In some embodiments, a substrate can be configured with a modulus suitable for cartilage cells, where cartilage tissue has a modulus of E~500 kPa. In some embodiments, a substrate can be configured with a modulus suitable for osteoclasts and osteoblasts, or for other bone tissue, where cortical bone ha a modulus of E~15×10$^6$ kPa.

The stiffness or modulus of a substrate can be controlled and modulated by any means commonly known by one of ordinary skill in the art. In some embodiments, the concentration of the polymer solution (which becomes the hydrogel when it gelated) can define the substrates modulus. For example, the higher concentration the polymer solution, the higher modulus the hydrogel yields. In some embodiments, the modulus can be varied by increasing the degree of crosslinking. For example, the hydrogel materials as disclosed herein (e.g., CMC-ty and Al-ty) have tyramin branches on either the CMC or Alginate backbone. The conjugated tyramines are the crosslinkers, and therefore, when more tyramines are incorporated per CMC or Alginate backbone, the modulus will increase for a given polymer concentration. Furthermore, one can add secondary cross-linking as an alternative or additional method to increase the modulus of a substrate. For example, Al-ty can be gelated using horse radish peroxidase (HRP), and/or be gelated by incorporation of cations ($Ca^{2+}$ or $Mg^{2+}$). The inventors herein have demonstrated use of both HRP-driven and $Ca^{2+}$-driven gelation simultaneously in a 2% Al-ty gel to increase the modulus two-fold as compared to 2% Al-ty gelated using only HRP-driven gelation. Therefore, one of ordinary skill in the art can control the substrate modulus from very low to very high values in the range of 100 Pa to 50 KPa, which covers most of the soft tissue elastic modulus range. Table 1 shows the stiffness preference for growing or for differentiating different cell types on cell sheets made of different substrate. Table 2 summarizes the elastic moduli of several different tissues. Table 3 shows the comparison of cell responses to hydrogels with variable stiffness.

In some embodiments, the scaffold for use in the methods and compositions as disclosed herein can also be coated with, or combined with biostatic or biocidal agents. Suitable biostatic/biocidal agents include for example, but not limited to antibiotics, povidone, sugars, mucopolysaccharides, chlorobutanol, quarternary ammonium compounds such as benzalkonium chloride, organic mercurials, parahydroxy benzoates, aromatic alcohols, halogenated phenols, sorbic acid, benzoic acid, dioxin, EDTA, BHT, BHA, TBHQ, gallate esters, NDGA, tocopherols, gum guaiac, lecithin, boric acid, citric acid, p-Hydroxy benzoic acid esters, propionates, Sulfur dioxide and sulfites, nitrates and nitrites of Potassium and Sodium, diethyl pyrocarbonate, Sodium diacetate, diphenyl, hexamethylene tetramine o-phenyl phenol, and Sodium o-phenylphenoxide, etc. When employed, biostatic/biocidal agent will typically represent from about 1 to about 25 weight percent of the substrate, calculated prior to forming the shaped material. In some embodiments, the biostatic/biocidal agents are antibiotic drugs.

In some embodiments, the scaffold for use in the methods and compositions as disclosed herein is pretreated prior to seeding with the cells in order to enhance the attachment of cells to the scaffold substrate. For example, prior to seeding with cells, the scaffold substrate can be treated with, for example, but not limited to, 0.1M acetic acid and incubated in polylysine, polylysine, PBS, collagen, poly-laminin and other cell adhesive substances known to persons skilled in the art.

Suitable surface active agents include the biocompatible nonionic, cationic, anionic and amphoteric surfactants and mixtures thereof. When employed, surface active agent will typically represent from about 1 to about 20 weight percent of the substrate, calculated prior to forming the shaped material. It will be understood by those skilled in the art that the foregoing list of optional substances is not intended to be exhaustive and that other materials can be admixed with substrate within the practice of the present disclosure.

Suitable surface active agents include medically/surgically useful substances, such as, for example but not limited to bioactive substances which can be readily combined with the cell coated substrate of this disclosure and cell adhesion molecules, and include but are not limited to, e.g., demineralized bone powder as described in U.S. Pat. No. 5,073,373 the contents of which are incorporated herein by reference; collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interlenkins, e.g., interleukin-1 (IL-1), interleukin-2 (IL-2); human alpha thrombin; transforming growth factor (TGF-beta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digestors; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added substances can vary widely with optimum levels being readily determined in a specific case by routine experimentation. In some embodiments, an enzymatically degradable hydrogel as disclosed herein may also comprise an adhesion peptide, for example, but not limited to, an adhesion peptide HO-Arg-Ser-Gly-Ile-Try or an adhesion-binding motif Tyr-Ile-Gly-Ser-Arg, a laminin fragment Cys-Asp-Pro-Gly-Tyr-Ile-Gly-Ser-Arg (YIGSR) to promote or mediate cell adhesion to the polymer hydrogel.

It will be understood by those skilled in the art that the foregoing list of medically/surgically useful agents and substances is not intended to be exhaustive and that other useful substances can be admixed with substrate and/or the cell coated substrate within the practice of the present disclosure.

The total amount of such optionally added medically/surgically useful agents and substances will typically range from about 0 to about 95, or about 1 to about 60, or about 1 to about 40 weight percent based on the weight of the entire composition prior to compression of the composition, with optimal levels being readily determined in a specific case by routine experimentation. In some embodiments, a medically/surgically useful substance is bone morphogenic proteins.

In some embodiments, the scaffold is sterilized prior to or after the seeding the cells. General sterilization methods can be used, for example, but not limited to ethylene oxide or irradiating with an electron beam, and in some embodiments, where the effect of the sterilization is toxic to the cells coated on, or to be coated on the substrate, alternative sterilization methods are sought or compensatory methods adopted, for example, additional growth factors can be added to the cells to reduce cells from detaching from the scaffold prior to forming extracellular matrix due to the use of irradiation sterilization.

In some embodiments, any cross-linkable non-cytotoxic hydrogel that can keep gel form at regular tissue culture condition (e.g., in culture media at 37° C.) and degradable with that particular hydrogel degrading enzyme whose optimal activity is in physiological pH range is suitable as a substrate for the methods and compositions and kits as disclosed herein.

In some embodiments, substrates can be modified in that a backing membrane film can be used, for example, any transparent membrane films that have minimal bonding with hydrogel to prevent gel detachment from membrane, large size pores to enable degrading enzymes to pass through freely and strength to protect hydrogel during harvest and transfer process.

In some embodiments, the cells in the cell sheet may be aligned with each other and with the nanograting on the scaffold or substrate such that at least 75% of the cells are aligned with an angle of less than 30°. The cells in the cell sheet may be aligned with each other and with the nanograting on the scaffold such that at least 65% of the cells are aligned with an angle of less than 10°. The cell layers can be removed from the substrate with enzymatic digestion which does not digest the extracellular matrix of cells (EMCs) and without the use of toxic or noxious solvents and without leaving a substantial amount of residual scaffold or substrate in or attached to the cell sheet.

In some embodiments, the substrates (e.g., the second substrate and/or receiving substrate) is nanoimprinted with a pattern or a nanograting. Imprinting on the surface of a scaffold can be performed using a polymethylmethacrylate coated Si master molds. The nanograte may have any suitable pattern. In some embodiments, a substrate has a pattern with a 280 nm depth, 350 nm width and 700 nm pitch was used. Those of skill in the art will appreciate that the nanograte may have a wide range of depths and widths limited by the ability to produce an intact cell sheet. Nanograte with widths up to 500 nm, 1 μm, 2 μm, 4 μm, 7 μm, 10 μm, 20 μm, 40 μm or even 80 μm and depths up to 300 nm, 400 nm, 500 nm, 1 μm, 2 μm, 4 μm, 8 μm, 10 μm, 20 μm, 30 μm, 40 μm, or 50 μm are suitable for use in the methods. Nanograte with widths of at least 50 nm, 100 nm, 200 nm, 250 nm, or 300 nm and depths of at least 25 nm, 50 nm, 100 nm, 150 nm, 200 nm, or 250 nm are suitable for use in the methods.

In some embodiments, the second substrate and/or the receiving substrates are patterned substrates, for example, have nanograte or are nanopatterns. In some embodiments, the second substrate and/or the receiving substrates are patterned substrates that have defined patterns of cell-adhesion molecules etc. as disclosed herein.

Methods for Generating a Nanograting or Nanoimprinting on the Substrates

1) Patterning

The rigid substrate can be coated with a thin layer of the transitional polymer by a variety of methods, including spin coating, dip casting, spraying, etc. A biopolymer is then patterned onto the transitional polymer with spatial control spanning the nanometer-to-micrometer-to-millimeter-to-centimeter-length scales. This level of spatial control can be achieved via patterning techniques including but not limited to soft lithography, self-assembly, vapor deposition and photolithography. Each of these techniques is discussed, in turn, below.

a) Soft Lithography: In soft lithography, structures (particularly those with features measured on the scale of 1 nm to 1 μm) are fabricated or replicated using elastomeric stamps, molds, and conformable photomasks. One such soft lithography method is microcontact printing using a polydimethylsiloxane stamp. Microcontact printing has been realized with fibronectin, laminin, vitronectin and fibrinogen and can be extended to other extracellular matrix proteins including, but not limited to collagens, fibrin, etc. Other biopolymers can be used as well, as this soft lithography method is quite versatile. There are few, if any, limitations on the geometry of the biopolymer structure(s) beyond the types of patterns that can be created in the polydimethylsiloxane stamps used for microcontact printing. The range of patterns in the stamps, in turn, is presently limited only by the current microprocessing technology used in the manufacture of integrated circuits. As such, available designs encompass nearly anything that can be drafted in modern computer-aided-design software. Multiple layers of biopolymers can be printed on top of one another using the same or different stamps with the same or different proteins to form an integrated poly-protein (poly-biopolymer) layer that can subsequently be released and used.

b) Self Assembly: Various biopolymers will spontaneously form self-assembled structures. Examples, without limitation, of self assembly include assembly of collagen into fibrils, assembly of actin into filaments and assembly of DNA into double strands and other structures depending on base-pair sequence. The self assembly can be directed to occur on the transitional layer to create a nanometer-to-millimeter-centimeter-scale spatially organized biopolymer layer. Further, self assembly can be combined with soft lithography to create a self-assembled layer on top of a soft lithographically patterned biopolymer; alternatively, the processes can be carried out in the reverse order. The self-assembled biopolymer, depending on the strength and stability of intermolecular forces, may or may not be stabilized using a cross-linking agent (for example, glutaraldehyde, formaldehyde, paraformaldehyde, etc.) to maintain integrity of the biopolymer layer upon release from the transitional layer. Otherwise, existing intermolecular forces from covalent bonds, ionic bonds, Van der Waals interactions, hydrogen binding, hydrophobic/hydrophilic interactions, etc., may be strong enough to hold the biopolymer scaffold together.

c) Vapor Deposition: Using a solid mask to selectively control access to the surface of the transitional polymer, biopolymers can be deposited in the accessible regions via condensation from a vapor phase. To drive biopolymers into a vapor phase, the deposition is performed in a controlled environmental chamber where the pressure can be decreased and the temperature increased such that the vapor pressure of the biopolymer approaches the pressure in the environmental chamber. Biopolymer surfaces produced via vapor deposition can be combined with biopolymer surfaces created by self-assembly and/or by soft lithography.

d) Patterned Photo-Cross-linking: Patterned light, x-rays, electrons or other electromagnetic radiation can be passed through a mask by photolithography; alternatively, the radiation can be applied in the form of a focused beam, as in stereolithography or e-beam lithography, to control where the transitional polymer biopolymers attach. Photolithography can be used with biopolymers that intrinsically photocross-link or that change reactivity via the release of a photoliable group or via a secondary photosensitive compound to promote cross-linking or breaking of the polymer chains so that the surface areas that are exposed to light are rendered either soluble or insoluble to a developing solution that is then applied to the exposed biopolymer to either leave only the desired pattern or remove only the desired pattern. The biopolymer is provided in an aqueous solution of biopolymer intrinsically photosensitive or containing an additional photosensitive compound(s).

Examples of photo-cross-linking process that can be utilized include (a) ultra-violet photo-cross-linking of proteins to RNA [as described in A. Paleologue, et al., "Photo-Induced Protein Cross-Linking to 5S RNA and 28-5.8S RNA within Rat-Liver 60S Ribosomal Subunits," Eur. J. Biochem. 149, 525-529 (1985)]; (b) protein photo-cross-linking in mammalian cells by site-specific incorporation of a photoreactive amino acid [as described in N. Hino, et al., "Protein Photo-Cross-Linking in Mammalian Cells by Site-Specific Incorporation of a Photoreactive Amino Acid," Nature Methods 2, 201-206 (2005)]; (c) use of ruthenium bipyridyls or palladium porphyrins as photo-activatable crosslinking agents for proteins [as described in U.S. Pat. No. 6,613,582 (Kodadek et al.)]; and (d) photocrosslinking of heparin to bound proteins via the cross-linking reagent, 2-(4-azidophenylamino)-4-(1-ammonio-4-azabicyclo[2,2,2] oct-1-yl)-6-morpho-lino-1,3,5-triazine chloride [as described in Y. Suda, et al., "Novel Photo Affinity Cross-Linking Resin for the Isolation of Heparin Binding Proteins," Journal of Bioactive and Compatible Polymers 15, 468-477 (2000)].

In some embodiments, the receiving substrate and/or a second substrate can be covered with a coating. The coating may be comprised of any combinations of normal constituents of the extracellular matrix (ECM). Those of skill in the art will appreciate that a wide variety of coatings may be used, including but not limited to, chitosan, hydroxybutyl chitosan, collagen, fibronectin, laminin, elastin, fibrin, gelatin, proteoglycans, hyaluronan, or combinations thereof. In the examples, hydroxybutyl chitosan and collagen were used. In some embodiments, the coating is about 10 nm thick. The thickness of the coating will affect the periodicity of the nanograting on the scaffold. Those skilled in the art will understand that a thicker or thinner coating may be used.

Cells Used in the Cell Layers

Cells seeded and cultured on the receiving cell layer and the second cell layer can be any cell type from any organism. In some embodiments, the cells are human cells. In some embodiments, the cells are mammalian cells. In some embodiments, the cells are from a transgenic mammal, e.g., a transgenic or modified mouse. In some embodiments, the cells have been genetically engineered or are recombinant cells. In some embodiments, the cells are derived or differentiated from stem cells, e.g., human stem cells or induced pluripotent stem cells (iPSC). In some embodiments, the cells have been genetically modified to carry a particular mutation or polymorphism or SNP characteristic to a particular disease or phenotype. In some embodiments, the cells are obtained from a subject, e.g., are autologous cells.

Examples of the cell to be cultured include, but are not limited to, myocardial cell, skeletal myoblast, mature skeletal muscle cell, smooth muscle cell, bone marrow stromal cell, corneal epithelial cell, oral mucosal epithelial cell and dermal cell. As demonstrated herein in the Examples, the cells are human umbilical vein endothelial cells (HUVEC's), fibroblasts (e.g., NIH-3T3 cells), human mesenchymal cells (hMSCs) (see FIG. 3E-3H).

For the cultivation of the cells on a culture dish to confluency, there are two approaches: one approach is by spreading cells of a single type; and the other approach is by spreading multiple types of cells simultaneously. For the cultivation of a single type of cells to confluency, there are two approaches: one approach is to plate a small amount of monoclonal cells having proliferation potency on a culture dish and then grow the cells until they reach confluency; the other approach is to plate a large amount of polyclonal cells having poor proliferation potency on a culture dish and, when they adhere onto the bottom of the culture dish, grow the cells until they reach confluency. As one example of the former approach, cells of an immortalized cell line (e.g., C2C12 strain cells derived from murine skeletal myoblasts, CMG cells, etc.) are plated in a small amount and grown on a culture plate until the cells reach confluency. As one example of the latter approach, myocardial cells, skeletal myoblasts, bone marrow stromal cells and the like are harvested from cardiac muscle, skeletal muscle, smooth muscle, bone marrow and the like, respectively, by primary culture techniques, the cells are selectively collected by means of a cell sorter, percoll or adhesion-based separation technique to increase the cell purity, and then a sufficient amount of the cells are plated on a culture dish. As one example of the approach for growing multiple types of cells to confluency, fibroblasts are mixed to myocardial or skeletal muscle cells before a cell sheet is formed from them. In this case, even if the number of the myocardial or skeletal muscle cells used is insufficient, fibroblasts which have high proliferation potency invade into the gaps among the myocardial or skeletal muscle cells and the entire bottom surface of the culture dish is covered with either type of cells, thus achieving a confluent state. In this manner, even cells which are difficult to harvest in a sufficient amount and which have poor proliferation potency can be grown to permit easy formation of a cell sheet by co-cultivation of "bridge-cells" such as fibroblasts. As such bridge-cells, not only fibroblasts but also smooth muscle cells and endothelial cells may be used. Depending on the type of cells used as "bridge", the strength and stretching property of a cell sheet can be modified for intended use.

Those skilled in the art will appreciate that many different types of cells may be used in the methods, including but not limited to, mesenchymal stem cells, myocyte precursor cells, myocytes, fibroblasts, chondrocytes, endothelial cells, epithelial cells, embryonic stem cells, hematopoetic stem cells, anchorage-dependent cell precursors, induced pluripotent stem cells (iPS cells), including adult fibroblasts, hMSCs, keratinocytes, and other somatic cells or combinations thereof. In the Examples, human mesenchymal stem cells (hMSCs) were used. As demonstrated in the Examples, the hMSCs were maintained in an undifferentiated, proliferative state in the cell sheets (see FIG. 3G-3H). The resultant cell sheets or layers may be exposed to differentiation cues either prior to implantation, or during culturing of the cell sheets/layers or may remain in an undifferentiated state and receive localized cues to aid proper differentiation after implantation into a subject. The hMSCs may be stimulated to differentiate along neuronal, myogenic or osteogenic lines.

In some embodiments, cells used for generating a multi-layered cell construct can comprise any combination of at least one of; fibroblasts, smooth muscle cells and endothelial cells, for example, to generate a vascular multi-layered cell construct, or tissue-engineered blood vessels (also referred to herein as a "TEBV").

In some embodiments, each of the individual cell sheets used to make the multi-layered cell construct comprise a single type of cells. For example, a cell sheet comprises only fibroblast, or only endothelial cells, or mesenchymal stem cells. In other embodiments, each of the individual cell sheets used to make the multi-layered cell construct comprise more than one type of cells. For example, a cell sheet comprises of endothelial cells and smooth muscle cells, or fibroblast and keratinocytes. When cell sheets having different cell types are stacked as described herein, the final product is a multi-layered cell construct that comprises more than one cell type.

In some embodiments, cells used for generating a multi-layered cell construct can comprise any combination of at least one of; cardiomyocytes, endothelial cells, vascular cells, or cardiac cells, e.g., to generate a cardiac patch multi-layered cell construct.

In some embodiments, cells used for generating a multi-layered cell construct can comprise any combination of at least one of; fibroblasts, endothelial cells and keratinocytes, e.g., to generate a multi-layered cell construct which is a skin graft multi-layered cell construct, e.g., for the treatment of wounds and skin damage (e.g., repair damaged skin due to injury, cancers, burns and other injuries).

In forming the cell layers or sheets, the cells produce extracellular matrix (ECM) and form tight junctions with neighboring cells to allow cell-cell communication as demonstrated in the examples. The cellular organization of tissues provides functional competence to many tissue types. In many cases cellular organization requires alignment of the cells. In the multi-layered constructs made by the methods described here, the cells are aligned. Suitably, at least 75%, 80%, 85%, 90%, 95%, 98%, 99% or 100% of the cells in the aligned second cell layer are aligned with an angle of less than 30° with respect to the alignment of the cells of the receiving cell layer. Suitably at least 60%, 65%, 70% or 75% of the cells in second cell layer are aligned with an angle of less than 10° with respect to the alignment of the cells of the receiving cell layer.

As discussed herein, the second cell layer is removed from the second substrate by enzymatic digestion with an enzyme which does not affect ECM or digest the receiving substrate. The remaining multiple cell layers are then removed from the receiving substrate by enzymatic digestion with a different enzyme which does not affect EMC to form a substantially scaffold-free multi-layered cell construct. In some embodiments, removal of the multiple cell layers from the receiving substrate may be assisted by using a device to gently peel the multiple cell layers off of the receiving scaffold. Those of skill in the art will appreciate that other coatings capable of being dissolved using enzymatic means and non-toxic means may be used to coat the scaffold.

The multi-layered cell construct may be made in any size or configuration desired. For example, the cell layers which are stacked upon each other (e.g., the second cell layer and receiving cell layer) may be circular, rectangular, square or any other shape. In some embodiments, rectangular and circular cell sheets are used. The cell layers (e.g., the second cell layer and receiving cell layer) may also be made in any size. For example, the multi-layered cell construct could be 1 cm×1 cm to 20 cm×20 cm. In some embodiments, a 6 cm×5 cm rectangular cell layers are stacked upon each other (e.g., the second cell layer and receiving cell layer) to make the TEBV. In some embodiments, a a 1.6 cm diameter circular multi-layered cell construct can be made.

In some embodiments, the multi-layered cell construct can be configured to any desired three-dimensional shape. In some embodiments, a specific 3D shape or geometric conformation of a multi-layered cell construct can be produced by cutting the multi-layered cell construct into the desired 3D configuration, or alternatively, by stacking different shapes of the second cell layer (and second substrate) onto a different shaped receiving cell layer (on the receiving substrate), much in the same way that three-dimensional printing is done, to generate a 3D multi-layered construct.

The cells may be derived from human and non-human animals (e.g., monkey, pig, mouse, rat, baboon, canine, feline, sheep or bovine). The cells may be harvested directly from the source such as an animal or they may be cultured cells of an established or unestablished cell line.

In some embodiments, the manufacture of a multi-layered cell construct is envisioned. The manufacture of multi-layered cell construct by culturing cells on the surface of a second substrate until the cells reach confluency; and contacting the second cell layer on the second substrate with the cultured cell present on the substrate surface of a receiving layer, dissolving the second substrate with an enzyme and repeating the process adding additional second cell layers on second substrates. The cultivation of the cells may be conducted by any method or under any condition as long as the cultivation is conducted on the surface of the substrates as disclosed herein. Generally, the cells are cultured in a culture medium until they become confluent, and the cultivation is continued for an additional three to four days in a culture medium. Once the cell layers are in contact, and pressure is applied to increase the adhesion between the two cell layers (e.g., the second cell layer and the receiving cell layer), the culture medium may optionally be aspirated off. If necessary, in some embodiments, the second cell layer attached to the second substrate may be detached from the second substrate using a detaching means such as a scraper. After the second cell sheet is detached, a few drops of a fresh culture medium may be applied onto the second cell layer (which now becomes the receiving cell layer) to unfold or smooth out the cell sheet, and/or before it is contacted with another second cell layer attached on a second substrate.

In some embodiments, any pressurizing device for adding a cell sheet on a second substrate to a cell sheet on a receiving substrate is envisioned for use in the methods as disclosed herein, e.g., any device or method exerting proper pressure to enhance the attachment between cell sheets without interrupting cell sheet-cell sheet bonding during pressure release process.

The cell layers may be used to form the multi-layered substrate by stacking cell layers or sheets together such that the cells in each cell sheet are aligned. In some embodiments, the cells are at a 60° angle with respect to a cell sheet above and/or below the cell sheet in the cell stack. In alternative embodiments, the cells on the receiving substrate can also be wrapped around receiving substrate which is cylindrical in shape, e.g., it can be wrapped around a mandrel to form a tube to form tissue-engineered blood vessels (TEBV).

Depending on the cell type, the cells may be cultured on the second substrate and/or the receiving substrate in an appropriate culture media and nutrient media for at least 2 days, or at least about 3-5 days, or at least about 7 days, or at least about 2 weeks or at least about 3 weeks or at least about 4 weeks or 5 weeks or more. The cells will form a cell monolayer on the second substrate and/or receiving substrate and will align to form a cell sheet.

Accordingly in one embodiment of this aspect and all other aspects described herein, a cell for use herein in the systems and methods to produce the multi-layered cell construct as disclosed herein and which is cultured on a second substrate or a receiving substrate is obtained from a biological sample. A biological sample as defined herein can include a human or mammalian biological sample, preferably a microdissected human or mammalian samples, are derived from a small tissue fraction, e.g., from a tumor tissue fraction. Examples of tissue tumor fraction are SCLC, colon or ovarian cancer, breast or cervical cancer tissue fraction. In some embodiments, the human or mammalian samples are preferably harvested by biopsy and/or surgical extraction.

Uses of the Multi-Layered Cell Constructs

The cell sheet resulting from this process can be used in a wide variety of applications which will be apparent to those skilled in the art. By using the method of the present disclosure to form a multi-layered cell construct from various cell types, tissue grafts for a variety of organs can be generated in vitro. Use of the tissue grafts thus prepared enables the establishment of analytical procedures in vitro at the cellular to tissue level.

The multi-layered cell constructs manufactured by the method of the present disclosure can be used in the field of regenerative medicine (e.g., implanted or transplanted into a subject) or in biological activity study on an agent. The resulting multi-layered cell constructs are substantially free of the receiving and/or second scaffold or substrate.

The multi-layered cell constructs and/or TEBV made by the methods disclosed herein may be used for a wide variety of purposes readily apparent to those of skill in the art. The ultimate use of the multi-layered cell constructs will be important in determining the cells used to make the cell sheets. The multi-layered cell constructs may be used to make many different tissues including, but not limited to, skin, bone, muscle tissue, cardiac tissue or even nerve tissue. The multi-layered cell constructs and/or TEBV may be implanted into (e.g., administered to) a subject. The subject may be any mammal, including humans. The multi-layered cell constructs and/or TEBV may be implanted by surgery or by injection in the area in need of treatment. For example, multi-layered cell constructs can be used to replace damaged skin may be implanted in the skin at the site of damage. Multi-layered cell constructs may also be injected in a site in need of bone regeneration to regenerate bone tissue. In another embodiment, a TEBV may be used to replace or repair a blood vessel in a subject during a surgical procedure.

As the multi-layered cell constructs for use in regenerative medicine, there may be a multi-layered myocardial cell construct, a multi-layered corneal epithelial cell construct, a multi-layered oral mucosal epithelial cell construct, a multi-layered dermal cell construct and the like. A myocardial multi-layered cell construct can be used for treatment of heart failure and arrhythmia resulting from cardiac infarction and various types of myocarditis and cardiomyopathy and as a material for cardiac muscle transplantation. A multi-layered corneal epithelial cell construct and a multi-layered oral mucosal epithelial cell construct can be used as materials for keratoplasty. A multi-layered dermal cell construct can be used for the treatment of wounds resulting from burns and injuries and the like. It may also be possible to use multi-layered fibroblast cell construct in therapy for wound cure promotion.

In some embodiments, the multi-layered cell constructs and/or tissue-engineered blood vessels (TEBVs) may be used to treat subjects in need of tissues by implanting the tissue sheets or TEBV into the subject. Those of skill in the art will appreciate that subjects having a wide range of clinical presentations may be in need of a tissue implant. For example, in subjects with vascular disease the TEBV may be implanted and used to replace a damaged blood vessel.

Tissue sheets may also be used to treat accident victims, burn victims, subjects with skin diseases and subjects with vascular diseases.

In some embodiments, the multi-layered cell constructs as disclosed has numerous applications and utilities, including a wide array of tissue-engineering applications. Examples of products and procedures that can be produced with the scaffolds include the following: (a) three-dimensional, anisotropic myocardium used to repair infarcts, birth defects, trauma and for bench top drug testing; (b) or repair of any muscle tissue.

The biological activity test of an agent may be exemplified by pharmacological activity test, toxicity test and biding activity test of an agent. Examples of the binding activity of an agent include ligand-receptor binding activity and anti-body-antigen binding activity. In comparison with the conventional methods for examining the change in cell behavior that results from addition of various agents to a culture medium for cell cultivation, the addition of such various agents to a cell sheet culture medium to examine the effect on the cell sheet enables examining not only the effect on cells themselves but also the effect on intercellular structure and construction. It is also possible to examine such effects of an agent at the cellular level, as well as at the organ level. A multi-layered cell constructs derived from different human organs can be transplanted onto organs of immunodeficient animals (e.g., nude mice, skid mice, nude rats) and, after administration of an agent to the transplantation model animals, the state of the cell sheets can be examined to predict the effect of the agent on human organs in vivo.

The biological activity of agents, including candidate substances for medicines and agricultural chemicals can be screened using the multi-layered cell constructs manufactured by the methods and systems as disclosed herein The multi-layered cell composition as disclosed herein and methods and system of their generation as disclosed herein are useful for various research applications, treatment methods, and screening methods.

Research Applications

The multi-layered cell composition as disclosed herein is useful for research applications, such as for example, but not limited to, introduction of the tissue engineered multi-layered cell composition into a non-human animal model of a disease (e.g., a cardiac disease or other diseases, such as diabetes, muscle degeneration etc;) to determine efficacy of the multi-layered cell composition in the treatment of the disease; use of the tissue engineered multi-layered cell composition in screening methods to identify candidate agents suitable for use in treating a particular disease or disorder; and the like. For example, a multi-layered cell composition generated herein using a subject method can be contacted with a test agent, and the effect, if any, of the test agent on any one or a combination of (i) a biological activity of a cell of the multi-layered cell composition, or (ii) the function of a multi-layered cell composition or (iii) the viability and/or differentiation of cells within the multi-layered cell composition can be assessed, where a test agent that has an effect on a biological activity of a cell within the multi-layered cell composition or the viability and/or differentiation of cells within the multi-layered cell composition can be used as candidate therapies for the treatment of a variety of diseases or disorder, or alternatively, if the agent decreases the viability, it indicates toxicity and thus would not be recommended as a therapeutic treatment or can be selected as a suitable agent for chemotherapy. As another example, a multi-layered cell composition generated using a subject method can be introduced into a non-human animal model of a particular disease, and the effect of the multi-layered cell composition on ameliorating the disorder can be tested in the non-human animal model.

Screening Methods

As noted above, a multi-layered cell composition as disclosed herein can be used in a screening method to identify candidate agents for treating a disease or disorder. For example, a multi-layered cell composition can be contacted with a test agent; and the effect, if any, of the test agent on a parameter associated with normal or abnormal multi-layered cell composition is determined.

In some embodiments, where the cells of the multi-layered cell composition are myocytes or cardiac cells, e.g., cardiomyotes, another aspect of the present disclosure relates to a use of a multi-layered cell composition as disclosed herein, in assays to identify agents which affect (e.g. increase or decrease) the contractile force and/or contractibility of the multi-layered cell composition in the presence of the agent as compared to a control agent, or the absence of an agent. Such an assay is useful to identify an agent which has a cardiotoxic effect, such as an agent which decreases contractile force, and/or cardiomyocyte atrophy, and/or results in another dysregulation of contractibility, such as arrhythmia or abnormal contraction rate. In another embodiment, such an assay is useful to identify an agent which has a cardiotoxic effects by increasing contractile force and/or other types of dysregulation such as an increase in contraction rate and could lead to the development of cardiac muscle hypertrophy.

In another embodiment, the multi-layered cell composition disclosed herein can be used in an assay to study a tissue with cells that carry a particular mutation or genetic variation. By way of an example only, the multi-layered cell composition can comprise genetically modified cells, for example, genetically modified cardiomyocytes, for example cardiomyogenic progenitors or cardiomyocytes carrying a mutation, polymorphism or other variant of a gene (e.g. increased or decreased expression of a heterologous gene) which can be assessed to see the effects of such a gene variant on the contractile force and contractible ability of the tissue engineered myocardium. Such a multi-layered cell composition comprising genetically modified cardiomyocyte or cardiomyogenic progenitor can also be used to identify an agent which attenuates (e.g. decreases) any dysfunction in contractibility or contraction force as a result of the genetically modified cardiomyogenic progenitors, or alternatively can be used to identify an agent which augments (e.g. increases) any dysfunction in contractibility or contraction force as a result of the genetically modified cardiomyogenic progenitors.

Another aspect of the disclosure relates to methods to screen for agents, for example any entity or chemicals molecule or gene product which effects (e.g. increase or decrease) the functionality of the multi-layered cell composition as disclosed herein, such as an agent which increases or decreases any function of the cells in the multi-layered cell composition, for example but not limited to, an agent which promotes differentiation, proliferation, survival, regeneration, or maintenance of a population of cells in the multi-layered cell composition, or an agent which prevent the differentiation of a cell in the multi-layered cell composition, and/or inhibits or negatively affects the cellular function or interaction with other cells within the multi-layered cell composition.

Parameters are quantifiable components of cells, particularly components that can be accurately measured, desirably in a high throughput system. A parameter can be any measurable parameter related to multi-layered cell composition as disclosed herein. Such parameters include, but are not limited to, changes in characteristics and markers of the cells of the multi-layered cell composition, and/or a change in the cell phenotype present within the multi-layered cell composition, including but not limited to changes in markers, cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters related to functionality of the multi-layered cell composition provide a quantitative readout, in some instances a semi-quantitative or qualitative result will also be acceptable. Readouts can include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

The multi-layered cell composition as disclosed herein is also useful for in vitro assays and screening to detect agents that are active on cells present within the multi-layered cell composition, for example, to screen for agents that affect the differentiation of cells, including differentiation of cells along a particular lineage, for example cardiac progenitors along a ventricular cardiomyocyte lineages. Of particular interest are screening assays for agents that are active on human cells. In such embodiments, the cells present on the multi-layered cell composition used in the screening assays can be embryonic stem cell- (ES) derived or induce pluripotent stem cell- (iPS) derived CVP cells.

In the use of a multi-layered cell composition as disclosed herein for the screening methods, a multi-layered cell composition is contacted with an agent of interest, and the effect of the agent is assessed by monitoring output parameters, such changes in gene expression and/or protein expression, changes in cell viability, and the like. In some embodiments, additional monitoring can be performed, such as alteration of the phenotype of the cells of the multi-layered cell composition, including but not limited to, e.g. changes in expression of markers, cell viability, differentiation characteristics, multipotenticy capacity and the like.

In some embodiments, the multi-layered cell composition for use in screening purposes can comprise cell variants, e.g., cells with a desired pathological characteristic. For example, the desired pathological characteristic can include a mutation and/or polymorphism which contribute to disease pathology, such as a cardiovascular disease. In such an embodiment, a multi-layered cell composition comprising a cell population with a desired pathological characteristic can be used to screen for agents which alleviate at least one symptom of the pathology.

In alternative embodiments, a multi-layered cell composition comprising a population of genetic variant cells, e.g. cells which endogenously, or genetically have been modified to have a particular mutation and/or polymorphism, can be used to identify agents that specifically alter the function a multi-layered cell composition comprising a genetic variant of the cells, as compared to the effect of the agent on the function of a multi-layered cell composition comprising normal or control cells (e.g. cells without the mutation and/or polymorphism). Accordingly, a multi-layered cell composition comprising a population of a genetic variant cells can be used to assess the effect of an agent in defined subpopulations of people and/or cells which carry modification. Therefore, the present disclosure enables high-throughput screening of agents for personalized medicine and/or pharmogenetics. The manner in which a multi-layered cell composition comprising a population of genetic variant cells responds to an agent, particularly a pharmacologic agent, including the timing of responses, is an important reflection of the physiologic state of the cell.

The agent used in the screening method using a multi-layered cell composition as disclosed herein can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof. An agent can contact the surface of the multi-layered cell composition (e.g. contact the population of cells on the outside or exterior of the multi-layered cell composition) such as by applying the agent to a media surrounding the multi-layered cell composition, where it contacts the cells and induces its effects. Alternatively, an agent can be intracellular within the cells within the multi-layered cell composition as a result of introduction of a nucleic acid sequence into cells and its transcription to result in the expression of a nucleic acid and/or protein agent within the cell. An agent as used herein also encompasses any action and/or event or environmental stimuli that a multi-layered cell composition is subjected to. As a non-limiting examples, an action can comprise any action that triggers a physiological change in the a multi-layered cell composition, for example but not limited to; heat-shock, ionizing irradiation, cold-shock, electrical impulse (including increase or decrease in stimuli frequency and/or stimuli intensity), mechanical stretch, hypoxic conditions, light and/or wavelength exposure, UV exposure, pressure, stretching action, increased and/or decreased oxygen exposure, exposure to reactive oxygen species (ROS), ischemic conditions, fluorescence exposure etc. Environmental stimuli also include intrinsic environmental stimuli defined below.

The exposure (e.g. contacting) of a multi-layered cell composition to agent may be continuous or non-continuous. In some embodiments, where the exposure (e.g. contacting) of a multi-layered cell composition to agent is a non-continuous exposure, the exposure of a multi-layered cell composition to one agent can be followed with the exposure to a second agent, or alternatively, by a control agent (e.g. a washing step). In some embodiments, a multi-layered cell composition can be exposed to at least one agent, or at least 2, or at least 3, or at least 4, or at least 5, or more than 5 agents at any one time, and this exposure can be continuous or non-continuous, as discussed above.

The term "agent" refers to any chemical, entity or moiety, including without limitation synthetic and naturally-occurring non-proteinaceous entities. In certain embodiments the compound of interest is a small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

In some embodiments, the agent is an agent of interest including known and unknown compounds that encompass numerous chemical classes, primarily organic molecules, which may include organometallic molecules, inorganic molecules, genetic sequences, etc. An important aspect of the disclosure is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this disclosure are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, e.g. drug candidates.

Agents such as chemical compounds, including candidate agents or candidate drugs, can be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for effect on a multi-layered cell composition by adding the agent to at least one and usually a plurality of multi-layered cell composition samples. A change in a parameter of the multi-layered cell composition in response to the agent is measured, and the result is evaluated by comparison to a reference multi-layered cell composition sample. A reference multi-layered cell composition sample can be, for example but not limited to, a multi-layered cell composition in the absence of the same agent, or a multi-layered cell composition in the presence of a positive control agent, where the agent is known to increase or decrease on at least one parameter measured in the multi-layered cell composition. In alternative embodiments, a reference multi-layered cell composition is a negative control, e.g. where the multi-layered cell composition is not exposed to an agent (e.g. there is an absence of an agent), or is exposed to an agent which is known not to gave an effect on at least one parameter measured in the multi-layered cell composition.

In some embodiments, the agents can be conveniently added in solution, or readily soluble form, to the multi-layered cell composition as disclosed herein. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over a multi-layered cell composition, followed by the second. In a single solution method, a bolus of the test compound is added to the volume of medium surrounding a multi-layered cell composition. The overall concentrations of the components of the culture medium surrounding the multi-layered cell composition should not change significantly with the addition of the bolus, or between the two solutions in a flow through method. In some embodiments, agent formulations do not include additional components, such as preservatives, that have a significant effect on the overall formulation. Thus, preferred formulations consist essentially of a biologically active agent and a physiologically acceptable carrier, e.g. water, ethanol, DMSO, etc. However, if an agent is a liquid without a solvent, the formulation may consist essentially of the compound itself.

A plurality of assays comprising a multi-layered cell composition can be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, e.g. at zero concentration or below the level of detection of the agent or at or below the concentration of agent that does not give a detectable change in the phenotype of a multi-layered cell composition.

Optionally, a multi-layered cell composition can be used in a screen as disclosed herein can comprise cells which have been manipulated to express a desired gene product. Gene therapy can be used to either modify a cell to replace a gene product or add a heterologous gene product, or alternatively knockdown a gene product endogenous to the cell.

In some embodiments the genetic engineering of a cell in a multi-layered cell composition is done to facilitate the differentiation into a particular cell type or along a particular cell lineage, or for the regeneration of tissue, to treat disease, or to improve survival of the cells, either while they are present as a component of a multi-layered cell composition, or following implantation of a multi-layered cell composition into a subject (e.g. to prevent rejection by the recipient subject). Techniques for genetically altering and transfecting cells, including cells are known by one of ordinary skill in the art.

A skilled artisan could envision a multitude of genes which would convey beneficial properties to a cell which is one element of the multi-layered cell composition as disclosed herein. Furthermore, a cell could be modified to convey an indirect beneficial property, such as the survival of the cells following transplantation of a multi-layered cell composition into a subject. An added gene can ultimately remain in the recipient cell and all its progeny, or alternatively can remain transiently, depending on the embodiment. As a non-limiting example, a gene encoding an angiogenic factor could be transfected into cells prior to seeding onto the second or receiving substrate and/or prior to generation of the multi-layered cell composition, or alternatively a cell can be transfected with a desired gene product when it is part of the multi-layered cell composition as disclosed herein. Use of such genes, such as genes which encode an angiogenic factor may be useful for inducing collateral blood vessel formation as the ventricular myocardium is generated, particularly if the multi-layered cell composition is used in for transplantation purposes into a subject in need of treatment. It some situations, it may be desirable to transfect a cell with more than one gene, for instance, a gene which promotes survival and/or a gene which promotes angiogenesis, and/or a gene which prevents rejection by the recipient subject following transplantation of a multi-layered cell composition into a subject.

In some instances, it is desirable to have the gene product expressed from cells present in a multi-layered cell composition secreted. In such cases, a nucleic acid which encodes the protein preferably contains a secretory signal sequence that facilitates secretion of the protein. For example, if the desired gene product is an angiogenic protein, a skilled artisan could either select an angiogenic protein with a native signal sequence, e.g. VEGF, or can modify the gene product to contain such a sequence using routine genetic manipulation (See Nabel et al., 1993).

The desired gene for use in modification of a cell for use in the multi-layered cell composition as disclosed herein can be transfected into the cell using a variety of techniques. Preferably, the gene is transfected into the cell using an expression vector. Suitable expression vectors include plasmid vectors (such as those available from Stratagene, Madison Wis.), viral vectors (such as replication defective retroviral vectors, herpes virus, adenovirus, adeno-virus associated virus, and lentivirus), and non-viral vectors (such as liposomes or receptor ligands).

A desired gene is usually operably linked to its own promoter or to a foreign promoter which, in either case, mediates transcription of the gene product. Promoters are chosen based on their ability to drive expression in restricted or in general tissue types, for example in mesenchymal cells, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Methods of gene targeting in mammals are commonly used in transgenic "knockout" mice (U.S. Pat. Nos. 5,616,491; 5,614,396). These techniques take advantage of the ability of mouse embryonic stem cells to promote homologous recombination, an event that is rare in differentiated mammalian cells. Recent advances in human embryonic stem cell culture may provide a needed component to applying the technology to human systems (Thomson; 1998). Furthermore, the methods of the present disclosure can be used to isolate and enrich for stem cells or progenitor cells that are capable of homologous recombination and, therefore, subject to gene targeting technology. Indeed, the ability to isolate and grow somatic stem cells and progenitor cells has been viewed as impeding progress in human gene targeting (Yanez & Porter, 1998).

Treatment Methods

In another embodiment, the multi-layered cell composition as disclosed herein can be used for prophylactic and therapeutic treatment of a condition or disease. By way of an example only, in such an embodiment, a multi-layered cell composition as disclosed herein can be administered to a subject, such as a human subject by way of transplantation, where the subject is in need of such treatment, for example, the subject has, or has an increased risk of developing a disease or disorder for wjocj the transplantation of the multi-layered cell composition would relieve or reduce at least one or more symptoms of the disease or disorder.

In some embodiments, the multi-layered cell composition as disclosed herein can be introduced into a subject in need thereof, e.g., as an exemplary example, where the multi-layered cell composition comprises cardiac cells, e.g., cardiomyocytes or cardiac precursor cells, a multi-layered cell composition as disclosed herein can be introduced on or adjacent to existing heart tissue in a subject. In one embodiment, a multi-layered cell composition as disclosed herein is useful for replacing damaged heart tissue (e.g., ischemic heart tissue), for example, where a multi-layered cell composition as disclosed herein is introduced or administered (e.g. implanted) into a subject.

In some embodiments, the tissue engineered multi-layered cell composition which is transplanted comprises cells originated and derived from the subject in which the multi-layered cell composition is implanted. Accordingly, allogenic or autologous transplantation of the multi-layered cell composition into a subject can be carried out.

Another aspect of the present disclosure provides methods of treating a disease or disorder in a subject, the method generally involving administering to a subject in need thereof a therapeutically effective amount of a multi-layered cell composition as disclosed herein. In some embodiments, the present disclosure also provides methods of treating a cardiac disorder in a subject, the method generally involving administering to a subject in need thereof a therapeutically effective amount of a multi-layered cell composition which comprises a substantially pure population of cardiac cells, or cardiac progenitor cells as disclosed herein.

In some embodiments, the multi-layered cell composition as disclosed herein is useful for generating artificial heart tissue, e.g., for implanting into a mammalian subject. In some embodiments, the multi-layered cell composition as disclosed herein is useful for replacing damaged heart tissue (e.g., ischemic heart tissue). Accordingly, one can use of the multi-layered cell composition as described herein to repair and/or reinforce the cardiac or heart tissue in a mammal, e.g., an injured or diseased human subject. For example, in some embodiments a multi-layered cell composition can be used, for example but not limited to, in tissue implants or as a patch or as reinforcement to a heart which is weak contraction or alternatively has been damaged due to a myocardial infarction, and/or as a wound dressing. Such wound dressing can offer improved cardiac function of a subject with a cardiac lesion such as myocardial infarction. The multi-layered cell composition as disclosed herein is also useful to repair other tissue defects, e.g., any tissue which is damaged by injury, disease or a genetic defect. In some embodiments, the multi-layered cell composition comprises fibroblasts and other skin cells is useful for the treatment of wounds and wound repair. In some embodiments, a multi-layered cell composition is used to correct facial deformities, e.g., cleft palette or cleft lip or after a facial injury. In some embodiments, the multi-layered cell composition can comprise pancreatic cells and can be used for the treatment of diabetes. In some embodiments, the multi-layered cell composition comprises myocytes, e.g., for the replacement or treatment of muscle degenerative diseases or muscle injury. In some embodiments, the multi-layered cell composition comprises cartilage cells for the treatment of degenerated joints and cartilage degeneration. In some embodiments, the multi-layered cell composition comprises osteoblasts and osteocasts and other bone cells for the replacement or enhancement of bone growth, e.g., in a subject who has a broken bone or has had bone surgery, for example, a hip or knee or other joint replacement. In some embodiments, the multi-layered cell composition comprises liver cells for the treatment of liver diseases. In some embodiments, the multi-layered cell composition can comprise cardiac cells, e.g., cardiomyocytes or cardiac progenitors for cardiac repair due to birth defects (congenic) or acquired cardiac defects, or to function as a splint for damaged or weakened muscle, for example in degenerative muscular disorders where muscle atrophy of the heart occurs, such as multiple sclerosis (MS), ALS and muscular dystrophy and the like. In some embodiments, depending on the cells present or within the multi-layered cell composition, the multi-layered cell composition can be used for any type of regenerative medicine application. In some embodiments, the multi-layered cell composition are portable and amenable to both hospital (e.g., operating room) use as well as field (e.g., battlefield) use. The tissue multi-layered cell composition are easily transported, for instance, cell sheets or the multi-layered cell composition are packaged wet or dry, e.g., the second and/or receiving substrate alone, the second and/or receiving substrate alone plus cells, or the second and/or receiving substrate alone, plus cell, plus a drug (e.g., antibiotic, blood coagulant or anti-coagulant). The second and/or receiving substrate alone can comprise a pattern or mesh of filaments or threads. The filaments or threads are organized into a grid structure or are present in an amorphous tangle. The receiving substrate is dissolved from the cells to form the multi-layered cell composition, which is then to injured or diseased tissue.

A subject in need of treatment using a subject method include, but are not limited to, individuals having a congenital heart defect; individuals suffering from a condition that results in ischemic heart tissue, e.g., individuals with coronary artery disease; and the like. A subject method is useful to treat degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

For administration to a mammalian host, the multi-layered cell composition as disclosed herein can be formulated as a pharmaceutical composition. A pharmaceutical composition can be a sterile aqueous or non-aqueous solution, suspension or emulsion, which additionally comprises a physiologically acceptable carrier (e.g., a non-toxic material that does not interfere with the activity of the active ingredient). Any suitable carrier known to those of ordinary skill in the art may be employed in a subject pharmaceutical composition. The selection of a carrier will depend, in part, on the nature of the substance (e.g., cells or chemical compounds) being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, antioxidants, chelating agents and/or inert gases, and/or other active ingredients.

In some embodiments, where a multi-layered cell composition is administered to a subject in need thereof, the multi-layered cell composition can be encapsulated, according to known encapsulation technologies, including microencapsulation (see, e.g., U.S. Pat. Nos. 4,352,883; 4,353,888; and 5,084,350, which are incorporated herein by reference). Where the multi-layered cell composition is encapsulated, in some embodiments the multi-layered cell composition is encapsulated by macroencapsulation, as described in U.S. Pat. Nos. 5,284,761; 5,158,881; 4,976,859; 4,968,733; 5,800,828 and published PCT patent application WO 95/05452 which are incorporated herein by reference. A unit dosage form of a multi-layered cell composition can contain from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells.

A multi-layered cell composition as disclosed herein can be cryopreserved according to routine procedures. For example, cryopreservation can be carried out on from about one to ten million cells in "freeze" medium which can include a suitable proliferation medium, 10% BSA and 7.5% dimethylsulfoxide. Cells are centrifuged. Growth medium is aspirated and replaced with freeze medium. Cells are resuspended as spheres. Cells are slowly frozen, by, e.g., placing in a container at −80° C. Cells are thawed by swirling in a 37° C. bath, resuspended in fresh proliferation medium, and grown as described above.

As discussed above, the multi-layered cell composition as disclosed herein can be used as a pharmaceutical composition to the treatment of a subject in need thereof, for example for the treatment of a subject with a cardiomyopathy or a cardiovascular condition or disease. In some embodiments, a multi-layered cell composition as disclosed herein may further comprise a cell differentiation agent, which promotes the differentiation of cells into a particular lineage desired by the end user. If it is desirable to differentiate the cells along a cardiac lineage, cardiovascular stem cell differentiation agents for use in the present disclosure are well known to those of ordinary skill in the art, and include, but are not limited to, cardiotrophic agents, creatine, carnitine, taurine, cardiotropic factors as disclosed in U.S. Patent Application Serial No. 2003/0022367 which is incorporated herein by reference, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway. The pharmaceutical compositions may further comprise a pharmaceutically acceptable carrier.

A multi-layered cell composition as disclosed herein can be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. The multi-layered cell composition as disclosed herein may also be modified by insertion of DNA to modify the function of the cells for structural and/or therapeutic purpose. As discussed herein, gene transfer techniques for stem cells are known by persons of ordinary skill in the art, as disclosed in (Morizono et al., 2003; Mosca et al., 2000), and can include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Murarnatsu et al., 1998).

In another aspect, cells present within the multi-layered cell composition as disclosed herein for transplantation can be modified to comprise a gene encoding pro-angiogenic and/or cardiomyogenic growth factor(s) which would allow the cells to act as their own source of growth factor during cardiac repair or regeneration following transplantation into a subject. Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid' adeno-associated virus. Cells can be genetically manipulated to release and/or express genes for a defined period of time (such that gene expression could be induced and/or controlled, so expression can be continued and/or be initiated. Particularly, when a cell composition or multi-layered cell composition as disclosed herein is administered to a subject other than the subject from whom the cells and/or tissue were obtained, one or more immunosuppressive agents may be administered to the subject receiving a multi-layered cell composition as disclosed herein in order to reduce, and preferably prevent, rejection of the transplant by the recipient subject. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Pub. No 20020182211. In one embodiment, a immunosuppressive agent is cyclosporine A. Other examples include myophenylate mofetil, rapamicin, and anti-thymocyte globulin. In one embodiment, an immunosuppressive drug is administered with at least one other therapeutic agent. An immunosuppressive agent can be administered to a subject in a formulation which is compatible with the route of administration and is administered to a subject at a dosage sufficient to achieve the desired therapeutic effect. In another embodiment, an immunosuppressive agent is administered transiently for a sufficient time to induce tolerance of the multi-layered cell composition as disclosed herein.

In some embodiments, a multi-layered cell composition as disclosed herein can be administered to a subject with one or more cellular differentiation agents, such as cytokines and growth factors, as disclosed herein. Examples of various cell differentiation agents are disclosed in U.S. Pat. application Ser. No. 2003/0022367 which is incorporated herein by reference, or Gimble et al., 1995; Lennon et al., 1995; Majumdar et al., 1998; Caplan and Goldberg, 1999; Ohgushi and Caplan, 1999; Pittenger et al., 1999; Caplan and Bruder, 2001; Fukuda, 2001; Worster et al., 2001; Zuk et al., 2001. Other examples of cytokines and growth factors include, but are not limited to, cardiotrophic agents, creatine, carnitine, taurine, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway.

A multi-layered cell composition as disclosed herein can be administered to a subject in need of a transplant. In other aspects of the present disclosure, a multi-layered cell composition as disclosed herein is directly administered at the site of or in proximity to the diseased and/or damaged tissue. A multi-layered cell composition as disclosed herein for therapeutic transplantation purposes can optionally be packaged in a suitable container with written instructions for a desired purpose, such as the use of the multi-layered cell composition as disclosed herein to improve some abnormality of the cardiac muscle, in particular the right ventricle of the heart.

In one embodiment, a subject can be administered a multi-layered cell composition as disclosed herein and also administered, either in conjunction or temporally separated a differentiation agent. In one embodiment, a multi-layered cell composition as disclosed herein is administered separately to the subject from the differentiation agent. Optionally, a multi-layered cell composition as disclosed herein is administered separately from the differentiation agent, there is a temporal separation in the administration of the a tissue engineered myocardium composition and the differentiation agent. The temporal separation may range from about less than a minute in time, to about hours or days in time. The determination of the optimal timing and order of administration is readily and routinely determined by one of ordinary skill in the art.

Advantages of the Multi-Layered Cell Substrate

The multi-layered cell constructs as disclosed herein provide multiple advantages over present tissue engineering methods and scaffold.

One such advantage is a significant reduction in production costs. For example, a commonly known scaffold for tissue engineering or creation of multi-layered cell constructs is UpCell, which is relatively expensive; currently 100 mm UpCell pack (6 dishes) is being sold for $280. Also, UpCell requires use additional tools such as a plunger and a 20° C. incubator to harvest and transfer cell sheets in the UpCell system. In contrast, the system and methods to produce the multi-layered cell construct as disclosed herein is extremely low (e.g. potentially in a few dollars range even for the laboratory setting not even considering yet the mass-production setting). Furthermore, the system and methods to produce the multi-layered cell construct as disclosed herein does not require any special tools except a pressure plate that can be provided in commercial product packet, and its production cost would be less than a dollar. Furthermore, the multi-layered cell construct as disclosed herein can be produced in a regular tissue culture laboratory or setting, such as a biohood and incubator.

Another advantage is the cell sheet harvest and transfer process using the system and methods to produce the multi-layered cell construct as disclosed herein. In contrast to UpCell, which requires both (i) the use of temperature change from 37° C. to 20° C. to harvest cell sheet, which risks damage and harmful effects to the cultured cells (e.g., particularly non-robust and sensitive cells such as endothelial cells) due to the sudden temperature drop, and also (ii) a gelatin stamp which risks killing the cells due to limited oxygen and nutrition supply and moisture deprivation, the present the system and methods to produce the multi-layered cell construct as disclosed herein maintains the temperature at 37° C., with similar nutrition and gas exchange conditions during the entire harvest and transfer process that promotes high cell viability.

The system and methods to produce the multi-layered cell construct as disclosed herein has additional advantages in that is can be scaled up for large scale production of multi-layered cell constructs and tissue engineering and can be conformed to any geometric shape desired by the user. Unlike the tissue construct of UpCell, who's product scale up is limited due to the dimensions of the grafting surface (the largest surface is a 100 mm dish size), the present disclosure using the system and methods to produce the multi-layered cell construct as disclosed herein allows a scale up to at least 1 m×1 m. Furthermore, as the system and methods uses hydrogels as substrates, scale up is virtually unlimited. Also, the multi-layered cell construct as disclosed herein can be configured to any sophisticated geometrical shape based on the backing 2D geometry of the second substrates and the receiving substrates.

In some embodiments, the substrates used in the system and methods to produce the multi-layered cell construct as disclosed herein can be controlled for their stiffness. For example, when culturing cells in cell-specific natural growth environment is important to maintain cell-specific characteristics. It has been known that the differentiation lineage of some mesenchymal stem cells is determined according to the underlying substrate stiffness. Therefore, cell sheets for very soft tissue application cannot be grown on hard culture plastic substrate. In contrast to the UpCell system that cannot control substrate stiffness, the stiffness of the substrates used on the systems and methods to produce the multi-layered cell construct as disclosed herein can be tuned and controlled to accurately mimic target cell-specific natural biomechanical growth environments by controlling the polymer concentration of the hydrogel.

Kits

Another aspect of the present disclosure relates to kits or pharmaceutical packages comprising at least the materials for generating a second substrate and a receiving substrate (e.g. either the materials to formulate the enzymatically degradable hydrogels, or the enzymatically degradable hydrogels themselves), and a first digestive enzyme for digesting the receiving substrate, and a second digestive enzyme for digesting the second substrate. In some embodiments, the kit further comprising at least one pressure plate. The kits can be used to generate multi-layered cell substrates according to the methods ad disclosed herein. In some embodiments, the kit comprises a receiving substrate which is cylindrical in shape for generating a TEBV according to the methods as disclosed herein.

The substrates provided in the kits can be provided in packages, in a bottle or another appropriate form (e.g., a blister pack). Optionally, the kits or pharmaceutical packages can also include other pharmaceutically active agents (see, e.g., the agents listed above, such as other agents used for increasing or promoting the adherence and/or survival of the cells on the substrates, such as growth factors and adhesion molecules etc.), and/or culture media and materials for culturing the second and/or receiving substrate and/or multi-layered cell substrate for a pre-defined amount of time, as well as, optionally any materials used in administration of the multi-layered cell substrate, such as diluents, needles, syringes, applicators, and the like to a subject.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

The present disclosure can be defined in any of the following numbered paragraphs:

[1] A method of making a multi-layered cell construct comprising:
   a. contacting a second cell layer with a receiving cell layer, wherein the second cell layer is present on a second substrate, and the receiving cell layer comprises at least one cell layer and is present on a receiving substrate, and wherein the receiving substrate can be digested by a first enzyme, and the second substrate can be digested by a second enzyme,
   b. applying pressure to the second substrate and the receiving substrate, and
   c. applying a second enzyme to digest the second substrate, wherein after digestion of the second substrate, the receiving substrate comprises multiple cell layers comprising the at least one receiving cell layer and the second cell layer,
   d. repeating steps (a)-(c) for a desired number of times, wherein the second cell layer of the multiple cell layers present on the receiving substrate in step (c) is used as the receiving cell layer for step (a), and
   e. applying a first enzyme to digest the receiving substrate to form a multi-layered cell construct.

[2] The method of paragraph 1, wherein step (d) is repeated at least about 2 times.
[3] The method of paragraph 1, wherein step (d) is repeated between 2-10 times.
[4] The method of paragraph 1, wherein step (d) is repeated between about 10-50 times.
[5] The method of paragraph 1, wherein step (d) is repeated between about 50-100 times.
[6] The method of paragraph 1, wherein step (d) is repeated more than about 100 times.
[7] The method of paragraph 1, wherein prior to the contacting step, the method comprises:
  a. culturing the cells on a receiving substrate for an appropriate period of time for the cells to form a confluent receiving cell layer, wherein the receiving substrate can be digested by a first enzyme, and
  b. culturing cells on a second substrate for an appropriate period of time for the cells to form a confluent second cell layer, wherein the second substrate can be digested by a second enzyme.
[8] The method of paragraph 1 or 2, wherein the receiving cell layer and second cell layer have the same cell types.
[9] The method of paragraph 1 or 2, wherein the receiving cell layer and second cell layer have different cell types.
[10] The method of paragraph 1 or 2, wherein the receiving substrate and the second substrate comprise enzyme digestible polymers.
[11] The method of paragraph 10, wherein the enzyme digestible polymer is a hydrogel.
[12] The method of paragraph 1 or 2, wherein the receiving substrate comprises carboxylmethyl cellulose (CMC) and the first enzyme is cellulose.
[13] The method of paragraph 1 or 2, wherein the second substrate comprises alginate (Al) and the second enzyme is alginate lyase.
[14] The method of paragraph 1 or 2, wherein the receiving substrate comprises alginate (Al) and the first enzyme is alginate lyase.
[15] The method of paragraph 1 or 2, wherein the second substrate comprises carboxylmethyl cellulose (CMC) and the second enzyme is cellulose.
[16] The method of any of paragraphs 12-15, wherein the carboxylmethyl cellulose (CMC) or alginate (Al) are conjugated with tyramin (Ty).
[17] The method of paragraph 16, wherein the carboxylmethyl cellulose-tyramin (CMC-Ty) is at least 1%, and wherein the alginate-tyramin (Al-ty) is at least 1%.
[18] The method of any one of paragraphs 1-17, wherein the first and second enzymes do not digest the extracellular matrices of cells (EMC).
[19] The method of any one of paragraphs 1-18, wherein the second substrate and the receiving substrates are patterned substrates.
[20] The method of any one of paragraphs 1-19, wherein the second substrate and the receiving substrates have a predetermined substrate stiffness to maintain the cell-specific characteristics of the cells in the cell layer on the substrate.
[21] The method of any one of paragraphs 1-20, wherein the second cell layer and/or the receiving cell layer comprises cells selected from the group consisting of: mesenchymal stem cells (MSCs), myocyte precursor cells, myocytes, fibroblasts, chondrocytes, endothelial cells, epithelial cells, embryonic stem cells (ESCs), hematopoietic stem cells, anchorage-dependent cell precursors, induced pluripotent stem cells (iPSCs), cardiomyocytes, and combinations thereof.
[22] The method of paragraph 21, wherein the iPSCs are selected from fibroblasts, keratinocytes, and mesemchymal stem cells.
[23] The method of paragraphs 21 or 22, wherein the second cell layer and/or the receiving cell layer comprises human cells.
[24] A multi-layered cell construct produced by the methods of any one of paragraphs 1-23.
[25] The multi-layered cell construct of paragraph 24, wherein the second cell layer and/or the receiving layer comprises at least one of fibroblasts, smooth muscle cells and endothelial cells.
[26] The multi-layered cell construct of paragraph 24, wherein the second cell layer and/or the receiving layer comprises at least one of cardiomyocytes, endothelial cells, vascular cells, or cardiac cells.
[27] The multi-layered cell construct of paragraph 24, wherein the second cell layer and/or the receiving layer comprises at least one of fibroblasts, endothelial cells and keratinocytes.
[28] The multi-layered cell construct of paragraph 24, wherein the multi-layered construct is configured into a specific three-dimensional shape.
[29] The multi-layered cell construct of paragraph 28, wherein the three-dimensional shape resembles a specific tissue shape.
[30] The multi-layered cell construct of any of paragraphs 24-29, for use in an assay to identify an agent which increases or decreases the viability of the cells within multi-layered cell construct.
[31] The multi-layered cell construct of any of paragraphs 24-29, for use in an assay to identify an agent which increases or decreases the function of the cells within multi-layered cell construct.
[32] A method of making a tissue-engineered blood vessel comprising the method of any one of paragraphs 1-23, wherein the receiving substrate is in a cylindrical geometry, and wherein the receiving cell layer is on the outer surface of the cylinder.
[33] The method of paragraph 32, wherein the second cell layer and/or the receiving layer comprises at least one of fibroblasts, smooth muscle cells and endothelial cells.
[34] A tissue-engineered blood vessel made by the method of paragraph 32.
[35] A method of treating a vascular disease in a subject, comprising transplanting into the subject a tissue-engineered blood vessel according to paragraph 34.
[36] A method of treating a subject in need thereof a skin graft, comprising transplanting into the subject a multi-layered construct produced by the methods of any one of paragraphs 1-23, wherein at least the second cell layer and/or the receiving layer comprises at least one of fibroblasts, endothelial cells and keratinocytes.
[37] A method of treating a subject in need of a skin graft, comprising transplanting into the subject the multi-layered construct according to paragraph 31.
[38] The method of paragraph 36, wherein the subject in need thereof is in need of wound healing.
[39] The method of paragraph 38, wherein the wound healing is selected from the group consisting of: severe burns, field wound care, emergency wound care.
[40] A kit comprising materials for generating a second substrate and a receiving substrate, a first digestive enzyme for digesting the receiving substrate, and a second digestive enzyme for digesting the second substrate.

[41] The kit of paragraph 40, further comprising at least one pressure plate.

While the disclosure has been particularly shown and described with reference to a number of embodiments, it would be understood by those skilled in the art that changes in the form and details may be made to the various embodiments disclosed herein without departing from the spirit and scope of the disclosure and that the various embodiments disclosed herein are not intended to act as limitations on the scope of the claims. All references cited herein are incorporated in their entirety by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the disclosure. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The disclosure can be understood more fully by reference to the following detailed description and illustrative examples, that are intended to exemplify non-limiting embodiments of the disclosure.

EXAMPLES

The examples presented herein relate to compositions comprising multi-layered cell sheet stacks, and methods and systems to make such multi-layered cell sheet stacks using individual layers of cell sheets on scaffold/support materials that are digested by specific enzymes. In some embodiments, the method of making such a multi-layered cell sheet stacks comprises stacking individual layers of cell sheets, one on top of another. In some embodiments, the method comprises culturing individual layers of cell sheets on a substrate that can be digested by specific enzymes, e.g., carboxymethyl cellulose (CMC) conjugated with tyramin (ty): CMC-ty; and alginate (Al) conjugated with tyramin (ty): Al-ty) that can be degraded by cellulose and alginate lyase respectively. These specific enzymes do not digest the extracellular matrices of cells. This allows multiple layers of cell sheets to be stacked and the supporting substrate to be digested prior to the additional of an additional cell sheet to generate a multi-layered cell construct as disclosed herein. Throughout this application, various publications are referenced. The disclosures of all of the publications and those references cited within those publications in their entireties are hereby incorporated by reference into this application in order to more fully describe the state of the art to which this disclosure pertains. The following examples are not intended to limit the scope of the claims to the disclosure, but are rather intended to be exemplary of certain embodiments. Any variations in the exemplified methods that occur to the skilled artisan are intended to fall within the scope of the present disclosure.

Materials and Methods

To demonstrate the growth and improvement of patterned cell sheets, we selected a hydrogel substrate system because hydrogels are easy to form topological pattern, control surface-cell interaction using protein adsorption, and tune surface modulus by changing solution concentration. CMC-ty and Al-ty hydrogels are degradable by the matching enzyme cellulose and alginate lyase, respectively to release cell sheets.[19,20] To facilitate the transfer and stacking of cell sheet-hydrogel construct, we developed hydrogel films consists of the same material for each hydrogel type.

Polymer Modification

Carboxymethyl Cellulose (CMC) Modification 0.5 mM or 1 mM MES buffer was prepared and adjusted to pH 6.0. CMC-Na and Tyramine hydrochloride were dissolved and stirred overnight. NHS, HOBt, and EDC were added and stirred for another 24 hours at room temperature to form CMC-tyramine conjugate (CMC-ty). The polymer solution was dialyzed using 20,000 MW dialysis membrane (Thermo Scientific) for 48 hours and subsequently lyophilized using VirTis lypophilzer.

Alginate Modification 1 mM MES buffer was prepared and adjusted to pH 6.0. Alginic acid was dissolved in MES buffer overnight. NHS and EDC were added and stirred for 2-3 hours at room temperature. Tyramine hydrochloride was then added and stirred 24 hours to form an alginate-tyramine conjugate (Al-ty). The polymer solution was dialyzed in a 20,000 MW dialysis membrane (Thermo Scientific) for 48 hours and lyophilized.

Lyophilized CMC-ty and Al-ty were stored at −20° C. CMC-ty and Al-ty were dissolved in Krebs Ringer HEPES-buffered (KRH, pH 7.4) solution 1-4% w/v ratio (e.g. 0.1 g in 10 ml) to prepare hydrogel solution. CMC-ty and Al-ty solutions were filtered using a 5 µm and 1 µm filter, respectively. Filtered 1% CMC-ty and Al-ty solutions were stored at 4° C. for further use. To induce gelation, solution of CMC-ty or Al-ty, HRP (horseradish peroxidase), and $H_2O_2$ groups were mixed with a 100:3:10 volume ratio, respectively. Alternatively, a 10:1:2 volume ratio was used. Due to the different number of tyramine incorporated per cellulose or alginate branch, the mixing ratio was adjusted by varying the HRP volume.

Patterned Al-Ty and CMC-Ty Backing Film Preparation

Figure 2A:
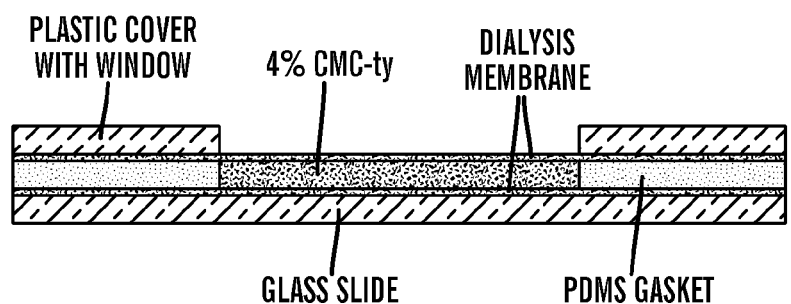
FIGS. 2A-2B show CMC-ty and Al-ty film preparation.
Figure 2B:
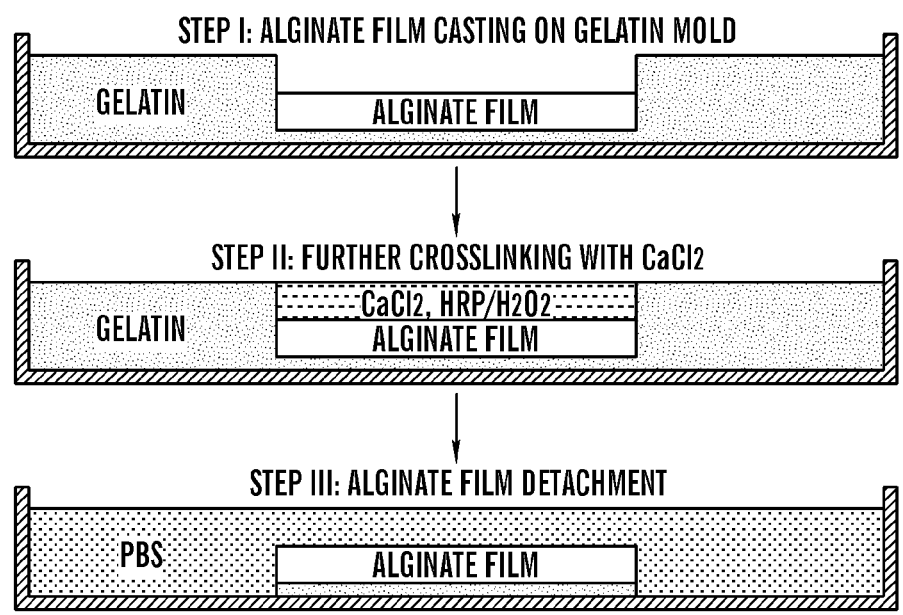
Figure 9:
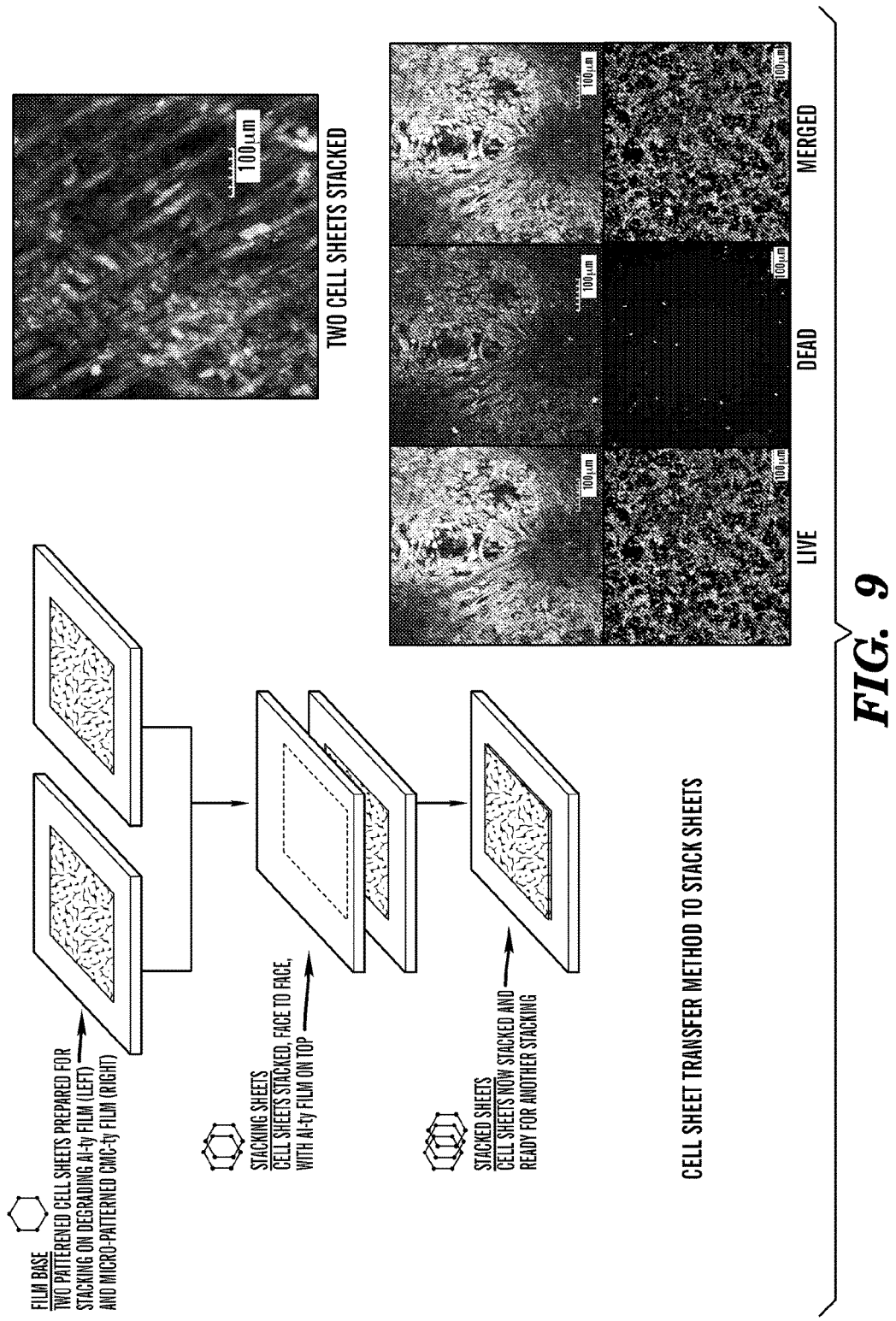
FIG. 9 is a schematic diagram showing the cell sheet transfer method used to make stacks of sheets.
Figure 10:
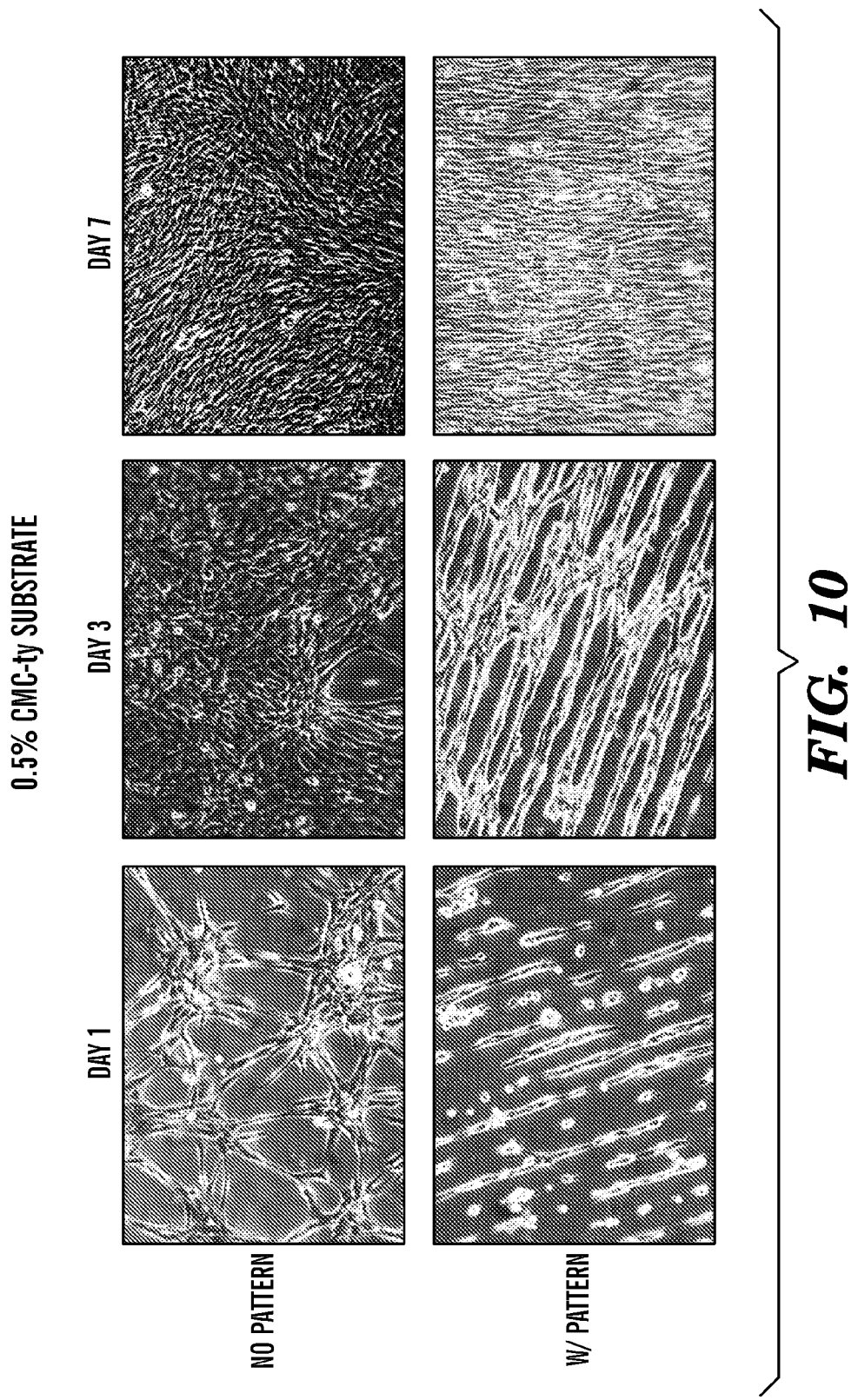
FIG. 10 shows the growth of cells on 0.5% CMC-ty non-patterned and pattern substrates at 1, 3, 7 days post cell seeding.

The inventors developed backing films consisting of the same materials as Al-ty and CMC-ty hydrogels to degrade both hydrogel substrate and backing film at the time of cell sheet harvest (FIG. 2). A 4% CMC-ty solution mixed with HRP was cast in a mold and treated with a 2.7 mM $H_2O_2$ solution to form a CMC-ty film. To fabricate the Al-ty film, a gelatin mold was prepared into which a solution mixture (1% Al-ty, HRP, and $H_2O_2$) was poured and gelated for 10 min at 4° C. To increase the rigidity, the alginate film was incubated with a 100 mM $MgCl_2$ solution mixed with HRP (1.6 units/ml) and $H_2O_2$ (2.7 mM) for 10 minutes and washed with $Mg^{2+}$ and $Ca^{2+}$ free phosphate buffered saline (PBS). To dissolve the remaining gelatin underneath the film, both film types were incubated with PBS at 37° C. for 3 hours. To evaluate film degradability, Al-ty and CMC-ty films were subjected to the matching degrading enzyme, i.e. alginate lyase and cellulase, respectively. To serve as a backing film, a CMC-ty or Al-ty film was glued down onto the culture dish using 1% CMC-ty or Al-ty hydrogel, respectively, and kept under PBS at 37° C. until further processing. See FIGS. 1, 2 and 9.

Alternatively, a 1.5% CMC-ty or Al-ty solution was mixed with HRP (1.5 U/ml) and cast in a topographically patterned gelatin mold, and then further treated with a 2.7 mM $H_2O_2$ solution to form a CMC-ty film for 40 min at 4° C. To increase the rigidity, the Al-ty substrate was further incubated with a 100 mM $MgCl_2$ solution mixed with and $H_2O_2$ (2.7 mM) for 10 minutes and washed with $Mg^{2+}$- and $Ca^{2+}$-free phosphate buffered saline (PBS). To dissolve the remaining gelatin underneath the substrate, both substrate types were incubated at room temperature for 2 hours, washed with warmed up PBS, and incubated overnight at 37° C. for complete gelatin removal. To evaluate substrate degradability, Al-ty and CMC-ty substrate were subjected to the matching degrading enzyme, i.e. alginate lyase and cellulase, respectively. To promote cell attachment, collagen type-I was adsorbed onto the patterned CMC-ty substrate surface; 1 mM collagen type-I (BD Sscience) was diluted in PBS by 1:10 volume ratio, and the substrate was incubated with diluted collagen for 24 hours at 37° C. Collagen adsorption procedure was same for both CMC-ty and Al-ty substrates. To remove extra collagen, the substrate was washed with PBS three times at room temperature and incubated at 37° C. 12 hours. To culture cell sheets, collagen type I-coated CMC-ty or Al-ty substrates was glued down onto the culture dish using 1% CMC-ty or Al-ty hydrogel, respectively, and kept under PBS at 37° C. until cell seeding.

Topographical Patterning of Cell Sheet Substrate

To make topographical patterns on the substrate, we prepared patterned gelatin mold (50 μm ridges & 20 μm grooves). 150 ul of 1% CMC-ty, HRP and $H_2O_2$ solution mixture was immediately poured onto a CMC-ty (3 cm×3 cm) backing film, and a gelatin mold was immediately stamped on the gel solution. The entire construct was kept in 4° C. for 20 minutes for complete gelation. 2 ml of PBS was added and incubated at 37° C. for 2 hours to dissolve gelatin. The patterned substrate was washed with warmed PBS three times and incubated at 37° C. for 24 hours for complete removal of gelatin. To promote cell attachment, collagen type-I was adsorbed onto the patterned substrate surface; 1 mM collagen type-I (BD science) was diluted in PBS by 1:10 volume ratio, and the substrate was incubated with diluted collagen for 18 hours at 37° C. To remove extra collagen, the substrate was washed with PBS three times at room temperature and incubated at 37° C. another 24 hours before seeding cells. The same procedure was used to fabricate patterned Al-ty substrate (FIGS. 3 and 8).

Substrate Young's Modulus Tuning to Provide Cell Type Specific Biomechanical Growth Environment.

The Young's modulus of CMC-ty and Al-ty substrate was tuned by varying CMC-ty and Al-ty concentration (w/v). 1%, 2% and 4% were selected for CMC-ty, and 1%, and 2% for Al-ty. 1% and 2% CMC-ty and 1% Al-ty solution were directly mixed with HRP and $H_2O_2$ to cast onto the backing film. However, due to the high viscosity and instant gelation, a 4% CMC-ty solution and 2% Al-ty solution mixed with HRP was casted in a mold covered by dialysis membrane and treated with 2.7 mM $H_2O_2$ solution for gelation. For further increase of modulus, the gelated 2% Al-ty was treated with 100 mM $CaCl_2$ for 10 minutes. Young's modulus measurements were performed using atomic force microscopy (AFM). Three samples were prepared for each concentration and substrate type (CMC-ty or Al-ty), and at least three measurements were made for each sample. Linearized hertzian model was used to measure Young's modulus.

Growing Patterned Cell Sheet

Three different cell types (NIH 3T3, human mesenchymal stem cells (hMSCs), human umbilical veil endothelial cells (HUVEC)) were used to evaluate cell attachment on patterned CMC-ty and Al-ty substrate surface. About 100,000 cells in a 400 μl volume were seeded onto a 9 $cm^2$ surface area, and kept in an incubator for 2 hours for cell attachment. Then, a 6 ml of media was added for further culturing. At least more than three patterned and confluent cell sheets were cultured for each cell type (FIGS. 3 and 8).

Cell Sheet Transfer and Stacking

Two individually patterned cell sheets were fully grown, and culture media was replaced by serum-free culture media with fibronectin (10 ug/ml) at 37° C. for 1 hour. Serum-free culture media was then completely removed for both cell sheets. One cell sheet construct (cell sheet cultured on CMC-ty substrate that is supported on CMC-ty backing film or cell sheet cultured on Al-ty substrate that is supported on Al-ty backing film) was lifted and flipped to make cell sheet-cell sheet contact while maintaining 60° alignment between the two patterned cell sheets. Adjacent cell sheets should have different cell type and substrate. A dialysis membrane and a pressure plate with multi-pillars were placed on top of backing film of the flipped cell sheet construct to enhance cell sheet-cell sheet bonding. To keep cells viable, 1 ml of culture media was added and incubated for 1.5-2 hour at at 37° C. for cell sheet-cell sheet bonding (FIGS. 1 and 8). Media was aspirated, and the pressure plate and dialysis membrane were removed. The enzyme specific for the top cell sheet construct, either celluase or alginate lyase, was mixed with pH adjusted media. After adding enzyme-containing media, the construct was incubated for 1-1.5 hour at 37° C. to degrade the top construct. Entire construct was washed with fresh media three times to remove degraded Al-ty. The same procedure was repeated to stack additional cell sheets.

Cell Tracker Dye Staining to Visualize Post Transfer Pattern Preservation

A two or three layered patterned cell sheet stack was kept submerged in the media and imaged using confocal microscopy (Olympus IX81, Fluoview1000). INVITROGEN™ Cell Tracker Green CMFDA, and Cell Tracker Red CMTPX were used to stain individual cell sheets, respectively according to manufacturer's protocol. At least more than three samples were prepared to confirm the post-transfer pattern preservation of the cell sheets. To acquire clear confocal images, cell sheets were transferred on fibronectin-adsorbed glass cover slips. Glass coverslips were incubated with fibronectin solutions (10 μg/ml) at 37° C. for 2 hours and used within one hour for cell sheet transfer.

Live/Dead Assay for Cell Viability

Cells were stained using LIVE/DEAD® (INVITROGEN™) assay kit 4 and 24 hours after cell sheet stacking to evaluate post-stacking cell viability according to manufacturer's protocol. Live/Dead staining was performed on a two-layered cell sheet stack and images were taken using confocal microscopy (Olympus IX81, Fluoview1000, 20× magnification).

Example 1

Figure 7:
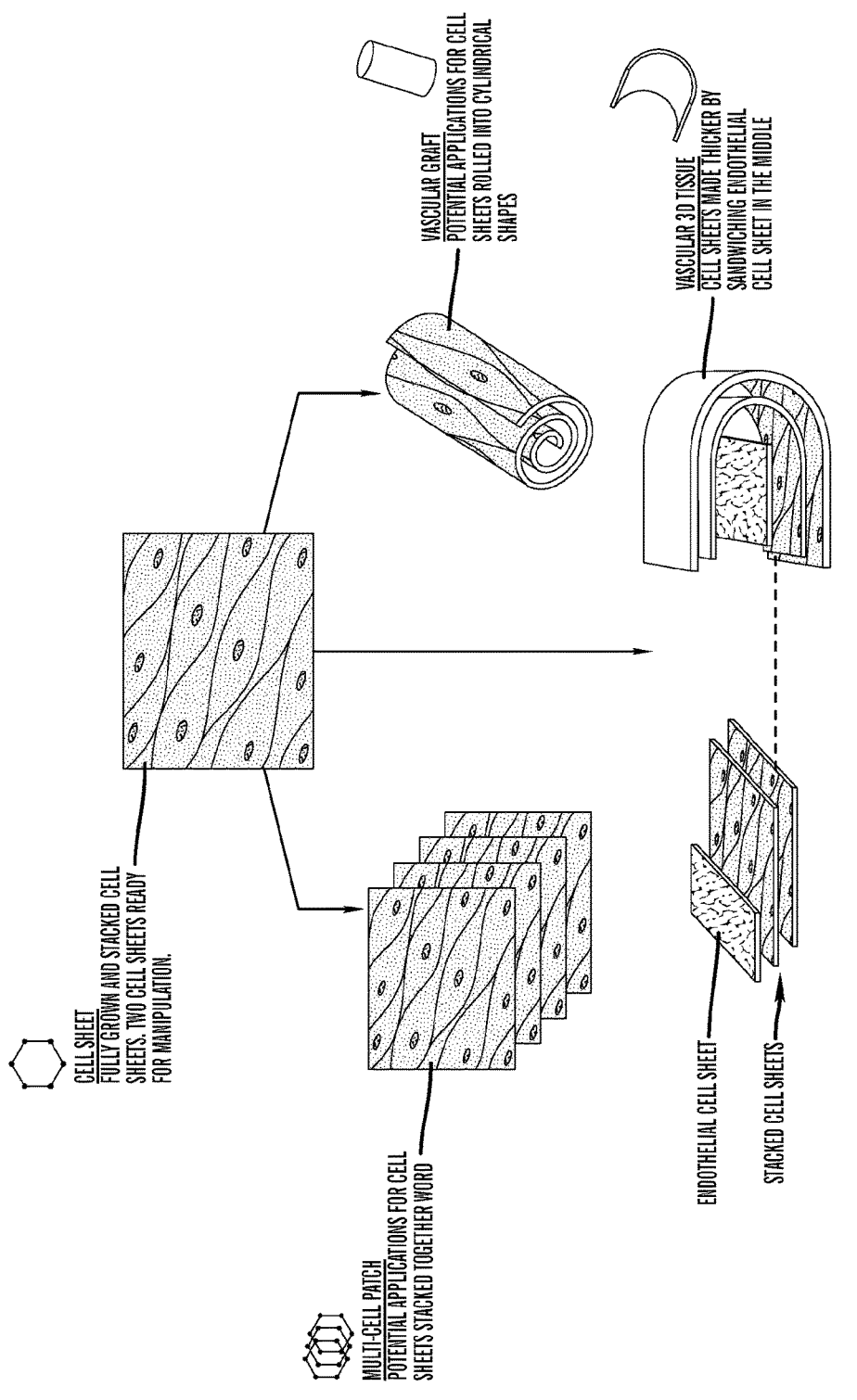
FIG. 7 shows the application of the disclosed cell sheets. Disclosed are some embodiments of integrated structures comprised of cell sheets that are made of cells and cell-secreted extracellular matrix (ECM).
Figure 8A:
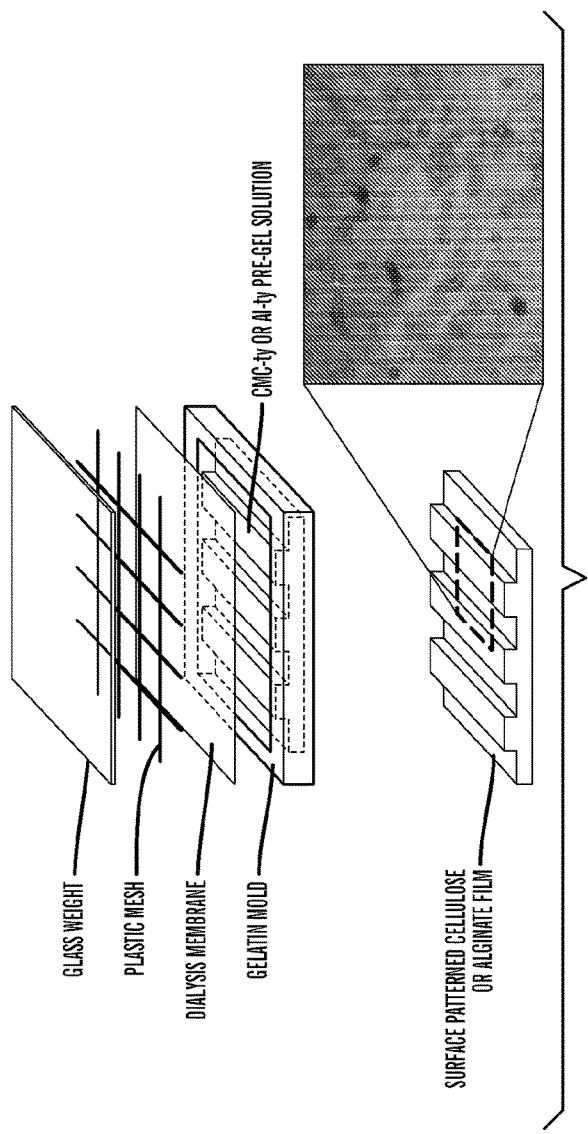
FIG. 8A shows hydrogel (CMC-ty or Al-ty) substrate preparation.
Figure 8B:
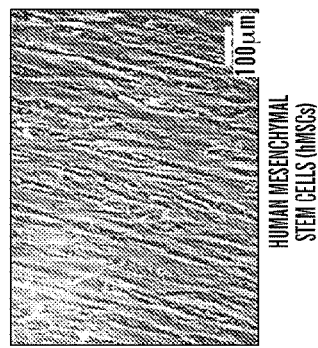
FIGS. 8B-8E shows the cell sheet formation for various cell types: Human umbilical Vein Endothelial cells (HU-VECs) (FIG. 8B), mouse fibroblasts (NIH 3T3) (FIG. 8C), Bovine vascular smooth muscle cells (BVSMCs) (FIG. 8D), and human mesenchymal stem cells (hMSCs) (FIG. 8E).
Figure 8C:
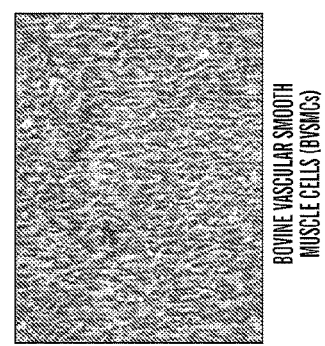
Figure 8D:
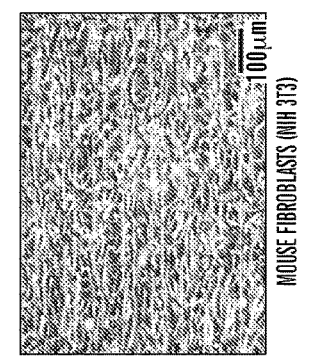
Figure 8E:
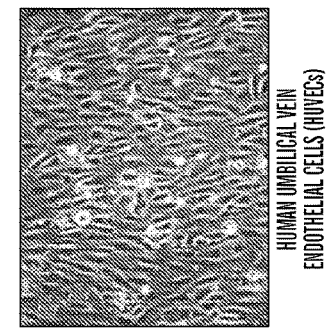

Tissue structure is directly related to its function.[1-3] In order to recapitulate native tissue structure over the length scales required for tissue function, one must control cell movement and cell-ECM interactions.[4-6] Ideally, substrate topology should provide directional guidance to induce desired cell migration and alignment. Biomechanical environment control such as surface modulus as well as temporal and spatial profile of growth factors should modulate cell phenotype and proliferation to achieve cell self-assembly on cell-secreted ECM only.[8-9] Whereas, conventional tissue engineering has attempted to control these physicochemical parameters individually,[7,10,11] cell sheet technology has been recently suggested to control some of these parameters simultaneously; in cell sheets, cells and cell-secreted ECM are integrated in the form of a sheet without any artificial materials.[12-14] Patterned cell sheets could mimic 2D native structure of target tissue, and proper stacking according to the anatomy of target tissue could reproduce complex 3D tissue structure, which in turn could acquire specific tissue function.[14-15] However, several issues remain to be solved in order to make the prior cell sheet technology a practical tool. Cell sheet technology should provide cell type specific physicochemical growth environments to modulate cell behavior or even differentiation. Post stacking high cell viability must to be maintained, and multiple cell sheet production within a short period of time such as a week should be capable while achieving quality control.[16-18] Here, we demonstrate the use of an enzyme degradable polymer hydrogel based cell sheet harvest and transfer system. Two modified natural polymers serve as substrates: Carboxymethyl cellulose (CMC) conjugated with tyramine (ty) (CMC-ty) and alginate (Al) conjugated with tyramine (Al-ty) are degradable by matching enzyme namely cellulase and alginate lyase.[19-20] The methods, assays, systems and compositions as disclosed herein is capable to modulate topology of substrate surface to mimic 2D native tissue structure as shown in FIG. 7. Substrate modulus can be tuned by changing polymer solution concentration. In addition, cell friendly culture and transfer procedure result in post transfer and stacking high cell viability. Because hydrogel has no limit in 2D shape and size, scale-up is easy for producing quality controlled multiple cell sheets in a short period of time. To validate the capabilities of the system, we modified the topology of substrate surface to produce patterned cell sheet and used Cell Tracker™ (INVITROGEN™) to trace post stacking pattern preservation. We demonstrated that substrate modulus tuning capability using AFM measurement, and Live/Dead assay was performed 4 hours and 24 hours after stacking to verify post stacking high cell viability.

Example 2

Al-Ty Film and CMC-Ty Film Fabrication

A one-percent Al-ty film gelated by both HRP and $Mg^{2+}$ based crosslinking displayed sufficient structural rigidity to be used as backing film supports for Al-ty substrates for the cell sheets. Also a 4% CMC-ty film gelated by only HRP crosslinking was rigid enough to be transferred by forceps when the thickness of the CMC-ty film was increased two folds thickness of Al-ty film. In the degradability test, both films were completely degraded in 90 minutes.

Topographical Surface Patterning of Al-Ty and CMC-Ty Substrate

Figure 3A:
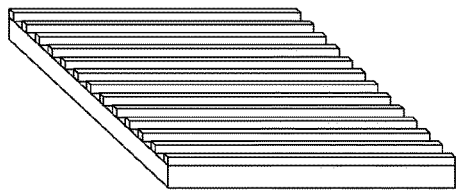
FIGS. 3A-3H show the substrate patterning process and patterned cell sheet from various cell types with seeding density (300,000 cells per substrate (3 cm×3 cm)).
Figure 3B:
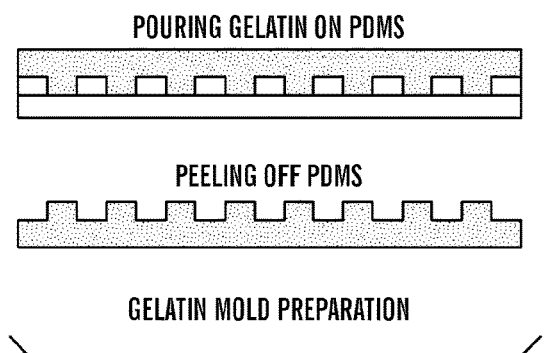
Figure 3C:
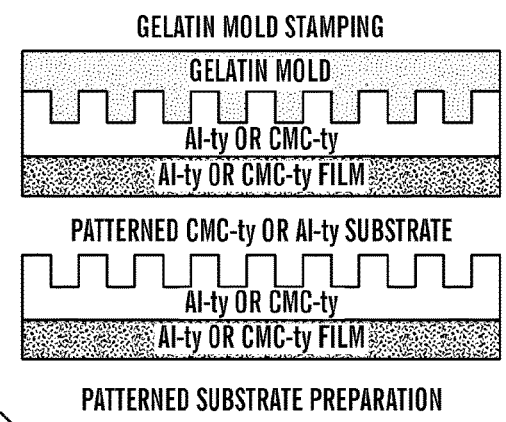
Figure 3D:
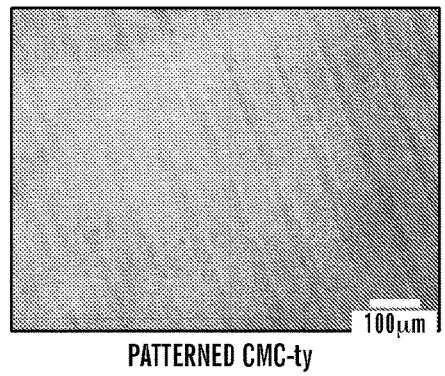
Figure 3E:
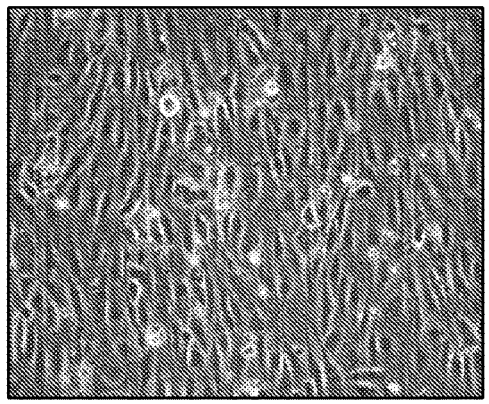
Figure 3F:
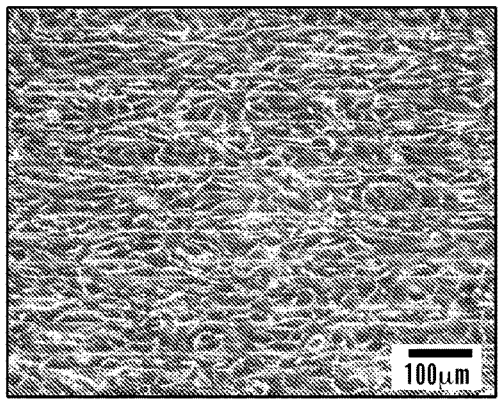
Figure 3G:
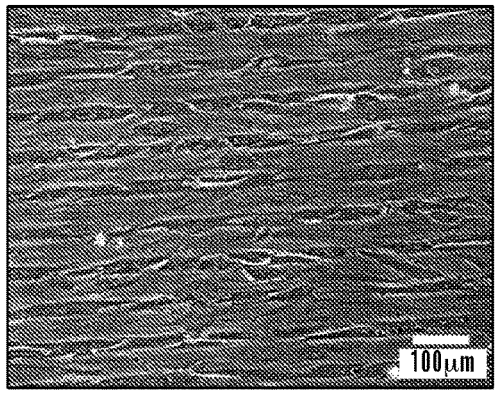
Figure 3H:
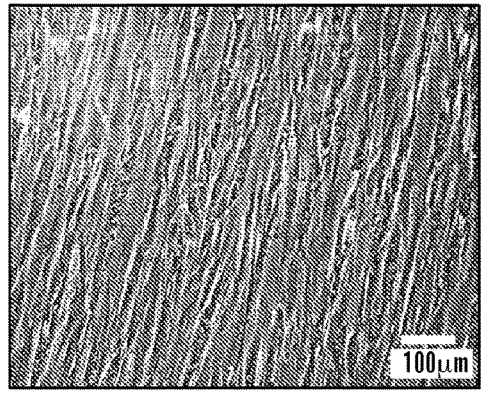

Using the gelatin (ridges (20 μm) & grooves (50 μm)) stamp method and a specific ratio (i.e. Al-ty (1%): HRP (29 U/ml): $H_2O_2$ (334 mM)=100:5:10) of solution mixture, the inventors demonstrated that a clearly patterned surface (ridges (50 μm) and grooves (20 μm)) was possible on both CMC-ty and Al-ty substrate (FIG. 3D). Type I collagen adsorption promoted cell attachment and proliferation (FIGS. 3E-H). Additional embodiments of patterning are shown in FIG. 8.

Figure 4A:
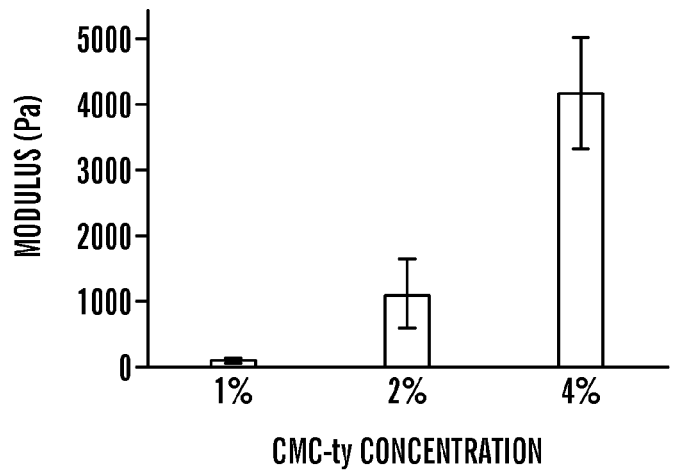
FIGS. 4A-4B show AFM substrate surface stiffness measurement.
Figure 4B:
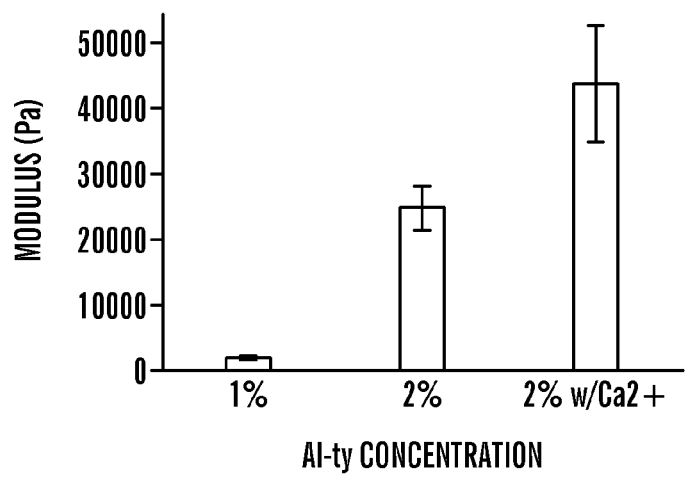
Figure 5:
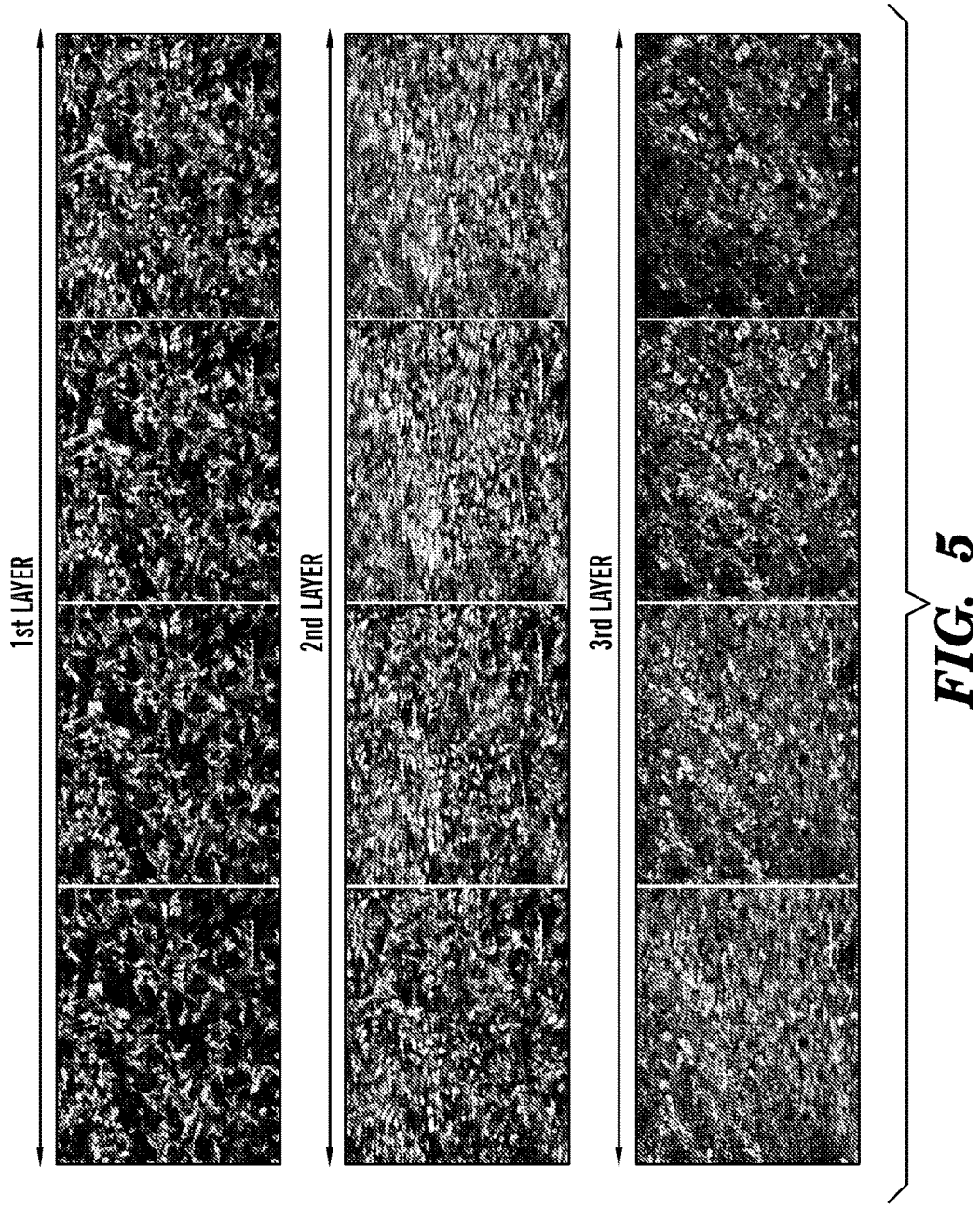
FIG. 5 shows a series of confocal images of three layers of cell sheet constructs (NIH 3T3 cells) that were stacked one layer on top of another. Cells on different layers were stained different to add distinguishing the layers. The stained three patterned (ridges & grooves) cell sheets were stacked with approximately 60° between each cell sheet pattern direction. All layers show viable cells after stacking. All scale bars are 100 μm.
Figure 6A:
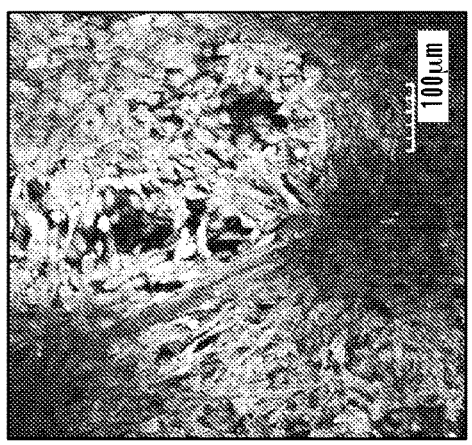
FIGS. 6A-6F show results from a LIVE/DEAD assay (INVITROGEN™) to detect post cell sheet transfer cell viability (FIGS. 6A-6C 2 hrs post stacking, FIGS. 6D-6F 24 hrs post stacking.)
Figure 6B:
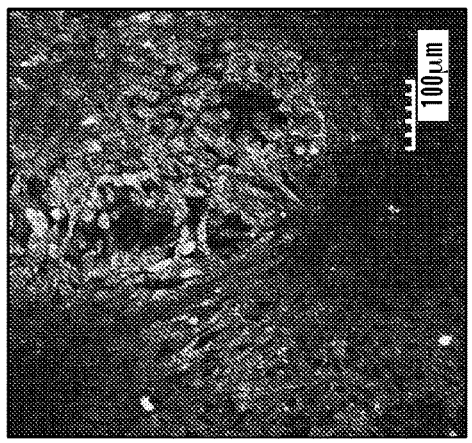
Figure 6C:
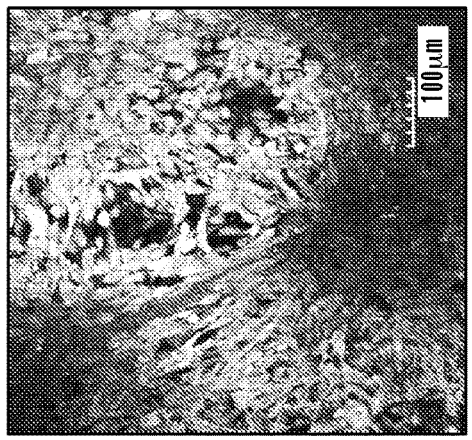
Figure 6D:
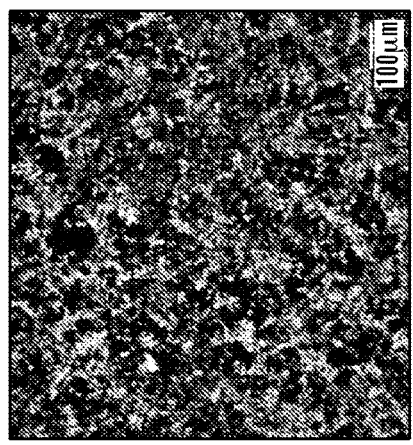
Figure 6E:
Figure 6F:
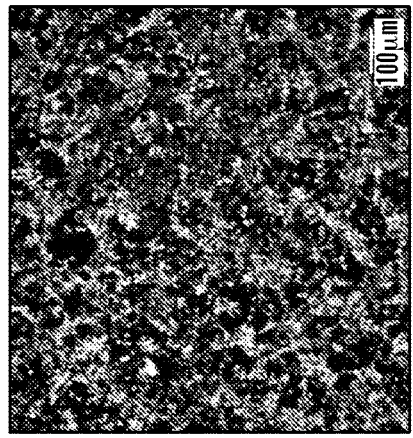

Substrate Modulus Tuning by Varying Polymer Concentration and Crosslinking Methods To measure Young's modulus of substrate hydrogel, both 1% CMC-ty and Al-ty solutions were mixed with HRP and $H_2O_2$ with an appropriate mixing ratio and casted between glass cover slips to fabricate flat gels for AFM measurements. While modulus of the 1% CMC-ty gel was in the 100 Pa range, a 1% Al-ty gel was in the 1900 Pa range. The 2% CMC-ty gel modulus was in the 1100 Pa range, whereas, 2% Al-ty gel modulus was significantly higher (24 KPa range). To achieve the modulus range of muscle (about 50 KPa23), 2% Al-ty gel was additionally crosslinked with $Ca^{2+}$ to increase the modulus. A 2% Al-ty gel with $Ca^{2+}$ driven crosslinking resulted in a two-fold increase of modulus (about 50 KPa). A 4% CMC-ty gel concentration was in 4 KPa range (FIG. 4). Modulus range of the hydrogel substrate was from 100 Pa to 50 KPa, and this range covers most of the soft tissue modulus except tendon.

Growing Cell Sheet from Various Cell Types

Upon cell seeding, all three cell types (NIH 3T3 fibroblasts, mouse mesenchymal stem cells (mMSCs), human umbilical veil endothelial cells (HUVECs)) achieved full confluence to form patterned cell sheets within 7 days of culture (FIGS. 3E-3H, and 8). For this type of patterned surface (3 cm×3 cm), $2.5×10^5$ cells/ml was an optimal density to form initial cell alignment along the grooves. Although fully confluent cell sheets were formed within 4 days with higher seeding densities (i.e. $3.5×10^5$ cell/ml), cell alignment was irregular and randomly oriented cell sheets were formed.

Cell Sheet Transfer & Stacking and Post Transfer Pattern Preservation

INVITROGEN™ Cell Tracker Green (CMFDA) and Red (CMTPX) were used to stain individual cell sheets on CMC-ty and Al-ty substrates, respectively. For a two cell sheet stacks, one cell sheet grown on Al-ty substrate and one cell sheet grown on CMC-ty substrate were used. For experiment purposes to distinguish the sheets after layering, the Al-ty substrate was stained with a red fluorescent dye marker and CMC-ty substrate was stained with a green fluorescent dye marker. For three cell sheet stacks, two cell sheets grown on Al-ty substrate and one cell sheet grown on a CMC-ty substrate were used. Stacking of two or three fully grown cell sheets preserved the cell alignment pattern (FIGS. 1D, 5, 9 and 10).

Live/Dead® Assay to Assess Post Transfer Cell Viability

A Live/Dead® assay performed on two-cell sheet stack 4 and 24 hours after stacking procedure at least three times and showed more than 99% of cell viability (FIG. 6).

Example 3

The present disclosure involves a degradable natural polymer hydrogel based cell sheet harvest and transfer system that yields high cell viability and preserve topographical cell alignment after stacking. Cell sheet technology possesses many advantages; properly patterned cell sheet consists of cell and cell-secreted ECM without artificial materials and accurately mimics topological characteristics of 2D structure of target tissue. Stacking cell sheets according to the anatomy of target tissue could reproduce tissue function.

In this study, cultured cell sheets on topologically patterned hydrogel substrates were transferred onto other cultured cell sheets to form a stack of cultured cell sheets that consist of patterned or not patterned cell sheets. The capability of the system was assessed for ability to produce highly viable cell sheet stacks that preserve initial topological characteristics after stacking. Various cell types (NIH 3T3, HUVECs, hMSCs) cultured on both hydrogel substrates achieved confluent and well patterned cell sheets (FIGS. 3E-3H). The Cell Tracker staining study clearly revealed that tight connections formed between stacked cell sheets preserved cell sheet pattern after stacking (FIGS. 1D, 5, 9 and 10). Live/Dead assay 4 and 24 hours after stacking and 5 day follow-up confirmed that both enzymes, cellulase and alginate lyase driven degradation process and degradation by-products still kept cell highly viable (over 99%) (FIG. 6).

Stacking process is always maintained under media without temperature transition from 37° C. In addition, because the entire cell sheet construct, which consists of a rigid backing film and a hydrogel substrate for cell growth, is composed of the same material (i.e. either CMC-ty or Al-ty, respectively), the cell sheet transfer and stacking procedure (i.e. lifting, flipping, and stacking) is simple and gentle. Moreover, no additional tools or materials are required other than pressure plate and enzymatic degradation of entire construct.

Topographical substrate surface patterning using gelatin stamp (FIG. 4) combined with substrate modulus control over a wide range (100 Pa to 50 KPa) (FIG. 5) could provide customized biomechanical growth environments for a specific target cell type. Furthermore, easy scale-up potential due to ease of hydrogel processing into 2D shapes offers rapid mass-production of three dimensional engineered tissue from stacked cell sheets at low cost. Repeated topological patterning and stacking were done more than four times for each polymer type substrate. Series of successful short-term fabrication of two or three cell sheet stacks confirm that the assay, methods and systems as disclosed herein could produce highly viable and layer-by-layer structurally organized cell sheet stacks.

In order to create three dimensional tissues over the length scale of diffusion limit, vascularization is required to deliver nutrition and oxygen.[17] Using the system, methods and compositions as disclosed herein, it is easy to replicate 2D natural vascular network pattern like embedded channels on 2D surface. Since ECs known to form tube by self-assemble in a specific length scale channel[21-22], it would be feasible to create a pre-formed endothelial tube network embedded cell sheet which could be inserted between two cell sheets to build vascularized thick tissues. Numerous fields in biology or medicine could benefits from the methods, systems, assays and compositions as disclosed herein, including but not limited to, for example; drug testing, tissue engineering, and cancer studies.

One of ordinary skill in the art can optimize the enzyme concentration and pH to maximize enzyme degradation activity, as well as quantification of relationship between polymer concentration and substrate stiffness to meet his or her particular needs.

The enzyme degradable natural polymer based cell sheet harvest and transfer system is capable of making topographical patterns on substrates. Cell sheet transfer procedure is typically under cell friendly environment (e.g., 37° C., 5% CO2, 20% O2, under media), therefore guaranteeing high cell viability. Cost of production is much cheaper than currently available technology in market and scale up is easy. It is possible to custom make 2D shape and surface patterning in order to recapitulate the complex tissue structure that is critical to tissue function in tissue engineering. Moreover, it is possible to manipulate substrate stiffness in order to modulate or mimic the growth environment of target cells in the cell sheets.

In some embodiments, one of ordinary skill in the art can further tune substrate modulus to provide target cell customized biomechanical growth environments. Cell alignment and high cell viability can be maintained after stacking, and this process can easily be scaled up. Accordingly, the methods, assays, systems and compositions as disclosed herein are useful for rapid and low cost fabrication of three dimensional engineered tissues that accurately mimic native tissue structure and immediately implantable.

Example 4

ECM Composition Change Due to Young's Modulus Difference (ELISA)

Cells respond to their growth environment, especially substrate modulus.[7-8] We illustrate how ECM secretion changes, especially collagen type I, the major component of ECM that directly relates cell sheet mechanical strength due to substrate modulus change. Low (>100 Pa) and high modulus (9-13 kPa) substrates for both CMC-ty and Al-ty were prepared. Mouse myoblast precursor cells (C2C12) were seeded ($1.25 \times 10^5$ cells/ml) and cultured for 7 days. Cells were fixed with 4% paraformaldehyde for 20 min in ice and washed with PBS three times. Samples were blocked with 200 ul 3% BSA (bovine serum albumin)-TBS (Tris-buffered saline) for 1 hour on a rocker platform at room temperature. Then, samples were washed with TBS four times. Samples were treated with collagen type I primary antibody (rabbit, Rockland Immunochemicals, Cat 600-401-103) (2 ug/ml) in 3% BSA-TBS for overnight at 4° C. on a rocker platform. After overnight incubation of primary antibody, samples were washed with TBS five times and incubated with secondary antibody, goat anti-rabbit HRP-linked IgG (Jackson Immunochemicals, Cat 111-035-003) (0.5 µg/ml) for 30 min at room temperature. Samples were washed three times with TBS with 0.1% Tween 20 and 5 times with 200 ul TBS. Before the last wash, developing solution (TMB Microwell Peroxidase Substrate System, KPL) was prepared in a foil-wrapped tube. Samples were incubated with TMB developing solution until blue color development after approximately for 2 minutes, and the reaction was stopped by adding 1N sulfuric acid. An aliquot was taken from each sample and transferred into a 96 well plate. Absorbance was read in duplicate at A570 (Background) and A450 in duplicate within 30 minutes of stopping the reactions. The absorbance values were averaged and the background was subtracted from the averaged A450 value to obtain the relative collagen I absorbance value. The values were normalized with cell sheet dry weight (N=6 for each substrate and modulus type).

Figures 11A, 11B:
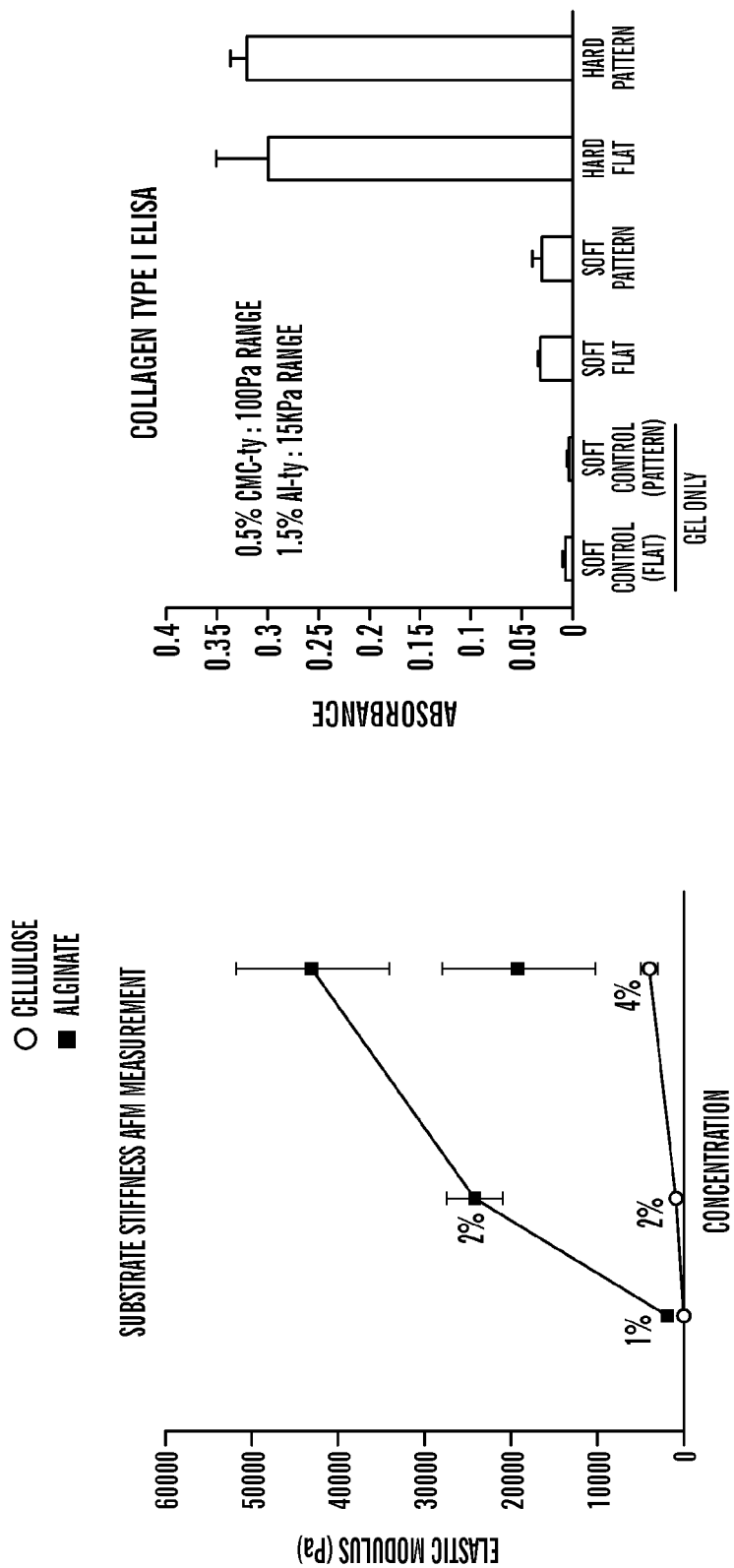
FIG. 11A shows the substrate stiffness AFM measurements of various substrate type varying with percent concentration of substrate material.
FIG. 11B shows the varying increase in collagen type 1 production in the extracellular matrix of cells grown on substrates with varying increase in substrate stiffness.

Collagen type I content comparison. Mouse myoblast (C2C12) were seeded on both soft substrate (0.5% CMC-ty) and hard substrate (1.5% Al-ty). Compared to cells grown on soft substrate, cells on hard substrate produced significantly more collagen I, which leads to differences in cell sheet strength, mainly differences in mechanical strength. (FIG. 11). This assay shows collagen type I production, the major component of ECM that is responsible for mechanical strength changes due to cellular response to substrate stiffness. Therefore, by tuning substrate stiffness, the cell sheet stacking system can accurately mimic native growth environment to produce cell sheets close to native tissue.

Immunohistochemistry

We assessed how skeletal muscle cell sheet development was affected by substrate modulus. C2C12 cells grown on either CMC-ty or Al-ty substrates with two different Young's modulus with growth medium (high glucose (4.5 g/L D-Glucose) Dulbecco's Modified Eagle Medium (DMEM) (Life Technologies, 11995081) supplemented with 10% Fetal Bovine Serum (FBS) (Hyclone, SH30910.03) and 1% Antibiotic-Antimycotic (ABAM) (Life Technologies, 15240-112) for 5 days and with differentiation medium, low glucose (Life technologies, 11885092) supplemented with 2% horse serum (HS) (Hyclone, 26050088) and 1% ABAM for 5 days. Myotube formation was confirmed under phase contrast microscopy (Nikon) before further processing. Cells were fixed with 2% paraformaldehyde for 10 minutes and washed twice with cold PBS. Cells were blocked for 60 minutes with 2% BSA, 2% goat serum, and 0.1% Triton X-100 in 1×PBS containing mouse on mouse blocking solution (Vector laboratory). Sections were incubated with primary antibody either Myosin heavy chain (Clone MF 20) or Myogenin antibodies (eBioscience San Diego, Calif.; Cat #14-6503 and 14-5643 respectively) with 1:50 dilution for 2 hours at room temperature. Cells were subsequently washed 5 times, 3 minutes each with the wash buffer (lx PBS containing 0.05% Tween 20). Cells were subsequently incubated in goat-anti mouse ALEXA Fluor 488 antibody in the dark for an hour. Nuclei were stained with 0.1 g/mL DAPI for 5 minutes followed by washing as described above. Cells were mounted with Vectashield (Vector Laboratories). A Nikon DSFil camera head attached to a Nikon ECLIPSE 50i light microscope system was used to capture images of stained sections. Morphometric analyses were performed using NIS-Elements Basic Research 3.0 software. Differentiation markers and fusion index (number of nuclei per myotube) were evaluated, and qualitative Myosin heavy chain (MF20) and Myogenin expression were assessed. (FIG. 12).

Gene expression analysis. We exemplified the gene expression profile changes, focusing especially on differentiation and proliferation related genes such as Embryonic Myosin Heavy Chain (EMYHC) and Myogenin (MYOG) as a result of changes in the Young's modulus of the substrate. EMYHC is a differentiation marker of developing human skeletal muscle. MYOG is required for the fusion of myogenic precursor cells to either new or previously existing fibers during the process of differentiation in myogenesis. Cell sheets from the substrates were harvested using matching degrading enzyme, namely cellulase for CMC-ty and alginate lyase for Al-ty, and washed twice with ice cold PBS. RNA was extracted with TRIzol reagent (INVITROGEN™, Carlsbad, Calif.) according to the manufacturer's instructions. 1 μg RNA was reverse-transcribed with the High Capacity cDNA Reverse Transcription Kit (Applied Biosystems, Foster City, Calif., USA). Analysis of gene expression was performed by TaqMan assays (Applied Biosystems, Foster City, Calif., USA) on an ABI 7300 Real Time PCR system. 18s ribosomal subunit RNA served as endogenous control, and gene expression was calculated by using the ΔΔCt method.

Figure 12:
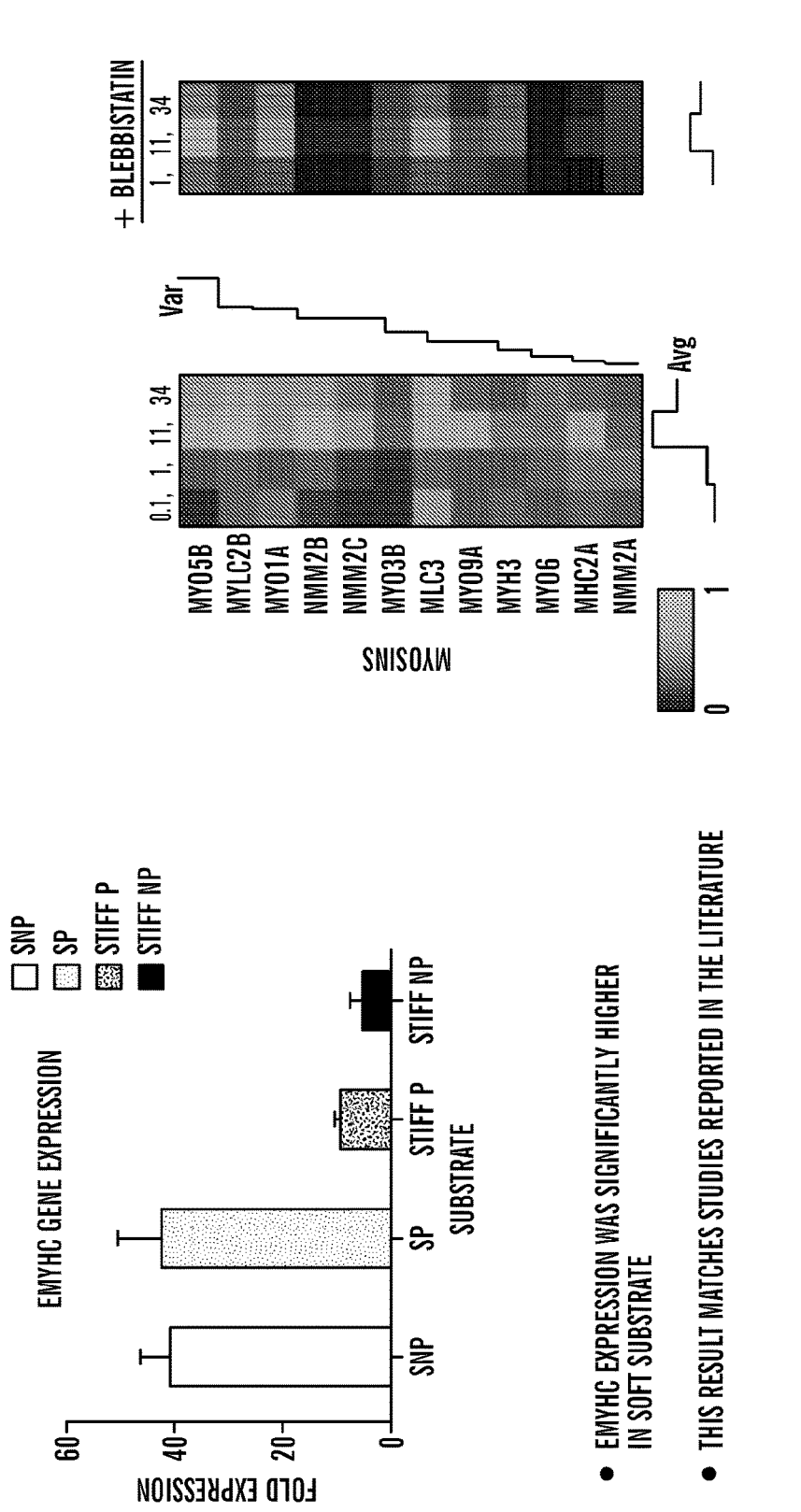
FIG. 12 shows the expression of the EMYHC (Embryonic myosin heavy chain) gene in cells growing/differentiating on substrates of varying stiffness.

FIG. 12 shows that EMYHC expression was significantly higher in soft substrate. This result matches studies reported in the literature in Matrix Elasticity Directs Stem Cell Lineage Specification by Adam J. Engler, et al. 2006, 126: 677-689.

Figure 13:
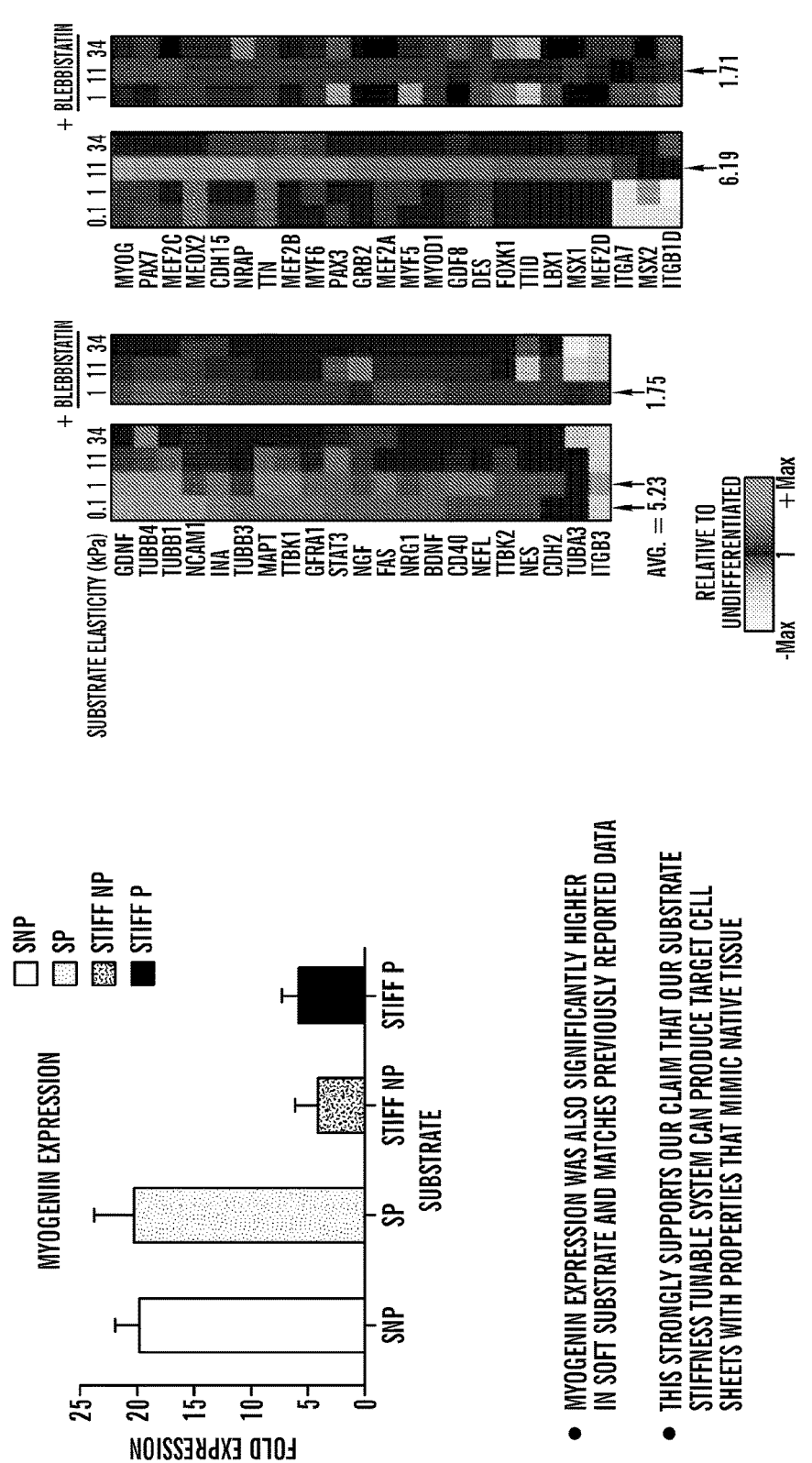
FIG. 13 shows the expression of the Myogenin gene in cells growing/differentiating on substrates of varying stiffness.

FIG. 13 shows that Myogenin expression was also significantly higher in soft substrate and matches previously reported data. This strongly indicates that cell sheet substrate stiffness tunable system can be used to produce target cell sheets with properties that mimic native tissue.

REFERENCES

All references cited herein in the specification and examples are incorporated herein in their entirety by reference.

1. Rhodin, J., Architecture of the vessel wall. In Handbook of Physiology. Waverly Press, Inc, Baltimore, 1-31 (1980).
2. Dahl, S. L. M., Vaughn, M. E., Niklason, L. E., An ultrastructural analysis of collagen in tissue engineered arteries. Annals of Biomedical Engineering 35, 1749-1755 (2007).
3. Glagov, S., Relation of structure to function in arterial walls. Artery 5, 295-304 (1979).
4. Mulvany, M. J. & Aalkjaer, C. Structure and function of small arteries. Physiological Reviews 70, 921-961 (1990).
5. Fung, Y.-C. Biomechanics: Mechanical Properties of Living Tissues. Spinger-Verlag, New York (1993).
6. Wagenseil, J. E., Mecham, R. P., Vascular extracellular matrix and arterial mechanics. Physiological Reviews 89, 957-989 (2009).
7. Martina, M. & Hutmacher, D. W. Biodegradable polymers applied in tissue engineering research: a review. Polymer International 157, 145-157 (2007).
8. Leipzig, N. D. & Shoichet, M. S. The effect of substrate stiffness on adult neural stem cell behavior. Biomaterials 30, 6867-78 (2009).
9. Saha, Krishanu, Albert J Keung, Elizabeth F Irwin, Yang Li, Lauren Little, David V Schaffer, and Kevin E Healy. 2008. "Substrate Modulus Directs Neural Stem Cell Behavior." Biophysical Journal 95 (9) (November 1): 4426-38.
10. Even-Ram, S., Artym, V. & Yamada, K. M. Matrix control of stem cell fate. Cell 126, 645-7 (2006).
11. Voytik-Harben, S. L., Andrew O. B., Beverly Z. W., J. Paul R., Carlton H. L. Small intestinal submucosa: a tissuederived extracellular matrix that promotes tissue-specific growth and differentiation of cells in vitro. Tissue Eng. 4, 157-174 (1998)
12. Murugan, R. & Ramakrishna, S. Design strategies of tissue engineering scaffolds with controlled fiber orientation. Tissue engineering 13, 1845-66 (2007).
13. Kloxin, A. M., Kasko, A. M., Salinas, C. N. & Anseth, K. S. Photodegradable hydrogels for dynamic tuning of physical and chemical properties. Science (New York, N.Y.) 324, 59-63 (2009).
14. Yang, J. et al. Reconstruction of functional tissues with cell sheet engineering. Biomaterials 28, 5033-43 (2007).
15. Sekine, H. et al. Endothelial cell coculture within tissue-engineered cardiomyocyte sheets enhances neovascularization and improves cardiac function of ischemic hearts. Circulation 118, S145-52 (2008).
16. Sasagawa, T. et al. Design of prevascularized three-dimensional cell-dense tissues using a cell sheet stacking manipulation technology. Biomaterials 31, 1646-54 (2010).
17. Elloumi-Hannachi, I., Yamato, M. & Okano, T. Cell sheet engineering: a unique nanotechnology for scaffold-free tissue reconstruction with clinical applications in regenerative medicine. Journal of internal medicine 267, 54-70 (2010).
18. Isenberg, B. C. et al. Micropatterned cell sheets with defined cell and extracellular matrix orientation exhibit anisotropic mechanical properties. Journal of biomechanics 45, 756-61 (2012).
19. Sakai S., Ogushi Y., Kawakami K. Enzymatically cross-linked carboxymethylcellulose-tyramine conjugate hydrogel: Cellular adhesiveness and feasibility for cell sheet technology. Acta Biomaterialia 5 (2), 554-559 (2009).

20. Sakai, S. & Kawakami, K. Synthesis and characterization of both ionically and enzymatically cross-linkable alginate. Acta biomaterialia 3, 495-501 (2007).
21. Patel-Hett, S. & D'Amore, P. a Signal transduction in vasculogenesis and developmental angiogenesis. The International journal of developmental biology 55, 353-63 (2011).
22. Sacharidou, A., Stratman, A. N. & Davis, G. E. Molecular mechanisms controlling vascular lumen formation in three-dimensional extracellular matrices. Cells, tissues, organs 195, 122-43 (2012).
23. I. Kot, B. C. W., Zhang, Z. J., Lee, A. W. C., Leung, V. Y. F. & Fu, S. N. Elastic modulus of muscle and tendon with shear wave ultrasound elastography: variations with different technical settings. PloS one 7, e44348 (2012).
24. Leipzig, N. D. & Shoichet, M. S. The effect of substrate stiffness on adult neural stem cell behavior. Biomaterials 30, 6867-78 (2009).
25. Taylor, Z. & Miller, K. Reassessment of brain elasticity for analysis of biomechanisms of hydrocephalus. Journal of biomechanics 37, 1263-9 (2004).
26. Collinsworth, A. M., Zhang, S., Kraus, W. E. & Truskey, G. a Apparent elastic modulus and hysteresis of skeletal muscle cells throughout differentiation. American journal of physiology. Cell physiology 283, C1219-27 (2002).
27. Athanasiou, K. a, Rosenwasser, M. P., Buckwalter, J. a, Malinin, T. I. & Mow, V. C. Interspecies comparisons of in situ intrinsic mechanical properties of distal femoral cartilage. Journal of orthopaedic research: official publication of the Orthopaedic Research Society 9, 330-40 (1991).
28. Rho, J. Y., Kuhn-Spearing, L. & Zioupos, P. Mechanical properties and the hierarchical structure of bone. Medical engineering & physics 20, 92-102 (1998).
29. Yu, Q., Zhou, J. & Fung, Y. C. Neutral axis location in bending and Young's modulus of different layers of arterial. Am J Physiol Heart Circ Physiol 265:H52-H60 (1993).
30. Brandi et al., Biomaterials, 31, 2010., 3957-3966, Enzymatically degradable poly(ethylene glycol) based hydrogels for adipose tissue engineering.
31. Budick et al., Moving from static to dynamic complexity in hydrogel design. Nat. Commun. 2012, 3:1269 doi: 10.1038/ncomms2271 (2012).
32. Yang et al., Synthesis and Characterization of enzymatically degradable PEG-based peptide containing hydrogels" Macromol. Biosci., 2010, 10; 445-454.
33. Ogushi, Y., Sakai, S., & Kawakami, K. (2007). Synthesis of enzymatically-gellable carboxymethylcellulose for biomedical applications. Journal of bioscience and bioengineering, 104(1), 30-3.
34. Sakai, S., Hashimoto, I., Ogushi, Y., & Kawakami, K. (2007). Peroxidase-Catalyzed Cell Encapsulation in Sub-sieve-Size Capsules of Alginate with Phenol Moieties in Water-Immiscible Fluid Dissolving H2O2. Biomacromolecules, 8(8), 2622-2626.
35. Sasagawa, T., Shimizu, T., Sekiya, S., Haraguchi, Y., Yamato, M., Sawa, Y., & Okano, T. (2010). Design of prevascularized three-dimensional cell-dense tissues using a cell sheet stacking manipulation technology. Biomaterials, 31(7), 1646-54.
36. Sekine, H., Shimizu, T., Hobo, K., Sekiya, S., Yang, J., Yamato, M., Kurosawa, H., et al. (2008). Endothelial cell coculture within tissue-engineered cardiomyocyte sheets enhances neovascularization and improves cardiac function of ischemic hearts. Circulation, 118(14 Suppl), S145-52.

TABLE 1

Stiffness preference for growing or for differentiating different cell types on cell sheets made of different substrate.

| Target cells type or differentiated cells | Stiffness (Pa) | Percent substrate |
|---|---|---|
| Endothelial cells[2] | 6 kPa | 1.2% Al-ty |
| Fibroblast cells[1] | 10 kPa | 1.4% Al-ty |
| Myoblast etc etc[4,5] | 11 kPa | 1.5% Al-ty |
| Myotube formation[6] | 11 kPa | 1.5% Al-ty |
| Mesenchymal stem cell→ myogenic[4,5] | 11 kPa | 1.5% Al-ty |
| Mesenchymal stem → osteogenic[4] | 34 kPa | 3% Al-ty w/ $CaCl_2$ |
| Mesenchymal stem → neurogenic[3,4] | 0.1-1 kPa | 1% CMC-ty |

[1]Yeung, T. et al. Effects of substrate stiffness on cell morphology, cytoskeletal structure, and adhesion. Cell Motil. Cytoskeleton 60, 24-34 (2005).
[2]Levental, I., Georges, P. C. & Janmey, P. a. Soft biological materials and their impact on cell function. Soft Matter 3, 299 (2007).
[3]Leipzig, N. D. & Shoichet, M. S. The effect of substrate stiffness on adult neural stem cell behavior. Biomaterials 30, 6867-78 (2009).
[4]Engler, A. J., Sen, S., Sweeney, H. L. & Discher, D. E. Matrix elasticity directs stem cell lineage specification. Cell 126, 677-89 (2006).
[5]Chaudhuri, T., Rehfeldt, F., Sweeney, H. L. & Discher, D. E. Protocols for Adult Stem Cells. 621, 1-15 (2010).
[6]Engler, A. J. et al. Myotubes differentiate optimally on substrates with tissue-like stiffness: pathological implications for soft or stiff microenvironments. J. Cell Biol. 166, 877-87 (2004).

TABLE 2

A summary of elastic moduli of several different tissues. Experimental elastic moduli of a variety of tissues, including the animal of origin of the tissue, and the testing modality used to determine the modulus. When multiple stiffness values were available, the value at the lowest strain rate and lowest pre-strain was used to approximate the "resting stiffness" of the tissue

| Tissue type | Animal | Testing method | Elastic modulus |
|---|---|---|---|
| Achilles' tendon | Rat | Tension | 310 Mpa |
| Articular cartilage | Bovine | Compression | 950 kPa |
| Skeletal muscle | Rat | Tension | 100 kPa |
| Carotid artery | Mouse | Perfusion | 90 kPa |
| Spinal cord | Human | Tension | 89 kPa |
| Thyroid cancer[a] | Human | Compression | 45 kPa |
| Spinal cord | Rat | Tension | 27 kPa |
| Cardiac muscle | Mouse | Tension | 20-150 kPa |
| Skeletal muscle | Mouse | AFM | 12 kPa |
| Thyroid | Human | Compression | 9 kPa |
| Lung | Guinea pig | Tension | 5-6 kPa |
| Breast tumor | Human | Compression | 4 kPa |
| Kidney | Swine | Rheology | 2.5 kPa |
| Premalignant breast[b] | Human | Indentation | 2.2 kPa |
| Fibrotic liver | Human | Compression | 1.6 kPa |
| Liver | Human | Compression | 640 Pa |
| Lymph containing metastases | Human | Vibrational resonance | 330 Pa |
| Brain | Swine | Indentation | 260-490 Pa |
| Lymph node | Human | Vibrational resonance | 120 Pa |
| Mammary gland | Human | Compression | 160 Pa |
| Fat | Human | Indentation | 17 Pa |

[a]Thyroid papillary adenocarcinoma.
[b]Mammary ductal carcinoma in situ.

TABLE 3

Comparison of cell responses to hydrogels with variable stiffness

| Cell type | Adhesive ligand | Unique response to mechanical properties of matrix |
|---|---|---|
| Aortic smooth muscle cell | Collagen | Minimal spreading on gels with moduli less than 5 kPa, spreading saturates around 15 kPa |
| Neuron | MATRIGEL ® | Increased branching and neurite extension on softer gels (G ≈ 230 Pa) |
| Hepatocyte | MATRIGEL ® | Increased aggregation and differentiation markers on G >150 Pa gels |
| Hepatic stellate cell | MATRIGEL ® | Return from reactive to quiescent phenotype on G <100 Pa materials |
| Mammary epithelial cell | MATRIGEL ® | Polarized mammary gland duct morphogenesis on G <200 Pa |
| Transformed NIH-3T3 fibroblast | Collagen | Transformation causes loss of response to mechanical stimuli |
| Astrocyte | Laminin | Increased spread area and process extension on G >500 Pa |
| Chondrocyte | Chitosan | Increased growth and proliferation on G >10 kPa |
| Alveolar macrophage | Collagen | Increase in cell stiffness and area on G >10 kPa without F-actin stress fiber formation |
| Neutrophil | Fibronectin | Cell spread area is independent of matrix mechanics |
| Myoblast | Collagen | Striated myotube formation on gels G ≈ 12 kPa |
| Platelet | Collagen | Process extension and adhesion are independent of matrix mechanics |
| Human blood outgrowth endothelial cell | Collagen | Branched multi-cellular in vivo-like structures in G ≈ 6 kPa collagen gels |

The invention claimed is:

1. A method of making a multi-layered cell construct comprising the steps of, in the order of:
    a. contacting a second cell layer with a receiving cell layer, wherein the second cell layer is present on a second substrate, and the receiving cell layer comprises at least one cell layer and is present on a receiving substrate, and wherein the receiving substrate has cell-adhesive properties and can be digested by a first enzyme, and the second substrate can be digested by a second enzyme, wherein the receiving substrate and second substrate comprise different enzyme digestible polymers and the first enzyme is different from the second enzyme, then
    b. applying pressure to the second substrate and the receiving substrate, and then
    c. applying a second enzyme to digest the second substrate thereby removing the second substrate, wherein after digestion of the second substrate, the receiving substrate comprises multiple cell layers comprising the at least one receiving cell layer and the second cell layer and wherein there is no substrate between the cell layers of the multiple cell layers, then
    d. after the digestion of the second substrate in step (c), repeating steps (a)-(c) in order at least once, wherein the second cell layer of the multiple cell layers present on the receiving substrate in step (c) is used as the receiving cell layer tar step (a), and then
    e. applying a first enzyme to digest the receiving substrate to form the multi-layered cell construct.

2. The method of claim 1, wherein step (d) is repeated at least 2 times.

3. The method of claim 1, wherein prior to the contacting step, the method comprises:
    a. culturing the cells on a receiving substrate for an appropriate period of time for the cells to form a confluent receiving cell layer, wherein the receiving substrate can be digested by a first enzyme, and
    b. culturing cells on a second substrate for an appropriate period of time for the cells to form a confluent second cell layer, wherein the second substrate can be digested by a second enzyme.

4. The method of claim 3, wherein prior to the contacting step, the method comprises wherein the receiving substrate in step (a), or the second substrate in step (b), or both, are coated with gelatin prior to culturing the cells on the receiving substrate or second substrate for an appropriate period of time to form a confluent cell layer.

5. The method of claim 3, wherein prior to the contacting step, the method comprises wherein the receiving substrate in step (a), or the second substrate in step (b), or both, are a topographically patterned substrate surface for culturing the cells on the receiving substrate or second substrate for an appropriate period of time to form a confluent patterned cell layer.

6. The method of claim 1, wherein the receiving cell layer and second cell layer have the same cell types.

7. The method of claim 1, wherein the receiving cell layer and second cell layer have different cell types.

8. The method of claim 1, wherein the receiving substrate and the second substrate are hydrogels.

9. The method of claim 1, wherein the receiving substrate comprises carboxylmethyl cellulose (CMC) or alginate (Al), and the first enzyme is cellulose or alginate lyase.

10. The method of claims 9, wherein the carboxylmethyl cellulose (CMC) or alginate (Al) are conjugated with tyramine (Ty).

11. The method of claim 1, wherein the first and second enzymes do not digest the extracellular matrices of cells (EMC).

12. The method of claim 1, wherein the second substrate and the receiving substrates are patterned substrates or have a predetermined substrate stiffness to maintain the cell-specific characteristics of the cells in the cell layer on the substrate.

13. The method of claim 1, wherein the second cell layer or the receiving cell layer, or both, comprise cells selected from the group consisting of: mesenchymal stem cells (MSCs), myocyte precursor cells, myocytes, fibroblasts, chondrocytes, endothelial cells, epithelial cells, embryonic stem cells (ESCs), hematopoietic stem cells, anchorage-dependent cell precursors, induced pluripotent stem cells (iPSCs), cardiomyocytes, and combinations thereof.

14. The method of claim 1, wherein the second cell layer or the receiving cell layer, or both, comprise human cells.

15. The method of claim 1, wherein the receiving substrate or second substrate, or both, are coated with gelatin.

16. The method of claim 1, wherein the receiving substrate or second substrate, or both, are a topographically patterned substrate surface.

\* \* \* \* \*